United States Patent
Kelly et al.

(10) Patent No.: US 10,736,976 B2
(45) Date of Patent: Aug. 11, 2020

(54) RADIOLABELED ANTI-PD-L1 ANTIBODIES FOR IMMUNO-PET IMAGING

(71) Applicant: Regeneron Pharmaceuticals, Inc., Tarrytown, NY (US)

(72) Inventors: Marcus Kelly, New York, NY (US); Dangshe Ma, Millwood, NY (US); William Olson, Yorktown Heights, NY (US); Gavin Thurston, Briarcliff Manor, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 15/829,311

(22) Filed: Dec. 1, 2017

(65) Prior Publication Data
US 2018/0161464 A1    Jun. 14, 2018

Related U.S. Application Data

(60) Provisional application No. 62/428,672, filed on Dec. 1, 2016, provisional application No. 62/457,267, filed on Feb. 10, 2017, provisional application No. 62/569,773, filed on Oct. 9, 2017.

(51) Int. Cl.
| | |
|---|---|
| *A61K 51/10* | (2006.01) |
| *C07K 16/28* | (2006.01) |
| *A61K 51/04* | (2006.01) |
| *C07K 16/22* | (2006.01) |
| *C07K 19/00* | (2006.01) |

(52) U.S. Cl.
CPC ...... *A61K 51/1045* (2013.01); *A61K 51/0474* (2013.01); *A61K 51/1093* (2013.01); *C07K 16/22* (2013.01); *C07K 16/2827* (2013.01); *C07K 19/00* (2013.01); *A61K 2121/00* (2013.01); *C07K 2317/515* (2013.01); *C07K 2317/565* (2013.01)

(58) Field of Classification Search
CPC .. A61K 49/00; A61K 49/002; A61K 49/0058; A61K 51/00; A61K 51/1045; A61K 51/1093; A61K 51/0474; A61K 2121/00; A61K 2123/00; A61K 51/08; A61K 51/10; C07K 2317/622; C07K 19/00; C07K 16/22; C07K 16/2827; C07K 2317/565; C07K 2317/515
USPC .......... 424/1.11, 1.49, 1.65, 1.81, 1.85, 1.89, 424/9.1, 9.2, 9.3, 9.4, 9.5, 9.6, 1.69; 514/1, 1.1; 534/7, 10–16
See application file for complete search history.

(56) References Cited

U.S. PATENT DOCUMENTS

| | | |
|---|---|---|
| 4,680,338 A | 7/1987 | Sundoro |
| 5,332,567 A | 7/1994 | Goldenberg |
| 5,639,879 A | 6/1997 | Mease et al. |
| 6,329,503 B1 | 12/2001 | Afar et al. |
| 6,814,951 B1 | 11/2004 | Thiele et al. |
| 7,387,772 B1 | 6/2008 | Hansen et al. |
| 8,545,809 B2 | 10/2013 | D'Souza et al. |
| 8,771,966 B2 | 7/2014 | Dennis et al. |
| 9,359,437 B2 | 6/2016 | Davis et al. |
| 9,429,584 B2 | 8/2016 | Matsumura et al. |
| 9,475,874 B2 | 10/2016 | Sawada et al. |
| 9,546,206 B2 | 1/2017 | Ring et al. |
| 9,562,087 B2 * | 2/2017 | Ring ................ C07K 14/70503 |
| 9,751,945 B2 | 9/2017 | Ploegh et al. |
| 10,081,684 B2 | 9/2018 | Ploegh et al. |
| 2003/0077602 A1 | 4/2003 | Rosen et al. |
| 2003/0170697 A1 | 9/2003 | Goldenberg |
| 2004/0018557 A1 | 1/2004 | Qu et al. |
| 2004/0185040 A1 | 9/2004 | Garcia-Martinez et al. |
| 2004/0253232 A1 | 12/2004 | Jakobovits et al. |
| 2005/0003469 A1 | 1/2005 | Watkins et al. |
| 2005/0208043 A1 | 9/2005 | Adams et al. |
| 2005/0276812 A1 | 12/2005 | Ebens et al. |
| 2006/0177451 A1 | 8/2006 | Van Den Oudenrijn et al. |
| 2006/0246005 A1 | 11/2006 | Yang et al. |
| 2007/0037148 A1 | 2/2007 | Fong et al. |
| 2007/0087005 A1 | 4/2007 | Gregory et al. |
| 2007/0122346 A1 | 5/2007 | Uzgiris et al. |
| 2007/0160530 A1 | 7/2007 | Jakobovits et al. |
| 2007/0280945 A1 | 12/2007 | Stevens et al. |
| 2008/0193376 A1 | 8/2008 | Tawakol et al. |
| 2008/0260650 A1 | 10/2008 | Tawakol et al. |
| 2009/0130108 A1 | 5/2009 | Reiter |
| 2009/0203538 A1 | 8/2009 | Sugioka et al. |

(Continued)

FOREIGN PATENT DOCUMENTS

| | | |
|---|---|---|
| DE | 10339820 A1 | 3/2005 |
| DE | 102012104504 A1 | 11/2013 |

(Continued)

OTHER PUBLICATIONS

Jauw et al. (2016) "Immuno-PositronEmissionRob'sographywithZirconium-89-Labeled Monoclonal Antibodies in Oncology: What Can We Learn from Initial Clinical Trials?" Frontiers in Pharmacology, vol. 7, Article 131, 15 pages.

(Continued)

*Primary Examiner* — D. L. Jones
(74) *Attorney, Agent, or Firm* — FisherBroyles, LLP; Cara L. Crowley-Weber; Robert Chang

(57) ABSTRACT

Radiolabeled anti-PD-L1 antibodies and their use in immuno-PET imaging are provided herein. Included are methods of detecting the presence of PD-L1 proteins in a patient or sample.

6 Claims, 12 Drawing Sheets

Specification includes a Sequence Listing.

(56) References Cited

U.S. PATENT DOCUMENTS

| | | | |
|---|---|---|---|
| 2009/0208489 A1 | 8/2009 | Veiby Ole Petter et al. |
| 2009/0208937 A1 | 8/2009 | Chinnaiyan et al. |
| 2009/0297439 A1 | 12/2009 | Comoglio et al. |
| 2010/0111856 A1 | 5/2010 | Gill et al. |
| 2010/0279301 A1 | 11/2010 | Chinnaiyan et al. |
| 2010/0285037 A1 | 11/2010 | Abo et al. |
| 2011/0076287 A1 | 3/2011 | Cohen et al. |
| 2011/0311517 A1 | 12/2011 | Li et al. |
| 2012/0058906 A1 | 3/2012 | Smider et al. |
| 2012/0195905 A1 | 8/2012 | Bedian et al. |
| 2012/0225060 A1 | 9/2012 | Lee et al. |
| 2013/0195845 A1 | 8/2013 | Fendly et al. |
| 2013/0209481 A1 | 8/2013 | Zhou et al. |
| 2014/0112873 A1 | 4/2014 | Gillies et al. |
| 2014/0193424 A1 | 7/2014 | Luo et al. |
| 2014/0322129 A1 | 10/2014 | Leong et al. |
| 2014/0377174 A1 | 12/2014 | Houthoff et al. |
| 2015/0056209 A1 | 2/2015 | Witztum et al. |
| 2015/0191543 A1 | 7/2015 | Wu et al. |
| 2015/0203580 A1 | 7/2015 | Papadopoulos et al. |
| 2015/0299133 A1 | 10/2015 | Osterkamp et al. |
| 2016/0000946 A1 | 1/2016 | Cheng et al. |
| 2016/0136309 A1 | 5/2016 | Rosch et al. |
| 2016/0145350 A1 | 5/2016 | Lonberg et al. |
| 2016/0151515 A1 | 6/2016 | Joubert et al. |
| 2016/0157469 A1 | 6/2016 | Burova et al. |
| 2017/0029507 A1 | 2/2017 | Ho et al. |
| 2017/0119913 A1 | 5/2017 | Osterkamp et al. |
| 2017/0258948 A1 | 9/2017 | Morin et al. |
| 2017/0283442 A1 | 10/2017 | D'Souza et al. |
| 2018/0015154 A1 | 1/2018 | Weichert et al. |
| 2018/0043041 A1 | 2/2018 | Bansal et al. |
| 2018/0055947 A1 | 3/2018 | Van Dongen et al. |
| 2018/0071413 A1* | 3/2018 | Olive .............. A61K 51/1027 |
| 2018/0078662 A1 | 3/2018 | Agnew et al. |
| 2018/0126012 A1 | 5/2018 | Weichert et al. |
| 2018/0161464 A1 | 6/2018 | Kelly et al. |

FOREIGN PATENT DOCUMENTS

| | | |
|---|---|---|
| EP | 1541680 A1 | 6/2005 |
| EP | 2196541 A1 | 6/2010 |
| EP | 2216344 A1 | 8/2010 |
| EP | 2540745 A1 | 1/2013 |
| EP | 3266465 A1 | 7/2016 |
| WO | 1990/13256 A1 | 11/1990 |
| WO | 1998/17797 A1 | 4/1998 |
| WO | 1998/39027 A1 | 9/1998 |
| WO | 1999/055842 A1 | 11/1999 |
| WO | 2004/016225 A2 | 2/2004 |
| WO | 2004/101756 A2 | 11/2004 |
| WO | 2005/068503 A2 | 7/2005 |
| WO | 2005/113601 A2 | 12/2005 |
| WO | 2006/034488 A2 | 3/2006 |
| WO | 2006/053110 A2 | 5/2006 |
| WO | 2006/099141 A2 | 9/2006 |
| WO | 2008/052187 A2 | 5/2008 |
| WO | 2008/067283 A2 | 6/2008 |
| WO | 2008/124467 A1 | 10/2008 |
| WO | 2008/141044 A2 | 11/2008 |
| WO | 2009/005809 A2 | 1/2009 |
| WO | 2009/033011 A1 | 3/2009 |
| WO | 2009/045957 A1 | 4/2009 |
| WO | 2009/0068204 A1 | 6/2009 |
| WO | 2009/073533 A2 | 6/2009 |
| WO | 2009/0120769 A1 | 10/2009 |
| WO | 2009/129578 A1 | 10/2009 |
| WO | 2010/016766 A2 | 2/2010 |
| WO | 2010/111282 A1 | 9/2010 |
| WO | 2011/0021014 A2 | 2/2011 |
| WO | 2011/051349 A1 | 5/2011 |
| WO | 2011/056983 A1 | 5/2011 |
| WO | 2011/153346 A1 | 12/2011 |
| WO | 2012/045752 A1 | 4/2012 |
| WO | 2012/087962 A2 | 6/2012 |
| WO | 2012/098407 A1 | 7/2012 |
| WO | 2012/177595 A1 | 12/2012 |
| WO | 2013/010573 A1 | 1/2013 |
| WO | 2013/025779 A1 | 2/2013 |
| WO | 2013/028907 A1 | 2/2013 |
| WO | 2013/061083 A1 | 5/2013 |
| WO | 2013/063312 A1 | 5/2013 |
| WO | 2013/070468 A1 | 5/2013 |
| WO | 2013/071142 A1 | 5/2013 |
| WO | 2013/138696 A1 | 9/2013 |
| WO | 2013/149159 A1 | 10/2013 |
| WO | 2013/165940 A1 | 11/2013 |
| WO | 2013/169625 A1 | 11/2013 |
| WO | 2013/173496 A2 | 11/2013 |
| WO | 2013/177055 A2 | 11/2013 |
| WO | 2014/151634 A1 | 9/2014 |
| WO | 2014/159087 A1 | 10/2014 |
| WO | 2014/159835 A1 | 10/2014 |
| WO | 2014/159981 A2 | 10/2014 |
| WO | 2014/183006 A2 | 11/2014 |
| WO | 2014/200969 A2 | 12/2014 |
| WO | 2014/210064 A1 | 12/2014 |
| WO | 2015/053871 A2 | 4/2015 |
| WO | 2015/061209 A1 | 4/2015 |
| WO | 2015/073746 A2 | 5/2015 |
| WO | 2015/075445 A1 | 5/2015 |
| WO | 2015/089344 A1 | 6/2015 |
| WO | 2015/112805 A1 | 7/2015 |
| WO | 2015/132602 A1 | 9/2015 |
| WO | 2015/140212 A1 | 9/2015 |
| WO | 2015/179658 A2 | 11/2015 |
| WO | 2015/191715 A1 | 12/2015 |
| WO | 2016/020502 A1 | 2/2016 |
| WO | 2016/040723 A1 | 3/2016 |
| WO | 2016/040724 A1 | 3/2016 |
| WO | 2016/040868 A1 | 3/2016 |
| WO | 2016/058056 A1 | 4/2016 |
| WO | 2016/077518 A1 | 5/2016 |
| WO | 2016/086021 A1 | 6/2016 |
| WO | 2016/144873 A2 | 9/2016 |
| WO | 2016/162368 A1 | 10/2016 |
| WO | 2016/191186 A1 | 12/2016 |
| WO | 2017/059397 A1 | 4/2017 |
| WO | 2017/087826 A1 | 5/2017 |
| WO | 2017/201111 A1 | 11/2017 |
| WO | 2017/213494 A1 | 12/2017 |
| WO | 2017/223565 A1 | 12/2017 |
| WO | 2018/049083 A1 | 3/2018 |
| WO | 2018/058125 A1 | 3/2018 |
| WO | 2018/083705 A1 | 5/2018 |
| WO | 2018/128664 A2 | 7/2018 |

OTHER PUBLICATIONS

Josefsson et al. (2016) "Imaging Biodistribution, and Dosimetry of Radionuclide-Labeled PD-L1 Antibody in an Immunocompetent Mouse Model of Breast Cancer", Cancer Research 76(2):472-479.
Junutula et al. (2008) "Rapid identification of reactive cysteine residues for site-specific labeling of antibody-Fabs", Journal of Immunological Methods, 332(1-2):41-52.
Junutula et al. (2008) "Site-specific conjugation of a cytotoxic drug to an antibody improves the therapeutic index", Nature Biotechnology, 26(8):925-932.
Kabat (1991) "Sequences of Proteins of Immunological Interest," National Institutes of Health, Bethesda, Md., 147:1709-1719.
Keliher et al. (2011) "89Zr-labeled dextran nanoparticles allow in vivo macrophage imaging.", Bioconjugate Chemistry, 22(12):2383-2389.
Kelly et al. (2017) "Immuno-PET using Zirconium-89 (89Zr) radiolabeled fully human anti-PD-L1 positive tumors in preclinical mouse models", Journal of Nuclear Medicine 58(S1):618.
Lamberts et al. (2015) "ImmunoPET with Anti-Mesothelin Antibody in Patients with Pancreatic and Ovarian Cancer Before Anti-Mesothelin Antibody-Drug Conjugate Treatment", Clinical Cancer Research, 22(7):1642-1652.
Lasorsa et al. (2016) "Probing the interaction between cisplatin and the therapeutic monoclonal antibody trastuzumab", RSC Adavances, 6(35):29229-29236.

(56) References Cited

OTHER PUBLICATIONS

Le Beau et al. (2013), "Targeting uPAR with antagonistic recombinant human antibodies in aggressive breast cancer", Cancer Res, 73(7):2070-2081.
Leong et al. (2015) "An Anti-B7-H4 Antibody-Drug Conjugate for the Treatment of Breast Cancer.", Molecular Pharmaceutics, 12(6):1717-1729.
Lesniak et al. (2016) "PD-L1 Detection in Tumors Using [64Cu]Atezolizumab with PET", Bioconjugate Chemistry 27 (9):2103-2110.
Li and Zhu (2016) "Immuno-PET imagining using 89Zr labeled PD-L1 antibody in non-small cell lung cancer Xenograft" J. Nucl. Med., 57(S2):337.
Li et al. (2012) "MLN9708 Shows Encouraging Results for the Treatment of Multiple Myeloma (ASCO 2012)", The Myeloma Beacon, 3pages.
Li et al. (2014) "Addition of bevacizumab enhances antitumor activity of erlotinib against non-small cell lung cancer xenografts depending on VEGF expression", Cancer Chemother Pharmacol., 74(6):1297-305; Abstract.
Lloyd (1999) The Art, Science and Technology of Pharmaceutical Compounding, 8pgs.
Lu et al. (2009) "Abstract#1233: Development of anti-glypican 3 therapeutic antibodies", AACR Annual Meeting, 50:296.
Martin et al. (1989) "Modeling antibody hypervariable loops: A combined algorithm", Proc. Natl. Acad. Sci. USA 86:9268-9272.
Maute et al. (2015) "Engineering high-affinity PD-1 variants for optimized immunotherapy and immuno-PET imaging", Proc Natl Acad Sci U S A, 112(47):E6506-E6514.
Meijs et al. (1997) "Zirconium-labeled monoclonal antibodies and their distribution in tumor-bearing nude mice", J Nucl Med, 38(1):112-118.
Mindt et al. (2014) "Octadetante bifuntional chelating agent for Zr-89 based Imagining probes", Technology Opportunity, Ref. No. UZ-15/736, 1 page.
Morita et al. (2004) "Neonatal lethality of LGR5 null mice is associated with ankyloglossia and gastrointestinal distension", Mol Cell Biol., 24(22):9736-9743.
Nakano et al. (2010) "Generation of a humanized anti-glypican 3 antibody by CDR grafting and stability optimization", Anti-Cancer Drugss, 21(10):907-916.
Nakano et al. (2009) "Anti-glypican 3 antibodies cause ADCC against human hepatocellular carcinoma cells", BBRC, 378(2):279-284.
Natarajan et al. (2015) "Novel Radiotracer for ImmunoPET Imaging of PD-1 Checkpoint Expression on Tumor Infiltrating Lymphocytes", Bioconjug Chem, 26(10):2062-2069.
Nijland et al. (2019) "Molecular Imaging Using Radiolabeled Atezolizumab to AssessAtezolizumab Biodistribution in Lymphoma Patients", University Medical Center Groningen, ClinicalTrials.gov Identifier: NCT03850028, 11 pages.
Onda et al. (2005) "New monoclonal antibodies to mesothelin useful for immunohistochemistry, fluorescence-activated cell sorting, Western blotting, and ELISA", Clin Cancer Res, 11(16):5840-5846.
Onda et al. (2006) "Megakaryocyte Potentiation Factor Cleaved from Mesothelin Precursor Is a Useful Tumor Marker in the Serum of Patients with Mesothelioma", Clin Cancer Res, 12(14 Pt 1):4225-4231.
Oosting et al. (2015) "89Zr-Bevacizumab PET Visualizes Heterogeneous TracerAccumulation in Tumor Lesions of Renal Cell Carcinoma Patients and Differential Effects of Antiangiogenic Treatment", The Journal of Nuclear Medicine, 56(1):63-69.
Padldan et al. (1995) "Identification of specificity-determining residues in antibodies", FASEB J. 9:133-139.
Jandya et al. (2015) "Di-macrocyclic terephthalamide ligands as chelators for the PET radionuclide zirconium-89", Chem Commun (Camb), 51(12):2301-2303.

Pantin et al. (2012) "Optimization of an Intra-Bone Hematopoietic Stem Cell Delivery Technique in a Swine Model (Abstract 2990)", Blood, 120(21):2990.
Pearson (1994) "Using the FASTA Program to Search Protein and DNA Sequence Databases", Methods Mol. Biol. 24:307-331.
Perk et al. (2010) "p-Isothiocyanatobenzyl-desferrioxamine: a new bifunctional chelate for facile radiolabeling of monoclonal antibodies with zirconium-89 for immuno-PET imaging", Eur. J. Nucl. Med. Mol Imaging, 37(2):250-259.
Petrick et al. (2015) "In Vitro and in Vivo Comparison of Selected Ga-68 and Zr-89 Labelled Siderophores", Mol. Imaging Biol., 18:344-352.
Phung et al., (2012) "High-affinity monoclonal antibodies to cell surface tumor antigen glypican-3 generated through a combination of peptide immunization and flow cytometry screening", MAbs, 4(5):592-599.
Price et al. (2014) "H6phospa-trastuzumab: bifunctional methylenephosphonate-based chelator with 89Zr, 111In and 177Lu", Dalton Trans., 43(1):119-131.
Pritsch et al. (1993) "V Gene Usage by Seven Hybrids Derived From CD5+ B-Cell Chronic Lymphocytic Leukemia and Displaying Autoantibody Activity", Blood, 82(10):3103-3112.
Ribas (2012) "Tumor immunotherapy directed at PD-1.", N. Engl. J. Med., 366(26):2517-2519.
Ricart et al. (2007) "Technology Insight: Cytotoxic drug immunoconjugates for cancer therapy", Nature Clinical Practice Oncology, 4(4):245-255.
Sasaki et al. (2010) "Establishment of a novel monoclonal antibody against LGR5", BBRC, 394(3):498-502.
Sheridan (2012) "Cautious optimism surrounds early clinical data for PD-1 blocker", Nature Biotechnology 30 (8):729-730.
Smith et al. (2010) "Vascular endothelial growth factor receptors VEGFR-2 and VEGFR-3 are localinzed primarily to the vasculature in human primary solid cancers", Clin Cancer Res. 16(14):3548-3561.
Souza et al. (2005) "Peripheral B Cells Latently Infected With Epstein-Barr Virus Display Molecular Hallmarks of Classical Antigen-Selected Memory B Cells", Proc Natl Acad Sci USA, 102(50):18093-18098.
Takahashi et al. (2010) "Significance of Lgr5Cancer Stem Cells in the Colon and Rectum", Annals of Surgical Oncology, 18(4):1166-1174.
Tavare et al. (2016) "An Effective Immuno-PET Imaging Method to Monitor CD8-Dependent Responses to Immunotherapy", Cancer Research , 76(1):73-82.
Terrovitis et al. (2010) "Assessment and Optimization of Cell Engraftment After Transplantation Into the Heart", Circ Res., 106(3):479-494.
Tinianow et al. (2010) "Site-specifically 89Zr-labeled monoclonal antibodies for ImmunoPET", Nucl Med Biol., 37 (3):289-297.
Vajdos et al. (2002) "Comprehensive Functional Maps of the AntigenbindingSite of an Anti-ErbB2 Antibody Obtained with Shotgun Scanning Mutagenesis", J Mol Biol 320:415-428.
Valenzuela et al. (2003) "High-throughput engineering of the mouse genome coupled with high-resolution expression analysis", Nat. Biotechnol. 21:652-659.
Al-Lazikani et al. (1997) "Standard conformations for the canonical structures of immunoglobulins", J. Mol. Biol. 273:927-948.
Alley et al. (2010) "Antibody-drug conjugates: targeted drug delivery for cancer", Current Opinion in Chemical Biology, 14(4):529-537.
Altschul et al. (1990) "Basic Local Alignment Search Tool", J. Mol. Biol. 215: 403-410.
Altschul et al. (1997) "Gapped BLAST and PSI-BLAST: a new generation of protein database search programs", Nucleic Acids Res. 25(17):3389-3402.
Alzimami et al. (2014) "Comparison of Zr-89, I-124, and F-18 Imaging Characteristics in PET Using Gate Monte Carlo Simulations: Imaging" International Journal of Radiation Oncology, 88:502.
Anonymus (2015) "Human MICL/CLEC12A Antibody,Monoclonal Mouse IgG2B Clone# 687317", Catalog No. MAB294611, p. 1.
Askmyr et al. (2013) "Selective killing of candidate AML stem cells by antibody targeting of IL1RAP", Blood, 121 (18):3709-3713.

(56) References Cited

OTHER PUBLICATIONS

Bannerman et al. (2009) "Abstract #5635: The Proteasome Inhibitor MLN9708 Has Strong Anti-Tumor Activity in the Murine Bone Marrow Compartment in Vivo", Cancer Research, AACR Annual Meeting, 5 pages.
Bartel et al. (2009) "F18-Fluorodeoxyglucose Positron Emission Tomography in the Context of Other Imaging Techniques and Prognostic Factors in Multiple Myeloma", Blood, 114(10):2068-2076.
Beaino et al. (2014) "PET Imaging of Very Late Antigen-4 in Melanoma:Comparison of 68Ga- and 64Cu-Labeled NODAGA and CB-TE1A1P-LLP2A Conjugates" The Journal of Nuclear Medicine, 55(11):1857-1862.
Boerman and Oyen (2011) "Immuno-PET of Cancer: A Revival of Antibody Imaging", Journal of Nuclear Medicine, 52(8):1171-1172.
Chang et al. (2015) "Metabolic Competition in the Tumor Microenvironment is a Driver of Cancer Progression", Cell, 162:1229-1241.
Chatterjee et al. (2016) "A humanized antibody for imaging immune checkpoint ligand PD-L1 expression in tumors", Oncotarget 7(9):10215-10227.
Chattopadhyay et al. (2009) "Sequence, structure, function, immunity: structural genomics of costimulation" Immunol. Rev. 229(1):356-386.
Chen et al. (2013) "Molecular mechanisms of T cell co-stimulation and co-inhibition", Nature Rev. Immunol. 13 (4):227-242.
De Lau et al. (2011) "Lgr5 homologues associate with Wnt receptors and mediate R-spondin signalling", Nature, 476 (7360):293-297.
De Vries "Antibody immunotherapy imaging." Department of Medical Oncology University Medical Center Groningen, The Netherlands, 16 pages.
De Vries (2015) "MPDL3280A-imaging-IST-UMCG", ClinicalTrials.gov Identifier: NCT02453984, University Medical Center Groningen, 10 pages.
Deng et al. (2016) "Preclinical pharmacokinetics, pharmacodynamics, tissue distribution, and tumor penetration of anti-PD-L1 monoclonal antibody, an immune checkpoint inhibitor", mAbs, 8(3):593-603.
Deri et al. (2015) "p-SCN-Bn-HOPO: A Superior Bifunctional Chelator for (89)Zr ImmunoPET", Bioconjugate Chem., 26(12) 2579-2591.
Dijkers et al. (2019) "Biodistribution of 89Zr-trastuzumab and PETImaging of HER2-Positive Lesions in Patients With Metastatic Breast Cancer", Clinical Pharmacology and Therapeutics, 87(5):586-592.
Dijkers et al. (2009) "Development and Characterization of Clinical-Grade 89Zr-Trastuzumab for HER2/neu ImmunoPET Imaging", Journal of Nuclear Medicine, 50(6):974-981.
Dong et al. (1999) "B7-H1, a third member of the B7 family, co-stimulates T-cell proliferation and interleukin-10 secretion" Nature Medicine, 5(12):1365-1369.
Feng et al. (2013) "Glypican-3 antibodies: A new therapeutic target for liver cancer" FEBS Letters, 588(2):377-382.
Feng et al. (2013) "Therapeutically targeting glypican-3 via a conformation-specific single-domain antibody in hepatocellular carcinoma", Proceedings of the National Academy of Sciences, 110(12):E1083-E1091.
Feng et al. (2009) "A novel human monoclonal antibody that binds with high affinity to mesothelin-expressing cells and kills them by antibody-dependent cell-mediated cytotoxicity", Molecular Cancer Therapeutics, American Association of Cancer Research, 8(5):1113-1118.
Fischer et al. (2013) "89Zr, a Radiometal Nuclide with High Potential for Molecular Imaging with PET: Chemistry, Applications and Remaining Challenges", Molecules, 18:6469-6490.
Fisher et al. (2002) "Generation of Monocolonal Antibodies Specific for Human Kallikrein 2 (hK2) Using hK2-Expresing Tumors", The Prostate, 51:153-165.
Francisco et al. (2010) "The PD-1 pathway in tolerance and autoimmunity", Immunol Rev., 236:219-242.

Freeman (2008) "Structures of PD-1 with its ligands: sideways and dancing cheek to cheek." PNAS, 105 (30):10275-10276.
Gao et al. (2014) "Lgr5 over-expression is positively related to the tumor progression and HER2 expression in stage pTNM IV colorectal cancer", Int. J. Clin. Exp. Pathol., 7(4):1572-1579.
Garcia-Teijido et al. (2016) "Tumor-Infiltrating Lymphocytes in Triple Negative Breast Cancer: The Future of Immune Targeting", Clin Med Insights Oncol, 10(S1):31-39.
Gebhart et al. (2015) "Molecular imaging as a tool to investigate heterogeneity of advanced HER2-positive breast cancer and to predict patient outcome under trastuzumab emtansine (T-DM1); the ZEPHIR trial", Annals of Oncology Advance Access, 22 pages.
GenBank Accession No. CAJ48864.1—Putative Membrane Protein [Bordetella avium 197N].
GenBank Accession No. NP_005009.2.
GenBank Accession No. NP_005182.1.
Glunde et al. (2011) "Magnetic Resonance Spectroscopy and Imaging Guidance in Molecular Medicine: Targeting and Monitoring of Choline and Glucose Metabolism in Cancer", NMR in Biomedicine, 24(6):673-690.
Gonnet et al. (1992) "Exhaustive Matching of the Entire Protein Sequence Database", Science 256:1443-1445.
Govindan et al. (2005) "Deferoxamine as a chelator for 67Ga in the preparation of antibody conjugates", Nuclear Medicine and Biology, 32(5):513-519.
Gupta et al. (2010) "Clinical Pharmacokinetics of Intravenous and Oral MLN9708, An Investigational Proteasome Inhibitor: An Analysis of Data From Four Phase 1 Monotherapy Studies", Blood, 116:1813.
Hanaoka et al. (2015) "Glypican-3 Targeted Human Heavy Chain Antibody as a Drug Carrier for Hepatocellular Carcinoma Therapy", Molecular Pharmaceutics, 12(6):2151-2157.
Hassan et al. (2007) "Preclinical evaluation of MORAb-009, a chimeric antibody targeting tumor-associated mesothelin", Cancer Immunity, Academy of Cancer Immunology, 7:20.
Herbst et al. (2014) "Predictive correlates of response to the anti-PD-L1 antibody MPDL3280A in cancer patients" Nature 515(7528):563-567.
Heskamp et al. (2015) "Noninvasive Imaging of Tumor PD-L1 Expression Using Radiolabeled Anti-PD-L1 Antibodies", Cancer Res, 75(14):2928-2936.
Higashikawa et al. (2014) "64Cu-DOTA-Anti-CTLA-4 mAb Enabled PET Visualization of CTLA-4 on the T-Cell Infiltrating Tumor Tissues", PLoS One, 9(11):e109866, 8 pages.
Holland et al. (2009) "Standarized Methods for the Production of High Specific-Activity Zirconium-89", Nucl. Biol., 36(7):729-739.
Huang et al. (2010) "Biodistribution, toxicity and radiation dosimetry studies of the serotonin transporter radioligand 4-[18F]-ADAM in rats and monkeys", Eur J Nucl Med Mol Imaging, 37(3):545-555.
International Commission on Radiological Protection. 1990 Recommendations of the International Commission on Radiological Protection. ICRP Publication 60, Pergamon Press, New York, 1991, 1 page Abstract.
Iyer et al. (2011) "Antibody drug conjugates—Trojan horses in the war on cancer", Journal of Pharmacological and Toxicological Methods, 64(3):207-212.
Järås et al. (2010) "Isolation and killing of candidate chronic myeloid leukemia stem cells by antibody targeting of IL-1 receptor accesory protein", Proceedings of the National Academy of Sciences, National Academy of Sciences, US, 107(37):16280-16285.
Van De Watering et al. (2014) "Zirconium-89 Labeled Antibodies: A New Tool for Molecular Imaging in Cancer Patients", Biomed Research international, Article ID 203601, 2014:1-13.
Van Dongen et al. (2007) "Immuno-PET: a navigator in monoclonal antibody development and applications", The Oncologist, 12:1379-1389.
Vansteenkiste et al. (1999) "Prognostic Importance of the Standardized Uptake Value on 18F-Fluoro-2-Deoxy-Glucose-Positron Emission Tomography Scan in Non-Small-Cell Lung Cancer: An Analysis of 125 Cases", J Clin Oncol., 17(10):3201-3206.
Verel et al. (2003) "89Zr immuno-PET: comprehensive procedures for the production of 89Zr-labeled monoclonal antibodies", J Nucl Med., 44(8):1271-1281.

(56) References Cited

OTHER PUBLICATIONS

Vosjan et al. (2010) "Conjugation and radiolabeling of monoclonal antibodies with zirconium-89 for PET imaging using the bifunctional chelate p-isothiocyanatobenzyl-desferrioxamine", Nature Protocols, 5(4):739-743.

Vugts et al. (2017) "Comparison of the octadentate bifunctional chelator DFO*-pPhe-NCS and the clinically used hexadentate bifunctional chelator DFO-pPhe-NCS for 89Zr-immuno-PET", European Journal of Nuclear Medicine and Molecular Imaging, doi:10.1007/s00259-016-3499-x, 44(2):286-295.

Waalboer et al. (2015) "Platinum (II) as Bifunctional Linker in Antibody-Drug Conjugate Formation: Coupling of a 4-Nitrobenzo-2-oxa-1,3-diazole Fluorophore to Trastuzumab as a Model", ChemMedChem, 10(5):797-803.

Walker et al. (2011) "LGR5 is a Negative Regulator of Tumourigenicity, Antagonizes Wnt Signalling and Regulates Cell Adhesion in Colorectal Cancer Cell Lines", PLoS One, 6(7):e22733.1-20.

Ward et al. (2013) "HDAC Inhibition Induces Increased Choline Uptake and Elevated Phosphocholine Levels in MCF7 Breast Cancer Cells", PLoS One, 8(4):e62610.1-11.

Wu et al. (2012) "Lgr5 is a potential marker of colorectal carcinoma stem cells that correlates with patient survival", World J Surg Oncol., 10(1):244.

Yamauchi et al. (2005) "The glypican 3 oncofetal protein is a promising diagnostic marker for hepatocellular carcinoma", Modern Pathology, 18(12):1591-1598.

Yang et al. (2014) "Imaging of hepatocellular carcinoma patient-derived xenografts using 89Zr-labeled anti-glypican-3 monoclonal antibody", Biomaterials, 35(25):6964-6971.

Yasumoto et al. (2004) "Epitope Mapping of the Melanosomal Matrix Protein gp100 (PMEL17) rapid processing in the endoplasmic reticulum and glycosylation in the early Golgi compartment", J Biol Chem, 279(27):28330-28338.

Yoon et al. (1998) "Antibodies to domains II and III of the IL-1 receptor accessory protein inhibit IL-1 beta activity but not binding: regulation of IL-1 responses is via type I receptor, not the accessory protein", J Immunol., 160 (7):3170-3179.

Zhai et al. (2015) "Novel Bifunctional Cyclic Chelator for (89)Zr Labeling-Radiolabeling and Targeting Properties of RGD Conjugates", Mol. Pharmaceutics, 12:2142-2150.

Zhu et al. (2013) "First-in-Man Phase I Study of GC33, a Novel Recombinant Humanized Antibody Against Glypican-3, in Patients with Advanced Hepatocellular Carcinoma", Clin Cancer Res., 19(4):920-928.

Slizys and Widnersson (2016) "The new "Pet" on the block: radio imaginig with Zirconium-89", FPA Patent Attorneys, 5 pages.

Rojko et al. (2014) "Formation, clearance, deposition, pathogenicity, and identification of biopharmaceutical-related immune complexes: review and case studies", Toxicol Pathol. 42(4):725-764.

GenBank Accession No. ACV51637.1, Hypothetical Protein Apar_1209 [Atopobium parvulum DSM 20469] (C8W847_ATOPD) Jun. 4, 2010 (retrieved online Jan. 16, 2015).

* cited by examiner

Characterization of H4H8314N-DFO

SEC: < 1% aggregate.

SDS-PAGE: similar motility profiles of PD-L1 parent and DFO conjugate 1. ladder
2. PD-L1 (L5)  NonRed
3. PD-L1-DFO (L19) NonRed
4. Skip
5. PD-L1 (L5)  Reduced
6. PD-L1-DFO (L19) Reduced 2 µg sample/lane.
Novex 4 – 20% Tris-Glycine Gel;
200V, 300 mA, 60min.

RADIOLABELED ANTI-PD-L1 ANTIBODIES FOR IMMUNO-PET IMAGING

CROSS-REFERENCE TO RELATED APPLICATIONS

This application claims the benefit under 34 U.S.C. § 119(e) of U.S. Provisional Application No. 62/428,672, filed Dec. 1, 2016, U.S. Provisional Application No. 62/457,267, filed Feb. 10, 2017, and U.S. Provisional Application No. 62/569,773, filed Oct. 9, 2017, all of which are herein specifically incorporated by reference in their entireties.

FIELD

This disclosure relates to radiolabeled anti-PD-L1 antibodies and their use in immuno-PET imaging.

SEQUENCE LISTING

An official copy of the sequence listing is submitted concurrently with the specification electronically via EFS-Web as an ASCII formatted sequence listing with a file name of "10305US01_Sequence_Listing_ST25.txt", a creation date of Dec. 1, 2017, and a size of about 117 KB. The sequence listing contained in this ASCII formatted document is part of the specification and is herein incorporated by reference in its entirety.

BACKGROUND

Programmed death-ligand 1 (PD-L1) (also called B7-H1 or CD274) is a 290 amino acid protein receptor ligand expressed widely on both lymphoid and non-lymphoid tissues such as CD4 and CD8 T-cells, macrophage lineage cells, peripheral tissues as well as on tumor cells, and virally-infected cells (Dong et al 1999, Nature Med.). PD-L1 binds to receptors PD-1 and B7-1 which belong to the CD28/CTLA-4 (cytotoxic T lymphocyte antigen)/ICOS (inducible co-stimulator) family of T-cell co-inhibitory receptors (Chen et al 2013, Nature Rev. Immunol. 13: 227-242) and attenuates the immune response by inhibiting T-cell activation. PD-L1 binding to PD-1 or B7-1 results in decreased T-cell proliferation and cytokine secretion, compromising humoral and cellular immune responses in diseases such as cancer, and viral infection. The expression of PD-L1 on tumor cells and virally-infected cells is exploited by tumors and chronic viral infections to evade immune response. PD-L1 is expressed on a wide variety of tumors and studies on animal models have shown that PD-L1 on tumors inhibits T-cell activation and lysis of tumor cells and may lead to increased death of tumor-specific T-cells. In chronic viral infections, PD-L1 expressed on virally-infected cells binds to PD-1 on virus-specific T-cells and these T-cells become "exhausted" with loss of effector functions and proliferative capacity (Freeman 2008, PNAS 105: 10275-10276). The PD-1: PD-L1 system also plays an important role in induced T-regulatory (Treg) cell development and in sustaining Treg function (Francisco et al 2010, Immunol. Rev. 236: 219-242). Blocking PD-L1 with antagonists, including monoclonal antibodies, has been studied in treatments of cancer and chronic viral infections (Ribas 2012, NEJM 366: 2517-2519; Freeman 2008, PNAS 105: 10275-10276; Sheridan 2012, Nature Biotechnology 30: 729-730).

Immuno-positron emission tomography (PET) is a diagnostic imaging tool that utilizes monoclonal antibodies labeled with positron emitters, combining the targeting properties of an antibody with the sensitivity of positron emission tomography cameras. See, e.g., *The Oncologist*, 12: 1379 (2007); *Journal of Nuclear Medicine*, 52(8): 1171 (2011). Immuno-PET enables the visualization and quantification of antigen and antibody accumulation in vivo and, as such, can serve as an important tool for diagnostics and complementing therapy. For example, immuno-PET can aid in the selection of potential patient candidates for a particular therapy, as well as in the monitoring of treatment.

As both PD1 and PD-L1 have emerged as targets for immunotherapy, there is need for diagnostic tools for anti-PD1 and/or anti-PD-L1 therapy, including, inter alia, diagnostic tools that enable the detection of suitable patient candidates for said therapy.

BRIEF SUMMARY

Included in this disclosure are radiolabeled anti-PD-L1 antibody conjugates for use in immuno-PET imaging.

In one aspect, the conjugate comprises an anti-PD-L1 antibody or antigen-binding fragment thereof, a chelating moiety, and a positron emitter.

Provided herein are also processes for synthesizing said conjugates and synthetic intermediates useful for the same.

Provided herein are also methods of imaging a tissue that expresses PD-L1, the methods comprising administering a radiolabeled anti-PD-L1 antibody conjugate described herein to the tissue; and visualizing the PD-L1 expression by positron emission tomography (PET) imaging.

Provided herein are also methods for detecting PD-L1 in a tissue, the methods comprising administering a radiolabeled anti-PD-L1 antibody conjugate described herein to the tissue; and visualizing the PD-L1 expression by PET imaging. In one embodiment, the tissue is present in a human subject. In certain embodiments, the subject is a non-human mammal. In certain embodiments, the subject has a disease or disorder such as cancer, an inflammatory disease, or an infection.

In some aspects, the subject is administered a dose of 5 mg, or 10 mg, or 20 mg, of a radiolabeled anti-PD-L1 antibody conjugate.

Provided herein are also methods for identifying a patient to be suitable for anti-tumor therapy comprising an inhibitor of the PD-1/PD-L1 signaling axis, the methods comprising selecting a patient with a solid tumor, administering a radiolabeled antibody conjugate described herein, and visualizing the administered radiolabeled antibody conjugate in the tumor by PET imaging wherein presence of the radiolabeled antibody conjugate in the tumor identifies the patient as suitable for anti-tumor therapy comprising an inhibitor of the PD-1/PD-L1 signaling axis.

Provided herein are also methods of treating a tumor, the methods comprising selecting a subject with a solid tumor; determining that the solid tumor is PD-L1-positive; and administering an anti-tumor therapy to the subject in need thereof. In certain embodiments, the anti-tumor therapy comprises an inhibitor of the PD-1/PD-L1 signaling axis (e.g., an anti-PD-1 antibody or an anti-PD-L1 antibody). In certain embodiments, the subject is administered a radiolabeled antibody conjugate described herein, and localization of the radiolabeled antibody conjugate is imaged via positron emission tomography (PET) imaging to determine if the tumor is PD-L1-positive.

Provided herein are also methods for monitoring the efficacy of an anti-tumor therapy in a subject, wherein the methods comprise selecting a subject with a solid tumor wherein the subject is being treated with an anti-tumor therapy; administering a radiolabeled conjugate described herein to the subject; imaging the localization of the administered radiolabeled conjugate in the tumor by PET imaging; and determining tumor growth, wherein a decrease from the baseline in uptake of the conjugate or radiolabeled signal indicates tumor regression and efficacy of the anti-tumor therapy. In certain embodiments, the anti-tumor therapy comprises an inhibitor of the PD-1/PD-L1 signaling axis (e.g., an anti-PD-1 antibody).

Provided herein are also methods for predicting response of a patient to an anti-tumor therapy comprising an inhibitor of the PD-1/PD-L1 signaling axis, the methods comprising selecting a patient with a solid tumor; and determining if the tumor is PD-L1-positive, wherein if the tumor is PD-L1-positive it indicates a positive response of the patient to an anti-tumor therapy comprising an inhibitor of the PD-1/PD-L1 signaling axis. In certain embodiments, the tumor is determined positive by administering a radiolabeled antibody conjugate of the present disclosure and localizing the radiolabeled antibody conjugate in the tumor by PET imaging wherein presence of the radiolabeled antibody conjugate in the tumor indicates that the tumor is PD-L1-positive.

DETAILED DESCRIPTION

I. Definitions

Figure 1B:
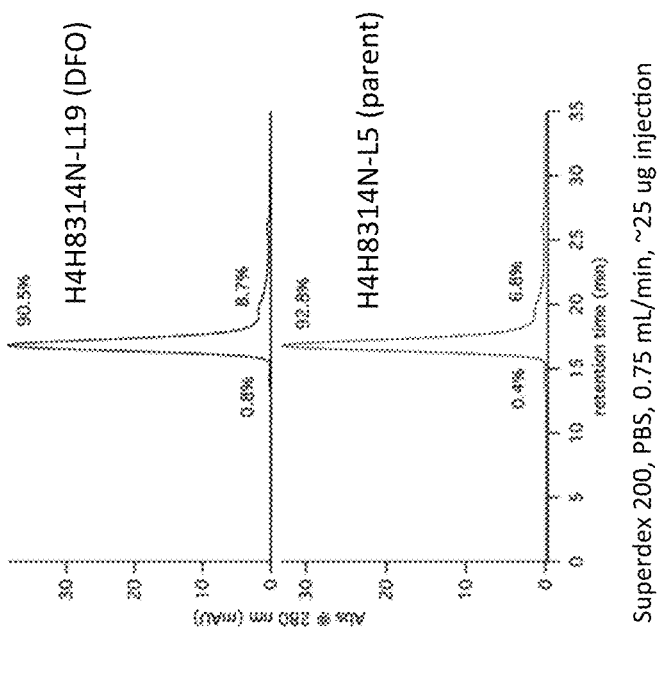
FIG. 1A depicts SDS-PAGE and FIG. 1B depicts SEC of un-modified anti-PD-L1 antibody and anti-PD-L1 DFO modified antibody.

Unless defined otherwise herein, all technical and scientific terms used herein have the same meaning as commonly understood by one of ordinary skill in the art to which the disclosed subject matter belongs.

The term "PD-L1" refers to programmed death-ligand 1, also known as CD274 and B7H1. The amino acid sequence of full-length PD-L1 is provided in GenBank as accession number NP_054862.1. The term "PD-L1" also includes protein variants of PD-L1. The term "PD-L1" includes recombinant PD-L1 or a fragment thereof. The term also encompasses PD-L1 or a fragment thereof coupled to, for example, histidine tag, mouse or human Fc, or a signal sequence such as ROR1. For example, the term includes sequences comprising a mouse Fc (mIgG2a) or human Fc (hIgG1) at the C-terminal, coupled to amino acid residues 19-239 of full-length PD-L1 (NP_054862.1). Protein variants comprise a histidine tag at the C-terminal, coupled to amino acid residues 19-239 of NP_054862.1. Unless specified as being from a non-human species, the term "PD-L1" means human PD-L1. PD-L1 is a 290 amino acid protein with extracellular IgV-like and IgC-like domains (amino acids 19-239 of full length PD-L1), a transmembrane domain and an intracellular domain of approximately 30 amino acids. PD-L1 is constitutively expressed on many cells such as antigen presenting cells (e.g., dendritic cells, macrophages, and B-cells) and on hematopoietic and non-hematopoietic cells (e.g., vascular endothelial cells, pancreatic islets, and sites of immune privilege). PD-L1 is also expressed on a wide variety of tumors, and virally-infected cells and is a component of the immunosuppressive milieu (Ribas 2012, NEJM 366: 2517-2519). PD-L1 binds to one of two T-cell co-inhibitors PD-1 and B7-1.

The term "PD-1" refers to the programmed death-1 protein, a T-cell co-inhibitor, also known as CD279. The amino acid sequence of full-length PD-1 is provided in GenBank as accession number NP_005009.2. The term also encompasses PD-1 or a fragment thereof coupled to, for example, histidine tag, mouse or human Fc, or a signal sequence such as ROR1. For example, the term includes sequences comprising a mouse Fc (mIgG2a) or human Fc (hIgG1) at the C-terminal, coupled to amino acid residues 25-170 of NP_005009.2 with a C93S change. PD-1 is a member of the CD28/CTLA-4/ICOS family of T-cell co-inhibitors. PD-1 is a 288-amino acid protein with an extracellular N-terminal domain which is IgV-like, a transmembrane domain and an intracellular domain containing an immunoreceptor tyrosine-based inhibitory (ITIM) motif and an immunoreceptor tyrosine-based switch (ITSM) motif (Chattopadhyay et al 2009, Immunol. Rev.). The PD-1 receptor has two ligands, PD-L1 and PD-L2.

The term "B7-1" refers to the T-lymphocyte activation antigen, also known as costimulatory factor CD80. B7-1 is a 288 amino acid membrane receptor with an extracellular N-terminal domain which comprises IgV-like (aa 37-138) and IgC-like (aa 154-232) regions, a transmembrane domain (aa 243-263) and a C-terminal intracellular region (aa 263-288). The amino acid sequence of full-length B7-1 is provided in GenBank as accession number NP_005182.1.

As used herein, the term "T-cell co-inhibitor" refers to a ligand and/or receptor which modulates the immune response via T-cell activation or suppression. The term "T-cell co-inhibitor", also known as T-cell co-signaling molecule, includes, but is not limited to, PD-1, lymphocyte activation gene 3 protein (LAG-3, also known as CD223), cytotoxic T-lymphocyte antigen-4 (CTLA-4), B and T lymphocyte attenuator (BTLA), CD-28, 2B4, LY108, T-cell immunoglobulin and mucin-3 (TIM3), T-cell immunoreceptor with immunoglobulin and ITIM (TIGIT; also known as VSIG9), leucocyte associated immunoglobulin-like receptor 1 (LAIR1; also known as CD305), inducible T-cell costimulator (ICOS; also known as CD278), B7-1 (CD80), and CD160.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-PD-L1 monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure also includes fully human anti-PD-L1 monoclonal antibodies comprising variants of any of the HCVR, LCVR, and/or CDR amino acid sequences disclosed herein having one or more conservative substitutions. For example, the present disclosure includes anti-PD-L1 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The term "multi-specific antigen-binding molecules", as used herein refers to bispecific, tri-specific or multi-specific antigen-binding molecules, and antigen-binding fragments thereof. Multi-specific antigen-binding molecules may be specific for different epitopes of one target polypeptide or may contain antigen-binding domains specific for epitopes of more than one target polypeptide. A multi-specific antigen-binding molecule can be a single multifunctional polypeptide, or it can be a multimeric complex of two or more polypeptides that are covalently or non-covalently associated with one another. The term "multi-specific antigen-binding molecules" includes antibodies of the present disclosure that may be linked to or co-expressed with another functional molecule, e.g., another peptide or protein. For example, an antibody or fragment thereof can be functionally linked (e.g., by chemical coupling, genetic fusion, non-covalent association or otherwise) to one or more other molecular entities, such as a protein or fragment thereof to produce a bi-specific or a multi-specific antigen-binding molecule with a second binding specificity. According to the present disclosure, the term "multi-specific antigen-binding molecules" also includes bi-specific, tri-specific or multi-specific antibodies or antigen-binding fragments thereof. In certain embodiments, an antibody of the present disclosure is functionally linked to another antibody or antigen-binding fragment thereof to produce a bispecific antibody with a second binding specificity. Bispecific and multi-specific antibodies of the present disclosure are described elsewhere herein.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to PD-L1. Moreover, multi-specific antibodies that bind to one domain in PD-L1 and one or more additional antigens or a bi-specific that binds to two different regions of PD-L1 are nonetheless considered antibodies that "specifically bind", as used herein.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to PD-L1.

An "isolated antibody", as used herein, is intended to refer to an antibody that is substantially free of other antibodies (Abs) having different antigenic specificities (e.g., an isolated antibody that specifically binds PD-L1, or a fragment thereof, is substantially free of Abs that specifically bind antigens other than PD-L1.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains:

aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix. Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, in need of amelioration, prevention and/or treatment of a disease or disorder such as chronic viral infection, cancer or autoimmune disease.

II. Radiolabeled Immunoconjugates of PD-L1 Antibodies for Immuno-PET Imaging

Provided herein are radiolabeled antigen-binding proteins that bind programmed death-ligand 1 (PD-L1). In some embodiments, the radiolabeled antigen-binding proteins comprise an antigen-binding protein covalently linked to one or more chelating moieties, which are chemical moieties that are capable of chelating a positron emitter.

In some embodiments, provided herein are antigen-binding proteins that bind PD-L1, e.g., antibodies, wherein said antigen-binding proteins that bind PD-L1 are covalently bonded to one or more moieties having the following structure:

$$-L-M_Z$$

wherein L is a chelating moiety; M is a positron emitter; and z, independently at each occurrence, is 0 or 1; and wherein at least one of z is 1.

In some embodiments, the radiolabeled antigen-binding protein is a compound of Formula (I):

$$M-L-A-[L-M_Z]_k \quad (I)$$

A is a protein that binds PD-L1; L is a chelating moiety; M is a positron emitter; z is 0 or 1; and k is an integer from 0-30. In some embodiments, k is 1.

In certain embodiments, the radiolabeled antigen-binding protein is a compound of Formula (II):

$$A-[L-M]_k \quad (II)$$

wherein A is a protein that binds PD-L1; L is a chelating moiety; M is a positron emitter; and k is an integer from 1-30.

In some embodiments, provided herein are compositions comprising a conjugate having the following structure:

$$A-L_k$$

wherein A is a protein that binds PD-L1; L is a chelating moiety; and k is an integer from 1-30; wherein the conjugate is chelated with a positron emitter in an amount sufficient to provide a specific activity suitable for clinical PET imaging.

Suitable binding proteins, chelating moieties, and positron emitters are provided below.

A. PD-L1 Binding Proteins

Suitable PD-L1 binding protein are proteins that specifically bind to PD-L1, including those described in US Patent Publication No. US 2015-0203580 A1, incorporated herein by reference in its entirety. Exemplary anti-PD-L1 antibodies of the present disclosure are listed in Table 1 of US Patent Publication No. US 2015-0203580 A1, also presented below.

TABLE 1

| Antibody | Amino Acid Sequence Identifiers | | | | | | | |
|---|---|---|---|---|---|---|---|---|
| | SEQ ID NOs: | | | | | | | |
| Designation | HCVR | HCDR1 | HCDR2 | HCDR3 | LCVR | LCDR1 | LCDR2 | LCDR3 |
| H2M8306N | 2 | 4 | 6 | 8 | 10 | 12 | 14 | 16 |
| H2M8307N | 18 | 20 | 22 | 24 | 26 | 28 | 30 | 32 |
| H2M8309N | 34 | 36 | 38 | 40 | 42 | 44 | 46 | 48 |
| H2M8310N | 50 | 52 | 54 | 56 | 58 | 60 | 62 | 64 |
| H2M8312N | 66 | 68 | 70 | 72 | 74 | 76 | 78 | 80 |
| H2M8314N | 82 | 84 | 86 | 88 | 90 | 92 | 94 | 96 |
| H2M8316N | 98 | 100 | 102 | 104 | 106 | 108 | 110 | 112 |
| H2M8317N | 114 | 116 | 118 | 120 | 122 | 124 | 126 | 128 |

TABLE 1-continued

Amino Acid Sequence Identifiers

| Antibody Designation | SEQ ID NOs: HCVR | HCDR1 | HCDR2 | HCDR3 | LCVR | LCDR1 | LCDR2 | LCDR3 |
|---|---|---|---|---|---|---|---|---|
| H2M8321N | 130 | 132 | 134 | 136 | 138 | 140 | 142 | 144 |
| H2M8323N | 146 | 148 | 150 | 152 | 154 | 156 | 158 | 160 |
| H2M8718N | 162 | 164 | 166 | 168 | 170 | 172 | 174 | 176 |
| H2M8718N2 | 178 | 180 | 182 | 184 | 170 | 172 | 174 | 176 |
| H2M8719N | 186 | 188 | 190 | 192 | 194 | 196 | 198 | 200 |
| H1H9323P | 202 | 204 | 206 | 208 | 210 | 212 | 214 | 216 |
| H1H9327P | 218 | 220 | 222 | 224 | 226 | 228 | 230 | 232 |
| H1H9329P | 234 | 236 | 238 | 240 | 242 | 244 | 246 | 248 |
| H1H9336P | 250 | 252 | 254 | 256 | 258 | 260 | 262 | 264 |
| H1H9344P2 | 266 | 268 | 270 | 272 | 274 | 276 | 278 | 280 |
| H1H9345P2 | 282 | 284 | 286 | 288 | 274 | 276 | 278 | 280 |
| H1H9351P2 | 290 | 292 | 294 | 296 | 274 | 276 | 278 | 280 |
| H1H9354P2 | 298 | 300 | 302 | 304 | 274 | 276 | 278 | 280 |
| H1H9364P2 | 306 | 308 | 310 | 312 | 274 | 276 | 278 | 280 |
| H1H9373P2 | 314 | 316 | 318 | 320 | 274 | 276 | 278 | 280 |
| H1H9382P2 | 322 | 324 | 326 | 328 | 274 | 276 | 278 | 280 |
| H1H9387P2 | 330 | 332 | 334 | 336 | 274 | 276 | 278 | 280 |
| H1H9396P2 | 338 | 340 | 342 | 344 | 274 | 276 | 278 | 280 |

Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-PD-L1 antibodies.

In some embodiments, the binding protein is an antibody or antigen binding fragment comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

In some embodiments, the binding protein is an antibody or antigen binding fragment comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

In some embodiments, the binding protein is an antibody or antigen binding fragment comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present disclosure provides antibodies, or antigen-binding fragments thereof, comprising an HCVR/LCVR amino acid sequence pair contained within any of the exemplary anti-PD-L1 antibodies listed in Table 1. In certain embodiments, the HCVR/LCVR amino acid sequence pair is selected from the group consisting of SEQ ID NOs: 2/10, 18/26, 34/42, 50/58, 66/74, 82/90, 98/106, 114/122, 130/138, 146/154, 162/170, 178/170, 186/194, 202/210, 218/226, 234/242, 250/258, 266/274, 282/274, 290/274, 298/274, 306/274, 314/274, 322/274, 330/274, and 338/274. In certain embodiments, the HCVR/LCVR amino acid sequence pair is selected from one of SEQ ID NOs: 82/90 (e.g., H2M8314N), 162/170 (e.g., H2M8718N), 306/274 (e.g., H1H9364P2), and 314/274 (e.g., H1H9373P2). In certain other embodiments, the HCVR/LCVR amino acid sequence pair is selected from one of SEQ ID NOs: 98/106 (e.g., H2M8316N), 146/154 (e.g., H2M8323N), 290/274 (e.g., H1H9351P2), and 330/274 (e.g., H1H9387P2).

In some embodiments, the binding protein is an antibody or antigen binding fragment comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

In some embodiments, the binding protein is an antibody or antigen binding fragment comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present disclosure provides antibodies, or antigen-binding fragments thereof, comprising an HCDR3/LCDR3 amino acid sequence pair contained within any of the exemplary anti-PD-L1 antibodies listed in Table 1. In certain embodiments, the HCDR3/LCDR3 amino acid sequence pair is selected from the group consisting of SEQ ID NOs: 88/96 (e.g., H2M8314N), 168/176 (e.g., H2M8718N), 312/280 (e.g., H1H9364P2), and 320/280 (e.g., H1H9373P2). In certain other embodiments, the HCDR3/LCDR3 amino acid sequence pair is selected from the group consisting of SEQ ID NOs: 104/112 (e.g., H2M8316N), 152/160 (e.g., H2M8323N), 296/280 (e.g., H1H9351P2), and 336/280 (e.g., H1H9387P2).

In some embodiments, the binding protein is an antibody or antigen binding fragment comprising a set of six CDRs (i.e., HCDR1-HCDR2-HCDR3-LCDR1-LCDR2-LCDR3) contained within any of the exemplary anti-PD-L1 antibodies listed in Table 1. In certain embodiments, the HCDR1-HCDR2-HCDR3-LCDR1-LCDR2-LCDR3 amino acid sequence set is selected from the group consisting of SEQ ID NOs: 84-86-88-92-94-96 (e.g., H2M8314N); 164-166-168-172-174-176 (e.g., H2M8718N); 308-310-312-276-278-280 (e.g., H1H9364P2); and 316-318-320-276-278-280 (e.g., H1H9373P2). In certain other embodiments, the HCDR1-HCDR2-HCDR3-LCDR1-LCDR2-LCDR3 amino acid sequence set is selected from the group consisting of SEQ ID NOs: 100-102-104-108-110-112 (e.g., H2M8316N); 148-150-152-156-158-160 (e.g., H2M8323N); 292-294-296-276-278-280 (e.g., H1H9351P2); and 332-334-336-276-278-280 (e.g., H1H9387P2).

In some embodiments, the binding protein is an antibody or antigen binding fragment comprising a set of six CDRs (i.e., HCDR1-HCDR2-HCDR3-LCDR1-LCDR2-LCDR3) contained within an HCVR/LCVR amino acid sequence pair as defined by any of the exemplary anti-PD-L1 antibodies listed in Table 1. For example, in some embodiments, the binding protein is an antibody or antigen binding fragment comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 82/90 (e.g., H2M8314N), 98/106 (e.g., H2M8316N), 146/154 (e.g., H2M8323N), 162/170 (e.g., H2M8718N), 290/274 (e.g., H1H9351P2), 306/274 (e.g., H1H9364P2), 314/274 (e.g., H1H9373P2) and 330/274 (e.g., H1H9387P2). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., J. Mol. Biol. 273:927-948 (1997); and Martin et al., Proc. Natl. Acad. Sci. USA 86:9268-9272 (1989). Public databases are also available for identifying CDR sequences within an antibody.

In some embodiments, binding proteins are antibodies and antigen-binding fragments thereof that compete for specific binding to PD-L1 with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

In some embodiments, the binding proteins are isolated antibodies and antigen-binding fragments thereof that block PD-L1 binding to PD-1 or to B7-1. In some embodiments, the antibody or antigen-binding fragment thereof that blocks PD-L1 binding to PD-1 or to B7-1 may bind to the same epitope on PD-L1 as PD-1/B7-1 or may bind to a different epitope on PD-L1 as PD-1/B7-1. In certain embodiments, the antibodies of the disclosure that block PD-L1 binding to PD-1 or to B7-1 comprise the CDRs of an HCVR having an amino acid sequence selected from the group consisting of HCVR sequences listed in Table 1; and the CDRs of a LCVR having an amino acid sequence selected from the group consisting of LCVR sequences listed in Table 1.

In alternate embodiments, the present disclosure provides antibodies and antigen-binding fragments thereof that do not block PD-L1 binding to PD-1 or to B7-1. In certain embodiments, the present disclosure provides isolated antibodies or antigen-binding fragments thereof that bind PD-L1, wherein the antibodies or antigen-binding fragments thereof enhance PD-L1 binding to PD-1 or to B7-1. In some embodiments, the isolated antibodies or antigen-binding fragments thereof that enhance PD-L1 binding to PD-1/B7-1 comprise the CDRs of a HCVR, wherein the HCVR has an amino acid sequence selected from the group consisting of SEQ ID NOs: 18, 66, 114, 130, 202, 218, 266, 282, 298, 322 and 338; and the CDRs of a LCVR, wherein the LCVR has an amino acid sequence selected from the group consisting of SEQ ID NOs: 26, 74, 122, 138, 210, 226, and 274. In some embodiments, the isolated antibodies or antigen-binding fragments thereof comprise an HCVR/LCVR amino acid sequence pair selected from the group consisting of SEQ ID NOs: 18/26 (e.g., H2M8307N), 66/74 (e.g., H2M8312N), 114/122 (e.g., H2M8317N), 130/138 (e.g., H2M8321N), 202/210 (e.g., H1H9323P), 218/226 (e.g., H1H9327P), 266/274 (e.g., H1H9344P2), 282/274 (e.g., H1H9345P2), 298/274 (e.g., H1H9354P2), 322/274 (e.g., H1H9382P2), and 338/274 (e.g., H1H9396P2).

In some embodiments, the binding proteins are antibodies and antigen-binding fragments thereof that bind specifically to PD-L1 from human or other species. In certain embodiments, the antibodies may bind to human PD-L1 and/or to cynomolgus PD-L1.

In some embodiments, the binding proteins are antibodies and antigen-binding fragments thereof that cross-compete for binding to PD-L1 with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

In one embodiment, the binding protein is an isolated antibody or antigen-binding fragment that has one or more of the following characteristics: (a) blocks the binding of PD-L1 to PD-1 or to B7-1; (b) binds specifically to human PD-L1 and/or cynomolgus PD-L1; (c) inhibits T-cell proliferation in a mixed lymphocyte reaction (MLR) assay; and (d) increases IL-2 and/or interferon-gamma secretion in a MLR assay.

In some embodiments, the binding protein is an antibody or antigen binding fragment thereof may bind specifically to PD-L1 in an agonist manner, i.e., it enhances or stimulates PD-L1 binding and/or activity; in other embodiments, the antibody can bind specifically to PD-L1 in an antagonist manner, i.e., it blocks PD-L1 from binding to its receptor.

In certain embodiments, the antibodies or antigen-binding fragments are bispecific comprising a first binding specificity to PD-L1 and a second binding specificity for a second target epitope. The second target epitope may be another epitope on PD-L1 or on a different protein such as a T-cell co-inhibitor. In certain embodiments, the target epitope may be on a different cell including e.g., a different T-cell, a B-cell, a tumor cell, an autoimmune tissue cell or a virally infected cell.

In some embodiments, the antibodies and antigen-binding fragments of antibodies bind monomeric PD-L1 (e.g., at 25° C. or at 37° C.) with a $K_D$ of less than about 318 pM as measured by surface plasmon resonance, e.g., using the assay format as defined in Example 3 of US Patent Publication No. US 2015-0203580 A1, or substantially similar assay. In certain embodiments, the antibodies or antigen-binding fragments thereof bind monomeric PD-L1 with a $K_D$ of less than about 300 pM, less than about 250 pM, less than about 150 pM, less than about 100 pM, or less than about 50 pM, as measured by surface plasmon resonance, e.g., using the assay format as defined in Example 3 of US Patent Publication No. US 2015-0203580 A1, or a substantially similar assay.

In some embodiments, the antibodies and antigen-binding fragments thereof bind dimeric PD-L1 (e.g., at 25° C. or at 37° C.) with a $K_D$ of less than about 15 pM as measured by surface plasmon resonance, e.g., using the assay format as defined in Example 3 of US Patent Publication No. US 2015-0203580 A1 or sustainably similar assay. In certain embodiments, the antibodies or antigen-binding fragments thereof bind dimeric PD-L1 with a $K_D$ of less than about 12 pM, less than about 10 pM, less than about 8 pM, or less than about 5 pM, as measured by surface plasmon resonance, e.g., using the assay format as defined in Example 3 of US Patent Publication No. US 2015-0203580 A1, or a substantially similar assay.

In some embodiments, the antibodies or antigen-binding fragments thereof bind cynomolgus (*Macaca fascicularis*) PD-L1 (e.g., at 25° C. or at 37° C.) with a $K_D$ of less than about 28 nM as measured by surface plasmon resonance, e.g., using the assay format as defined in Example 3 of US Patent Publication No. US 2015-0203580 A1. In certain embodiments, the antibodies or antigen-binding fragments thereof bind cynomolgus PD-L1 with a $K_D$ of less than about 25 nM, less than about 20 nM, less than about 15 nM, less than about 10 nM, or less than about 5 nM, as measured by surface plasmon resonance, e.g., using the assay format as defined in Example 3 of US Patent Publication No. US 2015-0203580 A1, or a substantially similar assay.

In some embodiments, the antibodies and antigen-binding fragments thereof bind PD-L1 with a dissociative half-life (t½) of greater than about 1 minute as measured by surface plasmon resonance at 25° C. or 37° C., e.g., using an assay format as defined in Example 3 of US Patent Publication No. US 2015-0203580 A1, or a substantially similar assay. In certain embodiments, the antibodies or antigen-binding fragments bind PD-L1 with a t½ of greater than about 5 minutes, greater than about 10 minutes, greater than about 30 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, or greater than about 800 minutes, as measured by surface plasmon resonance at 25° C. or 37° C., e.g., using an assay format as defined in Example 3 of US Patent Publication No. US 2015-0203580 A1 (e.g., mAb-capture or antigen-capture format), or a substantially similar assay.

In some embodiments, the antibodies or antigen-binding fragments thereof block PD-L1 binding to PD-1 with an $IC_{50}$ of less than about 770 pM as determined using a ELISA-based immunoassay assay, e.g., as shown in Example 4 of US Patent Publication No. US 2015-0203580 A1, or a substantially similar assay. In some embodiments, the antibodies or antigen-binding fragments thereof block PD-L1 binding to B7-1 with an $IC_{50}$ of less than about 10 nM as determined using a ELISA-based immunoassay assay, e.g., as shown in Example 4 of US Patent Publication No. US 2015-0203580 A1, or a substantially similar assay. In some embodiments, the antibodies and antigen-binding fragments thereof bind to PD-L1 and enhance the binding of PD-L1 to PD-1 or to B7-1.

In some embodiments, the antibodies bind to the extracellular domain of PD-L1 or to a fragment of the domain. In some embodiments, the antibodies bind to more than one domain (cross-reactive antibodies). In certain embodiments, the antibodies of the bind to an epitope located in the extracellular domain comprising amino acid residues 19-239 of NP_054862.1.

In certain embodiments, the antibodies function by blocking or inhibiting the PD-1-binding or the B7-1-binding activity associated with PD-L1 by binding to any other region or fragment of the full length protein. In certain embodiments, the antibodies attenuate or modulate the interaction between PD-L1 and PD-1/B7-1.

In certain embodiments, the antibodies are bi-specific antibodies. The bi-specific antibodies can bind one epitope in one domain and can also bind a second epitope in a different domain of PD-L1. In certain embodiments, the bi-specific antibodies bind two different epitopes in the same domain. In one embodiment, the multi-specific antigen-binding molecule comprises a first antigen-binding specificity wherein the first binding specificity comprises the extracellular domain or fragment thereof of PD-1; and a second antigen-binding specificity to another epitope of PD-L1. In another embodiment, the multi-specific antigen-binding molecule comprises a first antigen-binding specificity wherein the first binding specificity comprises the extracellular domain or fragment thereof of B7-1; and a second antigen-binding specificity to another epitope of PD-L1.

In one embodiment, the antibody or fragment thereof is a fully human monoclonal antibody or antigen-binding fragment thereof that binds to PD-L1, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 186, 202, 218, 234, 250, 258, 266, 274, 282, 290, 298, 306, 314, 322, 330 and 338, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 194, 210, 226, 242, 258, and 274, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 192, 208, 224, 240, 256, 272, 280, 288, 296, 304, 312, 320, 328, 336 and 344, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 200, 216, 232, 248, 264, and 280, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 188, 204, 220, 236, 252, 268, 284, 292, 300, 308, 316, 324, 332, and 340, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 190, 206, 222, 238, 254, 270, 286, 294, 302, 310, 318, 326, 334, and 342, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 196, 212, 228, 244, 260, and 276, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 198, 214, 230, 246, 262, and 278, or a substantially similar sequence thereof having at least 90%, at least 95%, at least 98% or at least 99% sequence identity; (v) is a multi-specific antigen-binding molecule comprising a first binding specificity to PD-L1 and a second binding specificity to an antigen selected from the group consisting of PD-L1, a tumor specific antigen, a virally infected cell antigen, and a T-cell co-inhibitor; (vi) binds to human PD-L1 with a $K_D$ of about 4 pM to about 645 nM; (vii) binds to cynomolgus PD-L1 with a $K_D$ of about 70 pM to about 400 nM; (viii) blocks or enhances the binding of PD-L1 to PD-1 with an IC50≤770 pM; (ix) blocks or enhances the binding of PD-L1 to B7-1 with an IC50≤10 nM; (x) blocks PD-1-induced T-cell down-regulation and/or rescues T-cell signaling in a T-cell/APC luciferase reporter assay; (xi) stimulates T-cell proliferation and activity in a mixed lymphocyte reaction (MLR) assay; (xii) induces IL-2 and/or IFNγ production in a MLR assay; and (xiii) suppresses tumor growth and increases survival in subjects with cancer.

In one embodiment, the antibody or fragment thereof is a fully human monoclonal antibody or antigen-binding fragment thereof that blocks PD-L1 binding to PD-1 or to B7-1, wherein the antibody or fragment thereof exhibits one or more of the following characteristics: (i) comprises a HCVR having an amino acid sequence selected from the group consisting of SEQ ID NO: 82, 98, 146, 162, 290, 306, 314, and 330, or a substantially similar sequence thereof having at least 90%, at least 95%, at least 98% or at least 99% sequence identity; (ii) comprises a LCVR having an amino acid sequence selected from the group consisting of SEQ ID NO: 90, 106, 154, 170, and 274, or a substantially similar sequence thereof having at least 90%, at least 95%, at least 98% or at least 99% sequence identity; (iii) comprises a HCDR3 domain having an amino acid sequence selected from the group consisting of SEQ ID NO: 88, 104, 152, 168, 296, 312, 320, and 336, or a substantially similar sequence thereof having at least 90%, at least 95%, at least 98% or at least 99% sequence identity; and a LCDR3 domain having an amino acid sequence selected from the group consisting of SEQ ID NO: 96, 112, 160, 176, and 280, or a substantially similar sequence thereof having at least 90%, at least 95%, at least 98% or at least 99% sequence identity; (iv) comprises a HCDR1 domain having an amino acid sequence selected from the group consisting of SEQ ID NO: 84, 100, 148, 164, 292, 308, 316, and 332, or a substantially similar sequence thereof having at least 90%, at least 95%, at least 98% or at least 99% sequence identity; a HCDR2 domain having an amino acid sequence selected from the group consisting of SEQ ID NO: 86, 102, 150, 166, 294, 310, 318, and 334, or a substantially similar sequence thereof having at least 90%, at least 95%, at least 98% or at least 99% sequence identity; a LCDR1 domain having an amino acid sequence selected from the group consisting of SEQ ID NO: 92, 108, 156, 172, and 276, or a substantially similar sequence thereof having at least 90%, at least 95%, at least 98% or at least 99% sequence identity; and a LCDR2 domain having an amino acid sequence selected from the group consisting of SEQ ID NO: 94, 110, 158, 174, and 278, or a substantially similar sequence thereof having at least 90%, at least 95%, at least 98% or at least 99% sequence identity; (v) is a multi-specific antigen-binding molecule comprising a first binding specificity to PD-L1 and a second binding specificity to an antigen selected from the group consisting of a different epitope of PD-L1, a tumor specific antigen, a virally-infected cell antigen, and a T-cell co-inhibitor; (vi) binds to human PD-L1 with a $K_D \leq 10^{-10}$M; (vii) binds to cynomolgus PD-L1 with a $K_D \leq 10^{-7}$M; (viii) blocks the binding of PD-L1 to PD-1 or to B7-1; (ix) blocks PD-1-induced T-cell down-regulation and/or rescues T-cell signaling in a T-cell/APC luciferase reporter assay; (xi) stimulates T-cell proliferation and activity in a mixed lymphocyte reaction (MLR) assay; (xii) induces IL-2 and/or IFNγ production in a MLR assay; and (xiii) suppresses tumor growth and increases survival in subjects with cancer.

In certain embodiments, the anti-PD-L1 antibodies or antigen-binding fragments thereof bind an epitope within any one or more of the regions exemplified in PD-L1, either in natural form, or recombinantly produced, or to a fragment thereof. In some embodiments, the antibodies of the disclosure bind to an extracellular region comprising one or more amino acids selected from the group consisting of amino acid residues 19-239 of PD-L1. In some embodiments, the antibodies of the disclosure bind to a region comprising one or more amino acids selected from the group consisting of amino acid residues 1-221 of cynomolgus PD-L1.

In certain embodiments, the antibodies of the disclosure, as shown in Table 1, interact with at least one amino acid sequence selected from the group consisting of amino acid residues ranging from about position 19 to about position 130 of PD-L1; or amino acid residues ranging from about position 130 to about position 153 of PD-L1; or amino acid residues ranging from about position 153 to about position 210 of PD-L1; or to amino acid residues ranging from about position 210 to about position 239 of PD-L1.

In some embodiments, the anti-PD-L1 antibodies bind to the same epitope, or a portion of the epitope, as any of the specific exemplary antibodies described herein in Table 1, or an antibody having the CDR sequences of any of the exemplary antibodies described in Table 1. Likewise, suitable antibodies also include anti-PD-L1 antibodies that compete for binding to PD-L1 or a PD-L1 fragment with any of the specific exemplary antibodies described herein in Table 1, or an antibody having the CDR sequences of any of the exemplary antibodies described in Table 1. For example, suitable antibodies include anti-PD-L1 antibodies that cross-compete for binding to PD-L1 with one or more antibodies as defined in Example 6 of herein (e.g., H2aM8309N, H1H9329P, H1H9336P, H2aM8314N, H2aM8316N, H2AM8718N, H1H9387P2, H1H9351P2, H1H9364P2, H1H9373P2, and H2aM8306N). The present disclosure also includes anti-PD-L1 antibodies that cross-compete for binding to PD-L1 with one or more antibodies as defined in Example 6 of US Patent Publication No. US 2015-0203580 A1 (e.g., H1H9396P2, H2aM8317N, H2aM8321N, H1H9323P, H1H9382P2, H1H9344P2, H1H9345P2 and H1H9354P2).

The antibodies and antigen-binding fragments described herein specifically bind to PD-L1 and modulate the interaction of PD-L1 with PD-1 or with B7-1. The anti-PD-L1 antibodies may bind to PD-L1 with high affinity or with low affinity. In certain embodiments, the antibodies are blocking antibodies wherein the antibodies bind to PD-L1 and block the interaction of PD-L1 with PD-1 or with B7-1. In some embodiments, the blocking antibodies of the disclosure block the binding of PD-L1 to PD-1 or to B7-1 and/or stimulate or enhance T-cell activation. In some embodiments, the blocking antibodies are useful for stimulating or enhancing the immune response and/or for treating a subject suffering from cancer, or a chronic viral infection. The antibodies when administered to a subject in need thereof may reduce the chronic infection by a virus such as HIV, LCMV or HBV in the subject. They may be used to inhibit the growth of tumor cells in a subject. They may be used alone or as adjunct therapy with other therapeutic moieties or modalities known in the art for treating cancer, or viral infection. In certain embodiments, the anti-PD-L1 antibodies that bind to PD-L1 with a low affinity are used as multi-specific antigen-binding molecules wherein the first binding specificity binds to PD-L1 with a low affinity and the second binding specificity binds to an antigen selected from the group consisting of a different epitope of PD-L1, a T-cell co-inhibitor such as PD-1, a tumor specific antigen and an infected-cell-specific antigen.

In certain embodiments, the antibodies of the present disclosure are agonist antibodies, wherein the antibodies bind to PD-L1 and enhance the interaction of PD-L1 and PD-1/B7-1. In some embodiments, the activating antibodies enhance binding of PD-L1 to PD-1 or to B7-1 and/or inhibit or suppress T-cell activation. The activating antibodies of the present disclosure may be useful for inhibiting the immune response in a subject and/or for treating autoimmune disease.

In certain embodiments, the anti-PD-L1 antibodies are multi-specific antigen-binding molecules, wherein they comprise a first binding specificity to PD-L1 and a second binding specificity to an antigen selected from the group consisting of a different epitope of PD-L1, a T-cell co-inhibitor such as PD-1, a tumor specific antigen and an infected-cell-specific antigen. In certain embodiments, the first binding specificity binds to PD-L1 with low affinity, e.g., with a $K_D$ of $10^{-8}$ M, $10^{-7}$ M or more.

Certain anti-PD-L1 antibodies of the present disclosure are able to bind to and neutralize the activity of PD-L1, as determined by in vitro or in vivo assays. The ability of the antibodies of the disclosure to bind to and neutralize the activity of PD-L1 may be measured using any standard method known to those skilled in the art, including binding assays, or activity assays, as described herein.

Non-limiting, exemplary in vitro assays for measuring binding activity are illustrated in Example 3 of US Patent Publication No. US 2015-0203580 A1. In Example 3, the binding affinities and kinetic constants of human anti-PD-L1 antibodies for human PD-L1 and cynomolgus PD-L1 were determined by surface plasmon resonance and the measurements were conducted on a T200 Biacore instrument. In Examples 4 and 5 of US Patent Publication No. US 2015-0203580 A1, blocking assays were used to determine the ability of the anti-PD-L1 antibodies to block PD-L1-binding ability of PD-1 or to B7-1 in vitro. In Example 6 of US Patent Publication No. US 2015-0203580 A1, blocking assays were used to determine cross-competition between different anti-PD-L1 antibodies. Example 7 of US Patent Publication No. US 2015-0203580 A1 describes the binding of the antibodies to cells overexpressing PD-L1. In Example 8 of US 2015-0203580 A1, a luciferase assay was used to determine the ability of anti-PD-L1 antibodies to antagonize PD-1/PD-L1 signaling in T-cells.

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to PD-L1. An antibody fragment may include a Fab fragment, a $F(ab')_2$ fragment, a Fv fragment, a dAb fragment, a fragment containing a CDR, or an isolated CDR. In certain embodiments, the term "antigen-binding fragment" refers to a polypeptide or fragment thereof of a multi-specific antigen-binding molecule. In such embodiments, the term "antigen-binding fragment" includes, e.g., an extracellular domain of PD-1 which binds specifically to PD-L1. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present disclosure using routine techniques available in the art.

The anti-PD-L1 antibodies and antibody fragments of the present disclosure encompass proteins having amino acid sequences that vary from those of the described antibodies, but that retain the ability to bind PD-L1. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present disclosure encompass sequences that comprise one or more additions, deletions, or substitutions of nucleotides when compared to the disclosed sequence, but that encode an antibody or antibody fragment that is essentially bioequivalent to an antibody or antibody fragment of the disclosure.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

According to certain embodiments of the present disclosure, anti-PD-L1 antibodies comprise an Fc domain comprising one or more mutations which enhance or diminish antibody binding to the FcRn receptor, e.g., at acidic pH as compared to neutral pH. For example, the present disclosure includes anti-PD-L1 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present disclosure includes anti-PD-L1 antibodies comprising an Fc domain comprising one or more pairs or groups of mutations selected from the group consisting of: 250Q and 248L (e.g., T250Q and M248L); 252Y, 254T and 256E (e.g., M252Y, 5254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). In one embodiment, the present disclosure includes anti-PD-L1 antibodies comprising an Fc domain comprising a S108P mutation in the hinge region of IgG4 to promote dimer stabilization. All possible combinations of the foregoing Fc domain mutations, and other mutations within the antibody variable domains disclosed herein, are contemplated within the scope of the present disclosure.

The present disclosure also includes anti-PD-L1 antibodies comprising a chimeric heavy chain constant ($C_H$) region, wherein the chimeric $C_H$ region comprises segments derived from the $C_H$ regions of more than one immunoglobulin isotype. For example, the antibodies of the disclosure may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the disclosure comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Ser. No. 14/170,166, filed Jan. 31, 2014, the disclosure of which is hereby incorporated by reference in its entirety).

B. Positron Emitters and Chelating Moieties

Suitable positron emitters include, but are not limited to, those that form stable complexes with the chelating moiety and have physical half-lives suitable for immuno-PET imaging purposes. Illustrative positron emitters include, but are not limited to, $^{89}$Zr, $^{68}$Ga, $^{64}$Cu, $^{44}$Sc, and $^{86}$Y. Suitable positron emitters also include those that directly bond with the PD-L1 binding protein, including, but not limited to, $^{76}$Br and $^{124}$I, and those that are introduced via prosthetic group, e.g., $^{18}$F, The chelating moieties described herein are chemical moieties that are covalently linked to the PD-L1 binding protein, e.g., anti-PD-L1 antibody and comprise a portion capable of chelating a positron emitter, i.e., capable of reacting with a positron emitter to form a coordinated chelate complex. Suitable moieties include those that allow efficient loading of the particular metal and form metal-chelator complexes that are sufficiently stable in vivo for diagnostic uses, e.g., immuno-PET imaging. Illustrative chelating moieties include those that minimize dissociation of the positron emitter and accumulation in mineral bone, plasma proteins, and/or bone marrow depositing to an extent suitable for diagnostic uses.

Examples of chelating moieties include, but are not limited to, those that form stable complexes with positron emitters $^{89}$Zr, $^{68}$Ga, $^{64}$Cu, $^{44}$Sc, and/or $^{86}$Y. Illustrative chelating moieties include, but are not limited to, those described in Nature Protocols, 5(4): 739, 2010; *Bioconjugate Chem.*, 26(12): 2579 (2015); *Chem Commun (Camb)*, 51(12): 2301 (2015); *Mol. Pharmaceutics*, 12: 2142 (2015); *Mol. Imaging Biol.*, 18: 344 (2015); *Eur. J. Nucl. Med. Mol. Imaging*, 37:250 (2010); *Eur. J. Nucl. Med. Mol. Imaging* (2016). doi:10.1007/s00259-016-3499-x; Bioconjugate Chem., 26(12): 2579 (2015); WO 2015/140212A1; and U.S. Pat. No. 5,639,879, incorporated by reference in their entireties.

Illustrative chelating moieties also include, but are not limited to, those that comprise desferrioxamine (DFO), 1,4,7,10-tetraacetic acid (DOTA), diethylenetriaminepentaacetic acid (DTPA), ethylenediaminetetraacetic acid (EDTA), (1,4,7,10-Tetraazacyclododecane-1,4,7,10-tetra (methylene phosphonic) acid (DOTP), 1R, 4R, 7R, 10R)-□'□"□'"-Tetramethyl-1,4,7,10-tetraazacyclododecane-1,4, 7,10-tetraacetic acid (DOTMA), 1,4,8,11-Tetraazacyclotetradecane-1,4,8,11-tetraacetic acid (TETA), H$_4$octapa, H$_6$phospa, H$_2$dedpa, H$_5$decapa, H$_2$azapa, HOPO, DO2A, 1,4,7,10-Tetrakis(carbamoylmethyl)-1,4,7,10-tetraazacyclododecane (DOTAM), 1,4,7-triazacyclononane-N, N',N"-triacetic acid (NOTA), 1,4,7,10-Tetrakis(carbamoylmethyl)-1,4,7,10-tetraazacyclododecane (DOTAM), 1,4,8, 11-tetraazabicyclo[6.6.2]hexadecane-4,11-dicetic acid (CB-TE2A), 1,4,7,10-Tetraazacyclododecane (Cyclen), 1,4,8,11-Tetraazacyclotetradecane (Cyclam), octadentate chelators, hexadentate chelators, phosphonate-based chelators, macrocyclic chelators, chelators comprising macrocyclic terephthalamide ligands, bifunctional chelators, fusarinine C and fusarinine C derivative chelators, triacetylfusarinine C (TAFC), ferrioxamine E (FOXE), ferrioxamine B (FOXB), ferrichrome A (FCHA), and the like.

In some embodiments, the chelating moieties are covalently bonded to the PD-L1 binding protein, e.g., antibody or antigen binding fragment thereof, via a linker moiety, which covalently attaches the chelating portion of the chelating moiety to the binding protein. In some embodiments, these linker moieties are formed from a reaction between a reactive moiety of the PD-L1 binding protein, e.g., cysteine or lysine of an antibody, and reactive moiety that is attached to a chelator, including, for example, a p-isothiocyanatobenyl group and the reactive moieties provided in the conjugation methods below. In addition, such linker moieties optionally comprise chemical groups used for purposes of adjusting polarity, solubility, steric interactions, rigidity, and/or the length between the chelating portion and PD-L1 binding protein.

C. Preparation of Radiolabeled Anti-PD-L1 Conjugates

The radiolabeled anti-PD-L1 protein conjugates can be prepared by (1) reacting a PD-L1 binding protein, e.g., antibody, with a molecule comprising a positron emitter chelator and a moiety reactive to the desirable conjugation site of the PD-L1 binding protein and (2) loading the desirable positron emitter.

Suitable conjugation sites include, but are not limited to, lysine and cysteine, both of which can be, for example, native or engineered, and can be, for example, present on the heavy or light chain of an antibody. Cysteine conjugation sites include, but are not limited to, those obtained from mutation, insertion, or reduction of antibody disulfide bonds. Methods for making cysteine engineered antibodies include, but are not limited to, those disclosed in WO2011/056983. Site-specific conjugation methods can also be used to direct the conjugation reaction to specific sites of an antibody, achieve desirable stoichiometry, and/or achieve desirable drug-to-antibody (DAR) ratios. Such conjugation methods are known to those of ordinary skill in the art and include, but are not limited to cysteine engineering and enzymatic and chemo-enzymatic methods, including, but not limited to, glutamine conjugation, Q295 conjugation, and transglutaminase-mediated conjugation, as well as those described in *J. Clin. Immunol.*, 36: 100 (2016), incorporated herein by reference in its entirety. Suitable moieties reactive to the desirable conjugation site generally enable efficient and facile coupling of the PD-L1 binding protein, e.g., antibody and positron emitter chelator. Moieties reactive to lysine and cysteine sites include electrophilic groups, which are known to those of ordinary skill. In certain aspects, when the desired conjugation site is lysine, the reactive moiety is an isothiocyanate, e.g., p-isothiocyanatobenyl group or reactive ester. In certain aspects, when the desired conjugation site is cysteine, the reactive moiety is a maleimide.

When the chelator is desferrioxamine (DFO), suitable reactive moieties include, but are not limited to, an isothiocyantatobenzyl group, an n-hydroxysuccinimide ester,2,3,5,6 tetraflurorphenol ester, n-succinimidyl-S-acetylthioacetate, and those described in *BioMed Research International*, Vol 2014, Article ID 203601, incorporated herein by reference in its entirety. In certain embodiments, the PD-L1 binding protein is an antibody and the molecule comprising a positron emitter chelator and moiety reactive to the conjugation site is p-isothiocyantatobenzyl-desferrioxamine (p-SCN-Bn-DFO):

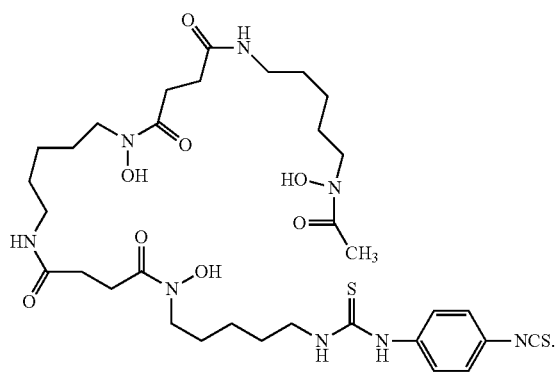

Positron emitter loading is accomplished by incubating the PD-L1 binding protein chelator conjugate with the positron emitter for a time sufficient to allow coordination of said positron emitter to the chelator, e.g., by performing the methods described in the examples provided herein, or substantially similar method.

D. Illustrative Embodiments of Conjugates

Included in the instant disclosure are radiolabeled antibody conjugates comprising an antibody or antigen binding fragment thereof, that binds human program death ligand 1 (PD-L1), a chelating moiety, and a positron emitter.

In some embodiments, the chelating moiety comprises a chelator capable of forming a complex with $^{89}$Zr. In certain embodiments, the chelating moiety comprises desferrioxamine. In certain embodiments, the chelating moiety is p-isothiocyanatobenzyl-desferrioxamine.

In some embodiments, the positron emitter is $^{89}$Zr.

In some embodiments, the chelating moiety-to-antibody ratio of the conjugate is from 1 to 2.

In a particular embodiment, chelating moiety is p-isothiocyanatobenzyl-desferrioxamine and the positron emitter is $^{89}$Zr. In another particular embodiment, the chelating moiety is p-isothiocyanatobenzyl-desferrioxamine and the positron emitter is $^{89}$Zr, and the chelating moiety-to-antibody ratio of the conjugate is from 1 to 2.

In some embodiments, provided herein are antigen-binding proteins that bind PD-L1, wherein said antigen-binding proteins that bind PD-L1 are covalently bonded to one or more moieties having the following structure:

-L-M$_Z$ wherein L is a chelating moiety; M is a positron emitter; and z, independently at each occurrence, is 0 or 1; and wherein at least one of z is 1. In certain embodiments, the radiolabeled antigen-binding protein is a compound of Formula (I):

M-L-A-[L-M$_Z$]$_k$ (I)

A is a protein that binds PD-L1; L is a chelating moiety; M is a positron emitter; z is 0 or 1; and k is an integer from 0-30. In some embodiments, k is 1.

In some embodiments, L is:

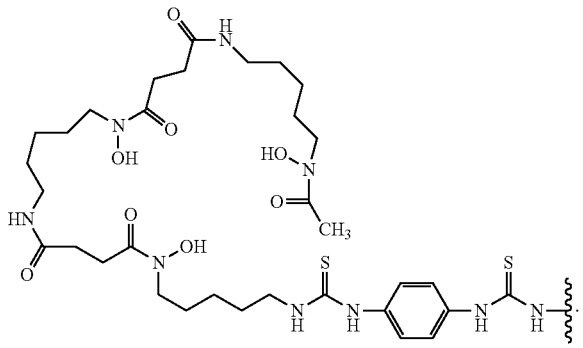 [SMILES: *NC(=S)Nc1ccc(NC(=S)NCCCCCN(O)C(=O)CCC(=O)NCCCCCN(O)C(=O)CCC(=O)NCCCCCN(O)C(C)=O)cc1]

In some embodiments, M is $^{89}$Zr.

In some embodiments, k is an integer from 1 to 2. In some embodiments, k is 1.

In some embodiments, -L-M is

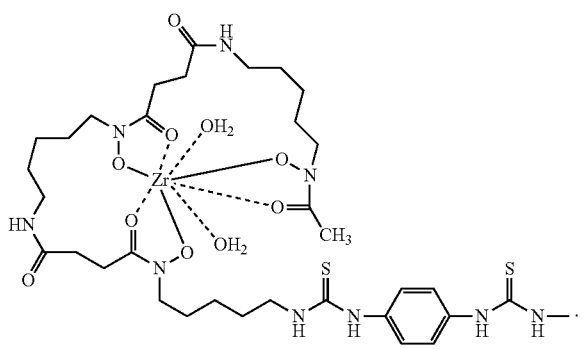

Included in the instant disclosure are also methods of synthesizing a radiolabeled antibody conjugates comprising contacting a compound of Formula (III):

(III)

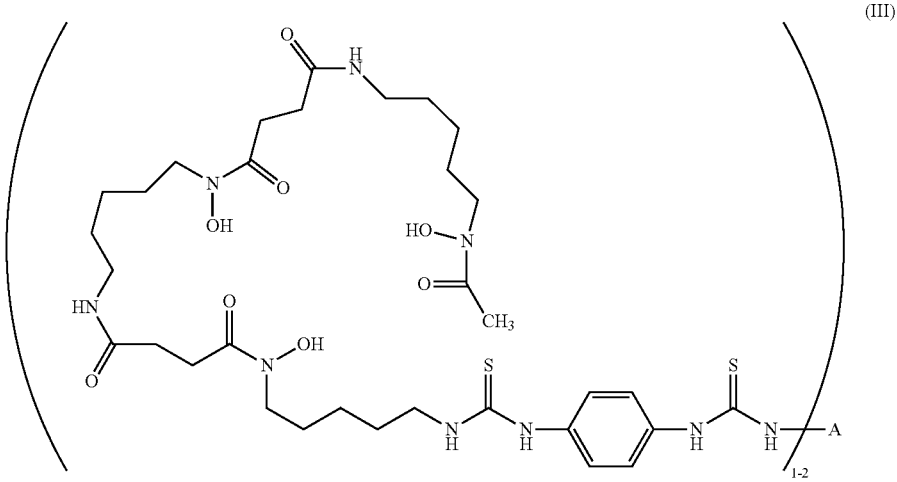

with $^{89}$Zr, wherein A is an antibody or antigen-binding fragment thereof that binds PD-L1. In certain embodiments, the compound of Formula (III) is synthesized by contacting an antibody, or antigen binding fragment thereof, that binds PD-L1, with p-SCN-Bn-DFO.

Provided herein is also the product of the reaction between a compound of Formula (III) with $^{89}$Zr.

Provided herein are compounds of Formula (III):

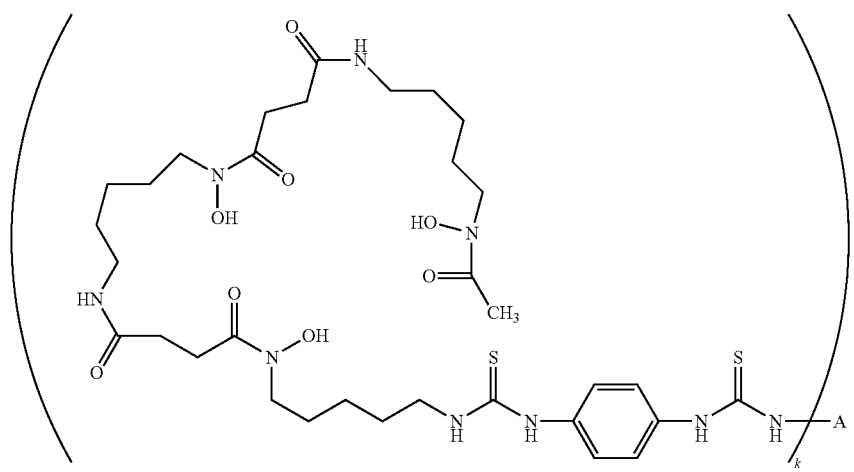

wherein A is an antibody or antigen binding fragment thereof that binds PD-L1 and k is an integer from 1-30. In some embodiments, k is 1 or 2.

In some embodiments, provided herein are compositions comprising a conjugate having the following structure:

A-L$_k$ wherein A is a protein that binds PD-L1; L is a chelating moiety; and k is an integer from 1-30; wherein the conjugate is chelated with a positron emitter in an amount sufficient to provide a specific activity suitable for clinical PET imaging. In some embodiments, the amount of chelated positron emitter is an amount sufficient to provide a specific activity of 1-3 mCi per 1-50 mg of the protein that binds PD-L1.

In some embodiments, the antibody or antigen-binding fragment thereof binds monomeric human programmed death-ligand 1 (PD-L1) with a binding dissociation equilibrium constant (K$_D$) of less than about 310 pM as measured in a surface plasmon resonance assay at 37° C.

In some embodiments, the antibody or antigen-binding fragment thereof binds monomeric human PD-L1 with a K$_D$ less than about 180 pM in a surface plasmon resonance assay at 25° C.

In some embodiments, the antibody or antigen-binding fragment thereof binds dimeric human PD-L1 with a K$_D$ of less than about 15 pM as measured in a surface plasmon resonance assay at 37° C.

In some embodiments, the antibody or antigen-binding fragment thereof that binds dimeric human PD-L1 with a K$_D$ less than about 8 pM in a surface plasmon resonance assay at 25° C.

In some embodiments, the antibody or antigen-binding fragment thereof competes for binding to human PD-L1 with a reference antibody comprising the complementarity determining regions (CDRs) of a HCVR, wherein the HCVR has an amino acid sequence selected from the group consisting of HCVR sequences listed in Table 1; and the CDRs of a LCVR, wherein the LCVR has an amino acid sequence selected from the group consisting of LCVR sequences listed in Table 1. In some embodiments, the reference antibody or antigen-binding fragment thereof comprises an HCVR/LCVR amino acid sequence pair as set forth in Table 1. In some embodiments, the reference antibody comprises an HCVR/LCVR amino acid sequence pair selected from the group consisting of SEQ ID NOs: 82/90, 98/106, 146/154, 162/170, 290/274, 306/274, 314/274 and 330/274.

In some embodiments, the antibody or antigen-binding fragment thereof enhances PD-L1 binding to one of PD-1 or B7-1. In some embodiments, the antibody or antigen binding fragment thereof blocks PD-L1 binding to PD-1 and/or B7-1. In some embodiments, the antibody or antigen binding fragment thereof do not increase or decrease PD-L1 binding to its ligands.

In some embodiments, the antibody or antigen-binding fragment thereof comprises the complementarity determining regions (CDRs) of a HCVR, wherein the HCVR has an amino acid sequence selected from the group consisting of SEQ ID NOs: 18, 66, 114, 130, 202, 218, 266, 282, 298, 322, and 338; and the CDRs of a LCVR, wherein the LCVR has an amino acid sequence selected from the group consisting of SEQ ID NOs: 26, 74, 122, 138, 210, 226, and 274. In certain embodiments, the isolated antibody comprises an HCVR/LCVR amino acid sequence pair selected from the group consisting of SEQ ID NOs: 18/26, 66/74, 114/122, 130/138, 202/210, 218/226, 266/274, 282/274, 298/274, 322/274, and 338/274.

In some embodiments, the antibody is a human monoclonal antibody or antigen-binding fragment thereof that binds specifically to human PD-L1, wherein the antibody or antigen-binding fragment thereof comprises a heavy chain variable region (HCVR) having an amino acid sequence selected from the group consisting of HCVR sequences listed in Table 1.

In some embodiments, the antibody is a human monoclonal antibody or antigen-binding fragment thereof that binds specifically to human PD-L1, wherein the antibody or antigen-binding fragment thereof comprises a light chain variable region (LCVR) having an amino acid sequence selected from the group consisting of LCVR sequences listed in Table 1.

In some embodiments, the antibody a human monoclonal antibody or antigen-binding fragment thereof that binds specifically to human PD-L1, wherein the antibody or antigen-binding fragment thereof comprises (a) a HCVR having an amino acid sequence selected from the group consisting of HCVR sequences listed in Table 1; and (b) a LCVR having an amino acid sequence selected from the group consisting of LCVR sequences listed in Table 1.

In some embodiments, the antibody or antigen-binding fragment thereof comprises three heavy chain complementarity determining regions (CDRs) (HCDR1, HCDR2 and HCDR3) contained within any one of the heavy chain variable region (HCVR) sequences listed in Table 1; and three light chain CDRs (LCDR1, LCDR2 and LCDR3) contained within any one of the light chain variable region (LCVR) sequences listed in Table 1.

In some embodiments, the antibody or antigen-binding fragment thereof comprises:

(a) a HCDR1 domain having an amino acid sequence selected from the group consisting of SEQ ID NOs: 4, 20, 36, 52, 68, 84, 100, 116, 132, 148, 164, 180, 188, 204, 220, 236, 252, 268, 284, 292, 300, 308, 316, 324, 332, and 340;

(b) a HCDR2 domain having an amino acid sequence selected from the group consisting of SEQ ID NOs: 6, 22, 38, 54, 70, 86, 102, 118, 134, 150, 166, 182, 190, 206, 222, 238, 254, 270, 286, 294, 302, 310, 318, 326, 334, and 342;

(c) a HCDR3 domain having an amino acid sequence selected from the group consisting of SEQ ID NOs: 8, 24, 40, 56, 72, 88, 104, 120, 136, 152, 168, 184, 192, 208, 224, 240, 256, 272, 288, 296, 304, 312, 320, 328, 336, and 344;

(d) a LCDR1 domain having an amino acid sequence selected from the group consisting of SEQ ID NOs: 12, 28, 44, 60, 76, 92, 108, 124, 140, 156, 172, 196, 212, 228, 244, 260, and 276;

(e) a LCDR2 domain having an amino acid sequence selected from the group consisting of SEQ ID NOs: 14, 30, 46, 62, 78, 94, 110, 126, 142, 158, 174, 198, 214, 230, 246, 262, and 278; and (f) a LCDR3 domain having an amino acid sequence selected from the group consisting of SEQ ID NOs: 16, 32, 48, 64, 80, 96, 112, 128, 144, 160, 176, 200, 216, 232, 248, 264, and 280.

In some embodiments, the antibody or antigen-binding fragment comprises a HCVR/LCVR amino acid sequence pair selected from the group consisting of SEQ ID NOs: 82/90, 98/106, 146/154, 162/170, 290/274, 306/274, 314/ 274 and 330/274

In some embodiments, the antibody or antigen-binding fragment thereof comprises the CDRs of a HCVR, wherein the HCVR has an amino acid sequence selected from the group consisting of SEQ ID NOs: 2, 34, 50, 82, 98, 146, 162, 178, 186, 234, 250, 290, 306, 314, and 330; and the CDRs of a LCVR, wherein the LCVR has an amino acid sequence selected from the group consisting of SEQ ID NOs: 10, 42, 58, 90, 106, 154, 170, 194, 242, 258, and 274.

E. Scaled Manufacturing for Production of Anti-PD-L1 Antibody-Chelator Conjugates Included in the present disclosure are scaled-up manufacturing processes for producing anti-PD-L1 antibodies conjugated to a chelator. The anti-PD-L1 antibody-chelator conjugates are in a form suitable for radiolabeling.

Good manufacturing processes are adhered to in all aspects of production, including maintaining a sterile environment, practicing aseptic procedures, keeping records of all processes, and documenting product quality, purity, strength, and identity, and any deviations therefrom.

The scaled-up manufacturing process is, in some embodiments, much faster than the manufacturing process for research and development. In some embodiments, the scaled-up manufacturing process can take less than 12 hours, or less than 10 hours, or less than 8 hours, or less than 6 hours, or less than 4 hours, or less than or about 2 hours.

In some embodiments, a first step comprises ultrafiltration and diafiltration (UFDF), using a 30-50 kDa membrane, of the anti-PD-L1 antibody to remove excipients, conjugation interfering species, and salts that inhibit the conjugation process. Exemplary membrane polymers include polyethersulfone (PES), cellulose acetate (CA), and regenerated cellulose (RC). In this step, the antibody is buffer exchanged in a low ionic strength and non-interfering buffer solution. The buffer pH can be between about 4.5 to about 6, or about 5 to about 6, or about 5.3 to about 5.7, or about 5.5. Buffer systems contemplated as useful herein include any buffer system lacking a primary amine. Exemplary buffers include acetate, phosphate, or citrate buffers. The buffer provides protein stability during pre-conjugation processing. The process volume can be further reduced to concentrate the antibody, then sterile filtered.

Following the pre-conjugation UFDF, the concentrated and filtered antibody can be transferred into an amine free carbonate buffer system. The carbonate buffer system can have a pH in a range from about 8.5 to about 9.6, or from about 9.0 to about 9.6, or from about 9.2 to about 9.4, or from about 9.4 to about 9.6, or a pH of about 9.4.

A chelator, for example, DFO, in solvent is added to a target concentration into the buffer system containing the antibody, and additional solvent can be added to the solution to a desired percentage. The chelator can be added in molar excess of the antibody, for example, 3.5-5:1 chelator to antibody. The total reaction volume can be up to 5 L.

The reaction temperature and the reaction time are inversely related. For example, if the reaction temperature is higher, the reaction time is lower. If the reaction temperature is lower, the reaction time is higher. Illustratively, at a temperature above about 18° C., the reaction may take less than 2 hours; at a temperature below 18° C., the reaction may take more than 2 hours.

The conjugation reaction can be terminated by quenching, for example, by the addition of acetic acid.

In some embodiments, conjugation of the antibody with deferoxamine is performed to produce DFO-mAb conjugates. In some embodiments, conjugation of the antibody with p-SCN-Bn-deferoxamine is performed to produce DFO-mAb conjugates.

Exemplary solvents for the chelator include DMSO and DMA. Subsequent UFDF steps utilize membranes, and the membrane is chosen based on the solvent system used in the conjugation step. For example, DMA dissolves PES membranes, so the two could not be used in the same system.

Carbonate buffers are not preferred for stability of the conjugate during long term storage. Thus, once the antibody-chelator conjugates have been formed, they can be buffer exchanged into a buffer chosen specifically for long term storage and stability. Exemplary buffers include citrate, acetate, phosphate, arginine, and histidine buffers. A further UFDF step can be performed to remove residual salts and to provide a suitable concentration, excipient level, and pH of the conjugated monoclonal antibody. The resulting antibody-chelator conjugates can be sterile filtered and stored for subsequent formulation.

III. Methods of Using Radiolabeled Immunoconjugates

In certain aspects, the present disclosure provides diagnostic and therapeutic methods of use of the radiolabeled antibody conjugates of the present disclosure.

According to one aspect, the present disclosure provides methods of detecting PD-L1 in a tissue, the methods comprising administering a radiolabeled antibody conjugate of the provided herein to the tissue; and visualizing the PD-L1 expression by positron emission tomography (PET) imaging. In certain embodiments, the tissue comprises cells or cell lines. In certain embodiments, the tissue is present in a subject, wherein the subject is a mammal. In certain embodiments, the subject is a human subject. In certain embodiments, the subject has a disease or disorder selected from the group consisting of cancer, infectious disease and inflammatory disease. In one embodiment, the subject has cancer. In certain embodiments, the infectious disease is bacterial or viral infection caused by, for example, hepatitis B virus (HBV), hepatitis C virus (HCV), human immunodeficiency virus (HIV), and *Mycobacterium tuberculosis*.

According to one aspect, the present disclosure provides methods of imaging a tissue that expresses PD-L1 comprising administering a radiolabeled antibody conjugate of the present disclosure to the tissue; and visualizing the PD-L1 expression by positron emission tomography (PET) imaging. In one embodiment, the tissue is comprised in a tumor. In one embodiment, the tissue is comprised in a tumor cell culture or tumor cell line. In one embodiment, the tissue is comprised in a tumor lesion in a subject.

According to one aspect, the present disclosure provides methods for measuring response to a therapy, wherein the response to a therapy is measured by measuring inflammation. The methods, according to this aspect, comprise administering a radiolabeled antibody conjugate provided herein to a subject in need thereof and visualizing the PD-L1 expression by positron emission tomography (PET) imaging. In certain embodiments, the inflammation is present in a tumor in the subject. In certain embodiments, an increase in PD-L1 expression correlates to increase in inflammation in the tumor.

According to one aspect, the present disclosure provides methods for determining if a patient is suitable for anti-tumor therapy comprising an inhibitor of the PD-1/PD-L1 signaling axis, the methods comprising selecting a patient with a solid tumor, administering a radiolabeled antibody conjugate of the present disclosure, and localizing the administered radiolabeled antibody conjugate in the tumor by PET imaging wherein presence of the radiolabeled antibody conjugate in the tumor identifies the patient as suitable for anti-tumor therapy comprising an inhibitor of the PD-1/PD-L1 signaling axis.

According to one aspect, the present disclosure provides methods for identifying a candidate for anti-tumor therapy comprising an inhibitor of the PD-1/PD-L1 signaling axis, the methods comprising selecting a patient with a solid tumor, administering a radiolabeled antibody conjugate of the present disclosure, and localizing the administered radiolabeled antibody conjugate in the tumor by PET imaging wherein presence of the radiolabeled antibody conjugate in the tumor identifies the patient as suitable for anti-tumor therapy comprising an inhibitor of the PD-1/PD-L1 signaling axis.

According to one aspect, the present disclosure provides methods for predicting response of a patient to an anti-tumor therapy comprising an inhibitor of the PD-1/PD-L1 signaling axis, the methods comprising selecting a patient with a solid tumor, determining if the tumor is PD-L1-positive, wherein a positive response of the patient is predicted if the tumor is PD-L1-positive. In certain embodiments, the tumor is determined positive by administering a radiolabeled antibody conjugate of the present disclosure and localizing the radiolabeled antibody conjugate in the tumor by PET imaging wherein presence of the radiolabeled antibody conjugate in the tumor indicates that the tumor is PD-L1-positive.

According to one aspect, the present disclosure provides methods for detecting a PD-L1-positive tumor in a subject. The methods, according to this aspect, comprise selecting a subject with a solid tumor; administering a radiolabeled antibody conjugate of the present disclosure to the subject; and determining localization of the radiolabeled antibody conjugate by PET imaging, wherein presence of the radiolabeled antibody conjugate in a tumor indicates that the tumor is PD-L1-positive.

As used herein, the expression "a subject in need thereof" means a human or non-human mammal that exhibits one or more symptoms or indications of cancer, and/or who has been diagnosed with cancer, including a solid tumor and who needs treatment for the same. In many embodiments, the term "subject" may be interchangeably used with the term "patient". For example, a human subject may be diagnosed with a primary or a metastatic tumor and/or with one or more symptoms or indications including, but not limited to, unexplained weight loss, general weakness, persistent fatigue, loss of appetite, fever, night sweats, bone pain, shortness of breath, swollen abdomen, chest pain/pressure, enlargement of spleen, and elevation in the level of a cancer-related biomarker (e.g., CA125). The expression includes subjects with primary or established tumors. In specific embodiments, the expression includes human subjects that have and/or need treatment for a solid tumor, e.g., colon cancer, breast cancer, lung cancer, prostate cancer, skin cancer, liver cancer, bone cancer, ovarian cancer, cervical cancer, pancreatic cancer, head and neck cancer, and brain cancer. The term includes subjects with primary or metastatic tumors (advanced malignancies). In certain embodiments, the expression "a subject in need thereof" includes patients with a solid tumor that is resistant to or refractory to or is inadequately controlled by prior therapy (e.g., treatment with an anti-cancer agent). For example, the expression includes subjects who have been treated with one or more lines of prior therapy such as treatment with chemotherapy (e.g., carboplatin or docetaxel). In certain embodiments, the expression "a subject in need thereof" includes patients with a solid tumor which has been treated with one or more lines of prior therapy but which has subsequently relapsed or metastasized. In certain embodiments, the term includes subjects having an inflammatory disease or disorder including, but not limited to, cancer, rheumatoid arthritis, atherosclerosis, periodontitis, hay fever, heart disease, coronary artery disease, infectious disease, bronchitis, dermatitis, meningitis, asthma, tuberculosis, ulcerative colitis, Crohn's disease, inflammatory bowel disease, hepatitis, sinusitis, psoriasis, allergy, fibrosis, lupus, vasiculitis, ankylosing spondylitis, Graves' disease, Celiac disease, fibromyalgia, and transplant rejection.

In certain embodiments, the methods of the present disclosure are used in a subject with a solid tumor. The terms "tumor", "cancer" and "malignancy" are interchangeably used herein. As used herein, the term "solid tumor" refers to an abnormal mass of tissue that usually does not contain cysts or liquid areas. Solid tumors may be benign (not cancer) or malignant (cancer). For the purposes of the present disclosure, the term "solid tumor" means malignant solid tumors. The term includes different types of solid tumors named for the cell types that form them, viz. sarcomas, carcinomas and lymphomas. In certain embodiments, the term "solid tumor" includes cancers including, but not limited to, colorectal cancer, ovarian cancer, prostate cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, and myeloma.

According to one aspect, the present disclosure provides methods of treating a tumor in a subject. The methods, according to this aspect, comprise selecting a subject with a solid tumor; determining that the tumor is PD-L1-positive; and administering one or more doses of an inhibitor of the PD-1/PD-L1 signaling axis. In certain embodiments, the tumor is determined to be PD-L1-positive by administering a radiolabeled antibody conjugate of the present disclosure to the subject; and visualizing the radiolabeled antibody conjugate in the tumor by PET imaging, wherein presence of the radiolabeled antibody conjugate in the tumor indicates that the tumor is PD-L1-positive.

As used herein, the terms "treat", "treating", or the like, mean to alleviate symptoms, eliminate the causation of symptoms either on a temporary or permanent basis, to delay or inhibit tumor growth, to reduce tumor cell load or tumor burden, to promote tumor regression, to cause tumor shrinkage, necrosis and/or disappearance, to prevent tumor recurrence, to prevent or inhibit metastasis, to inhibit metastatic tumor growth, and/or to increase duration of survival of the subject.

According to one aspect, the present disclosure provides methods for monitoring the efficacy of an anti-tumor therapy in a subject, wherein the methods comprise selecting a subject with a solid tumor wherein the subject is being treated with an anti-tumor therapy; administering a radiolabeled antibody conjugate of the present disclosure to the subject; imaging the localization of the administered radiolabeled conjugate in the tumor by PET imaging; and determining tumor growth, wherein a decrease from the baseline in radiolabeled signal indicates tumor regression and efficacy of the anti-tumor therapy. In certain embodiments, the anti-tumor therapy comprises an inhibitor of the PD-1/PD-L1 signaling axis (e.g., an anti-PD-1 antibody).

In certain embodiments, the present disclosure provides methods to assess changes in the inflammatory state of a tumor, the methods comprising selecting a subject with a solid tumor wherein the subject is being treated with an anti-tumor therapy; administering a radiolabeled antibody conjugate provided herein to the subject; and imaging the localization of the administered radiolabeled conjugate in the tumor by PET imaging, wherein an increase from the baseline in radiolabeled signal indicates increase in inflammation and efficacy of the anti-tumor therapy. In certain embodiments, the anti-tumor therapy comprises an inhibitor of the PD-1/PD-L1 signaling axis (e.g., an anti-PD-1 antibody).

As used herein, the term "baseline," with respect to the PD-L1 expression in the tumor, means the numerical value of uptake of the radiolabeled conjugate for a subject prior to or at the time of administration of a dose of anti-tumor therapy. The uptake of the radiolabeled conjugate is determined using methods known in the art (see, for example, Oosting et al 2015, J. Nucl. Med. 56: 63-69). In certain embodiments, the anti-tumor therapy comprises an inhibitor of the PD-1/PD-L1 signaling axis.

To determine whether there is tumor regression, the uptake of the radiolabeled conjugate is quantified at baseline and at one or more time points after administration of the inhibitor of the PD-1/PD-L1 signaling axis (e.g., an anti-PD-1 antibody). For example, the uptake of the administered radiolabeled antibody conjugate (e.g., radiolabeled anti-PD-L1 antibody conjugate) may be measured at day 2, day 3, day 4, day 5, day 6, day 7, day 8, day 9, day 10, day 11, day 12, day 14, day 15, day 22, day 25, day 29, day 36, day 43, day 50, day 57, day 64, day 71, day 85; or at the end of week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with the inhibitor of the PD-1/PD-L1 signaling axis (e.g., an anti-PD-1 antibody). The difference between the value of the uptake at a particular time point following initiation of treatment and the value of the uptake at baseline is used to establish whether there has been a difference in amount of tumor tissue (tumor regression or progression). For example, a decrease from baseline in the uptake upon treatment with at least one dose of the inhibitor of the PD-1/PD-L1 signaling axis means tumor regression and indicates efficacy of the anti-tumor therapy.

In certain embodiments, the radiolabeled antibody conjugate is administered intravenously or subcutaneously to the subject. In certain embodiments, the radiolabeled antibody conjugate is administered intra-tumorally. Upon administration, the radiolabeled antibody conjugate is localized in the tumor. The localized radiolabeled antibody conjugate is imaged by PET imaging and the uptake of the radiolabeled antibody conjugate by the tumor is measured by methods known in the art. In certain embodiments, the imaging is carried out 1, 2, 3, 4, 5, 6 or 7 days after administration of the radiolabeled conjugate. In certain embodiments, the imaging is carried out on the same day upon administration of the radiolabeled antibody conjugate.

In certain embodiments, the antibody or antigen-binding fragment thereof that binds specifically to PD-L1. In certain embodiments, the anti-PD-L1 antibody comprises the CDRs of a HCVR, wherein the HCVR has an amino acid sequence selected from the group consisting of SEQ ID NOs: 2, 34, 50, 82, 98, 146, 162, 178, 186, 234, 250, 290, 306, 314, and 330; and the CDRs of a LCVR, wherein the LCVR has an amino acid sequence selected from the group consisting of SEQ ID NOs: 10, 42, 58, 90, 106, 154, 170, 194, 242, 258, and 274.

In certain embodiments, the inhibitor of the PD-1/PD-L1 signaling axis comprises an antibody or antigen-binding fragment thereof that binds specifically to PD-1. In certain embodiments, the anti-PD-1 antibody is selected from the group consisting of nivolumab, pembrolizumab and REGN2810. In certain other embodiments, the inhibitor of the PD-1/PD-L1 signaling axis comprises an antibody or antigen-binding fragment thereof that binds specifically to PD-L1. In one embodiment, the anti-PD-L1 antibody is atezolizumab. In one embodiment, the anti-PD-L1 antibody comprises an HCVR of SEQ ID NO: 82 and a LCVR of SEQ ID NO: 90.

IV. Examples

Certain embodiments of the disclosure are illustrated by the following non-limiting examples.

Example 1: Generation of Human Antibodies to PD-L1

Human anti PD-L1 antibodies, including those listed in Table 1, were prepared and characterized as described in US Patent Publication No. US 2015-0203580 A1, which is incorporated herein by reference in its entirety. In brief, human antibodies to PD-L1 were generated using a fragment of PD-L1 that ranges from about amino acids 19-239 of PD-L1 (Genbank Accession No. NP_054862.1). The immunogen was administered directly, with an adjuvant to stimulate the immune response, to a VELOCIMMUNE® mouse comprising DNA encoding human Immunoglobulin heavy and kappa light chain variable regions. The antibody immune response was monitored by a PD-L1-specific immunoassay. When a desired immune response was achieved splenocytes were harvested and fused with mouse myeloma cells to preserve their viability and form hybridoma cell lines. The hybridoma cell lines were screened and selected to identify cell lines that produce PD-L1-specific antibodies. Using this technique, and the immunogen described above, several anti-PD-L1 chimeric antibodies (i.e., antibodies possessing human variable domains and mouse constant domains) were obtained; exemplary antibodies generated in this manner were designated as H2M8306N, H2M8307N, H2M8309N, H2M8310N, H2M8312N, H2M8314N, H2M8316N, H2M8317N, H2M8321N, H2M8323N, H2M8718N, H2M8718N2, and H2M8719N.

Anti-PD-L1 antibodies were also isolated directly from antigen-positive B cells without fusion to myeloma cells, as described in U.S. 2007/0280945A1, herein specifically incorporated by reference in its entirety. Using this method, several fully human anti-PD-L1 antibodies (i.e., antibodies possessing human variable domains and human constant domains) were obtained; exemplary antibodies generated in this manner were designated as follows: H1H9323P, H1H9327P, H1H9329P, H1H9336P, H1H9344P2, H1H9345P2, H1H9351P2, H1H9354P2, H1H9364P2, H1H9373P2, H1H9382P2, H1H9387P2, and H1H9396P2.

Example 2: Conjugation of Anti-PD-L1 Antibody H4H8314N with p-SCN-Bn-DFO

In order to modify the parental anti-PD-L1 antibody, H4H8314N, and an isotype control antibody to be suitable for ImmunoPET studies with radiolabeling, a chelator, p-SCN-bn-Deferoxamine (DFO; Macrocylics, Cat #: B-705), was attached to the antibodies.

For the modification, H4H8314N was first buffer exchanged into PBS, pH 7.2 from histidine buffer by dialysis at 4° C. overnight (Slide-A-Lyzer Dialysis Cassette G2 10 k MWCO; ThermoScientific) then buffer exchanged again using a PD-10 column (GE Healthcare, Cat. #: 17-0851-01) into a buffer composed of 50 mM carbonate buffer, 150 mM NaCl, pH 9.0 (conjugation buffer). To determine the concentration following the buffer exchanges, the samples were measured on a Nanodrop 2000 UV/VIS spectrometer (Thermo Scientific) using the MacVector sequence based extinction coefficient of 1.46 g/L (see Table 2). In 15 a mL polypropylene tube, 773.9 uL of H4H8314N (12.5 mg) was added to 1676.1 uL of conjugation buffer. In a separate vial, 29.3 uL of DMSO was added to 20.7 uL of DFO. In one-quarter increments, this DFO solution was added to the H1H8314N solution, each time gently being mixed by pipetting up-and-down. The final solution was 5 mg/mL H4H8314N in conjugation buffer, 2% DMSO with 6-fold mole-to-mole excess of DFO. This solution was allowed to incubate in a 37° C. water bath with no additional stirring.

After 30 minutes at 37° C., the solution was promptly passed through a PD-10 desalting column (GE Healthcare, Cat. #: 17-0851-01), pre-equilibrated with a buffer containing 250 mM NaAcO at pH 5.4 (formulation buffer). The final solution was sterile-filtered via a syringe filter (Acrodisc 13 mm syringe filter, Pall Corporation, Cat #: 4602). The concentration and DFO-to-Antibody Ratio (DAR) was subsequently measured by UV/VIS spectroscopy. For the absorbance measurement, the DFO-conjugated antibody was measured against the formulation buffer at 252 nm (A252), 280 nm (A280) and 600 nm (A600). For the calculation, the background was corrected at each absorbance value using the equation:

$$A'_\lambda = A_\lambda - A_{600}$$

Figure 1A:
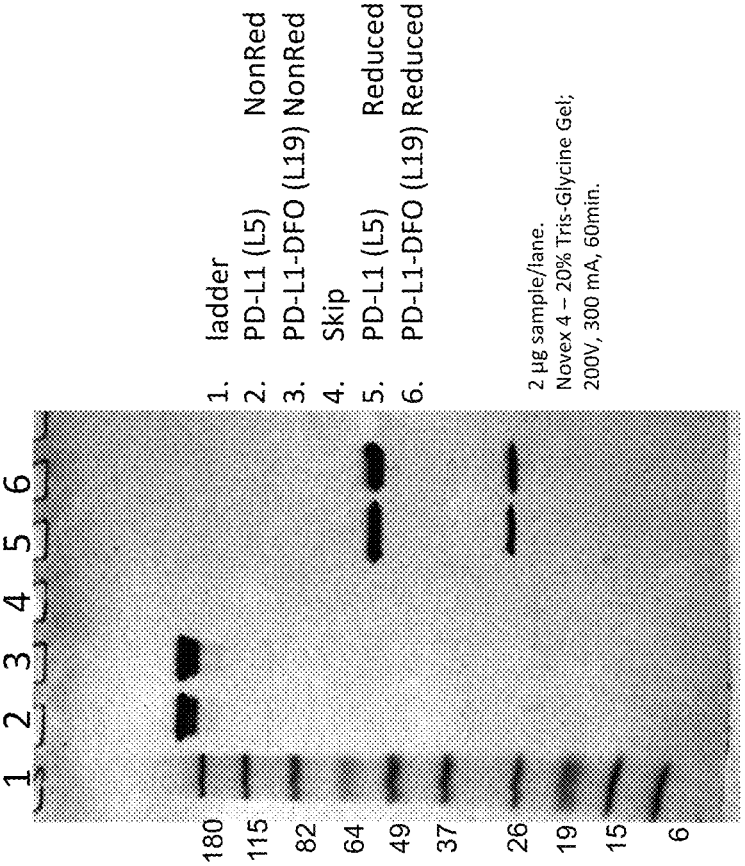

The antibody conjugate was tested for aggregation using SEC chromatography, with 25 ug of the sample injected onto a Superdex 200 column (GE Healthcare, Cat. No. 17-5175-01) monitored at 280 nm with a PBS mobile phase (0.75 mL/min). The antibody integrity was evaluated by SDS-PAGE 4-20% Tris/Gly pre-cast gel (Novex) with 2 ug of the sample loaded. The gel is shown in FIG. 1. The antibody concentration, conjugate concentration, and DAR were calculated using the equations below:

Antibody Concentration Calculation $$\text{Conc mAb (mg/mL)} = \frac{A'_{280}}{\varepsilon_{280}}$$

Conjugate Concentration Calculation $$\text{Conc conjugate (mg/mL)} = \frac{A'_{252} - 1.53 A'_{280}}{\varepsilon_{252} - 1.53 \varepsilon_{280}}$$

DAR Calculation $$DAR = \frac{\varepsilon_{252} A'_{280} - \varepsilon_{280} A'_{252}}{18800 A'_{252} - 28700 A'_{280}}$$

TABLE 2

Molar extinction coefficients and molecular weight

| Antibody | MW (g mol$^{-1}$) | ε280 (L g$^{-1}$cm$^{-1}$) | ε252 (L g$^{-1}$cm$^{-1}$) |
|---|---|---|---|
| H4H8314N | 144984 | 1.46 | 0.553 |

TABLE 3

UV DAR, percent aggregate and concentration post DFO-attachment

| Antibody | UV DAR | Concentration (mg/mL) | % aggregate |
|---|---|---|---|
| H4H8314N | 1.2 | 3.34 | <1% |

Example 3: $^{89}$Zr Chelation of DFO Conjugated Monoclonal Antibodies

For use in ImmunoPET in vivo studies, the DFO-conjugated anti-PD-L1 antibody, H4H8314N, and a DFO-conjugated isotype control antibody were radiolabeled with $^{89}$Zr.

DFO-conjugated antibody (250 or 750 ug) was first brought to 1.25 mg/mL in 1 M HEPES, pH 7.2. The recipe of DFO-Ab conjugate solution for each study is listed in Table 4. Separately, $^{89}$Zr solution was prepared using the recipe for each corresponding study shown in Table 5. Stock $^{89}$Zr-oxalic acid solution was obtained from PerkinElmer or 3D Imaging. If the radioactivity concentration of the stock solution was low (see Table 5), a neutralization step was performed with 1 M borate, pH 9.0. The final radioactivity of the solution was first confirmed using a Capintec CRC-25R dose calibrator (Capintec #520), then immediately combined with the DFO-Ab conjugate solution, gently mixed (pipetting up-and-down) and subsequently incubated for 45 minutes at room temperature.

After the incubation, a small sample of each reaction mixture was taken for iTLC (instant thin layer liquid chromatography) to determine radiolabeling reaction yield and the remaining reaction mixtures were transferred to pre-equilibrated PD-10 columns (Vendor) with 250 mM sodium acetate at pH 5.4 for gravity fed desalting. Each PD-10 column took no more than 1.2 mL of reaction mixture (otherwise multiple columns were used). After the contents of the reaction entered the column bed, 1.6 mL of 250 mM sodium acetate at pH 5.4 (formulation buffer) was added; the flow through was discarded. An additional 1.8 mL of formulation buffer was added to the column, and the eluate was collected from each column. Next, approximately 500 uL of each solution was analyzed using a Nanodrop spectrophotometer (ThermoScientific). The final Ab concentration was calculated using the appropriate extinction coefficient and the absorption at 280 nm using the equation:

Concentration in mg/mL=Absorption at 280 nm÷Extinction coefficient at 280 nm (found in Table 6)

The final mass measured in grams was recorded in Table 4. The radioactivity was then measured using the dose calibrator and reported in Table 5. The final material along with the material prior to the PD-10 column treatment, were then analyzed by iTLC. For this assay, 1 uL of each solution was added to the iTLC-SG-Glass microfiber chromatography paper impregnated with silica gel (Agilent Technologies, Cat # SG10001), developed in a TLC chamber with 20 mM citric acid buffer solution. The final material was also analyzed using a SEC-HPLC with UV 280 and radioisotope detector connected in series (Agilent 1260 with Lablogic Radio-TLC/HPLC Detector, SCAN-RAM) using a Superdex 200 column with PBS mobile phase at a flow rate of 0.75 mL/min. The radiotrace was used for the determining radiochemical purity by comparing the integration of the protein peak (~10 to 16 min) and free $^{89}$Zr peak (~25 min). The monomeric purity was determined by comparing the integration of the oligomeric peak (10 min to ~15 min) to the monomer (~16 min).

The specific activity and protein recovery (%) of each radiolabeled conjugate was determined using the following equations:

Mass of conjugate in mg=concentration in mg/mL× mass of solution in grams a.

Specific activity in mCi/mg=activity of vial in mCi÷mass of conjugate in mg b.

Protein recovery=starting conjugate mass (mg)÷Mass of conjugate in mg c.

Finally the appearance was noted and recorded in Table 7. Both UV280 and iTLC traces were performed on purified product.

Figure 2A:
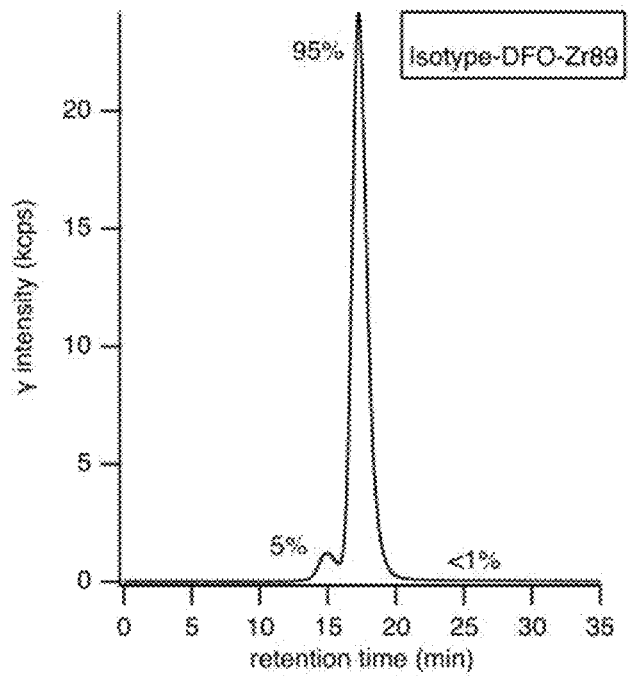
FIGS. 2A and 2B depict radio-SEC-HPLC after $^{89}$Zr radiolabeling for Study 1.
Figure 2B:
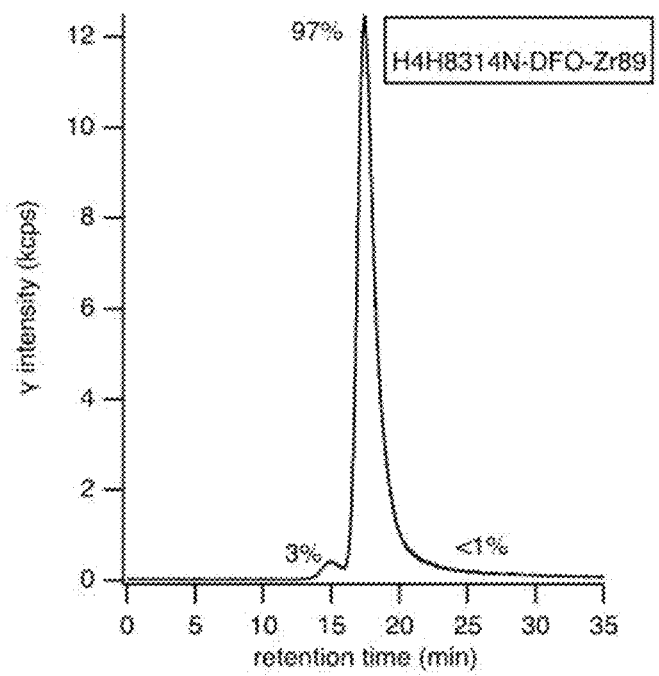
Figure 3:
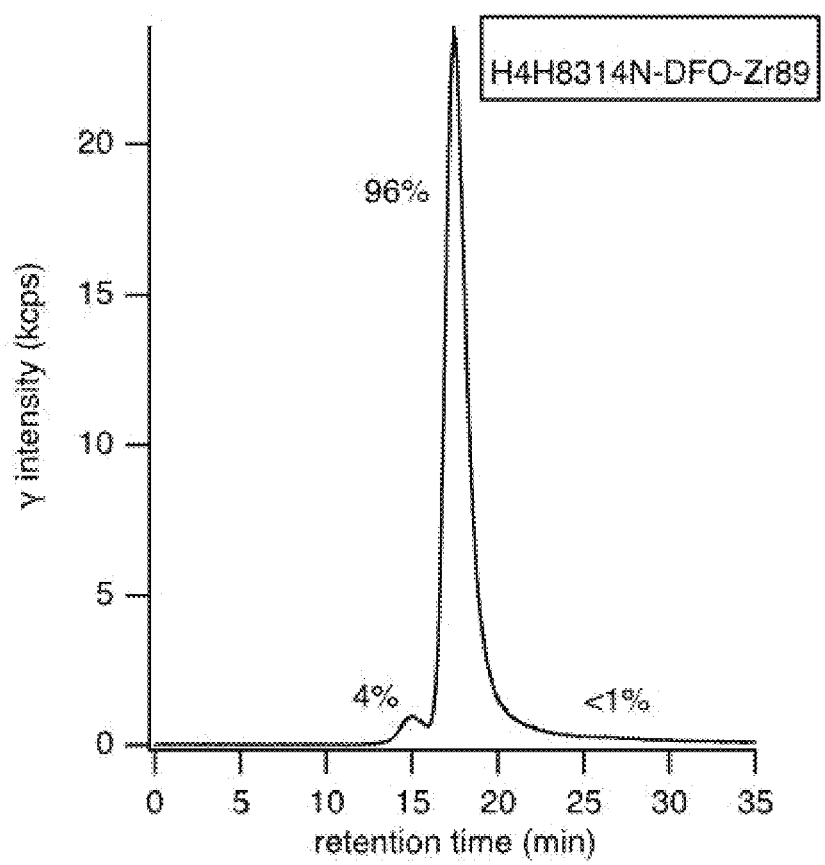
FIG. 3 depicts radio-SEC-HPLC of DFO-conjugate (anti-PD-L1) after $^{89}$Zr radiolabeling for Study 2.
Figure 4:
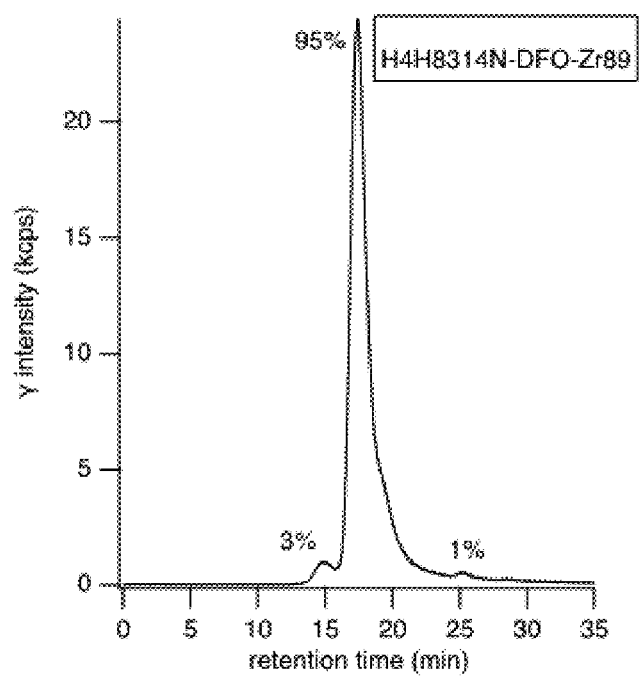
FIG. 4 depicts radio-SEC-HPLC SEC after $^{89}$Zr radiolabeling Study 3.
Figure 5A:
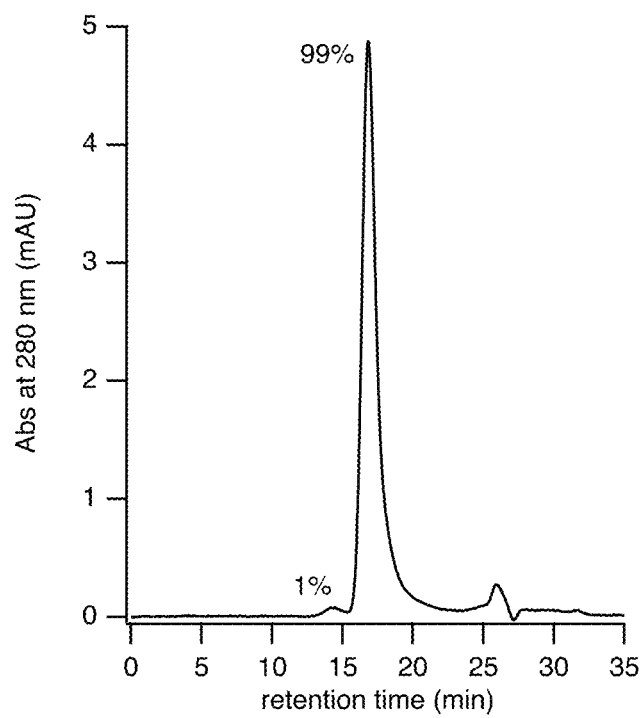
FIG. 5A depicts UV280-SEC-HPLC chromatogram and FIG. 5B depicts radio-iTLC trace after $^{89}$Zr radiolabeling for Study 1.
Figure 5B:
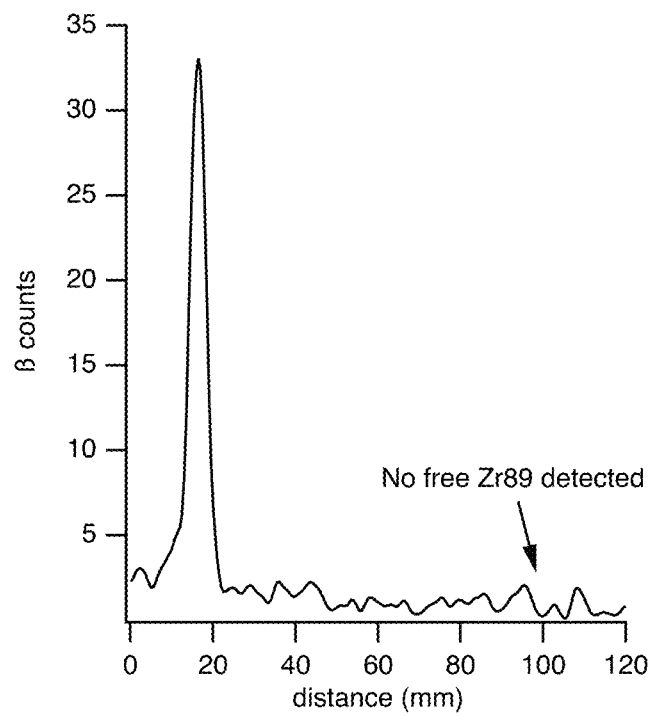
Figure 6A:
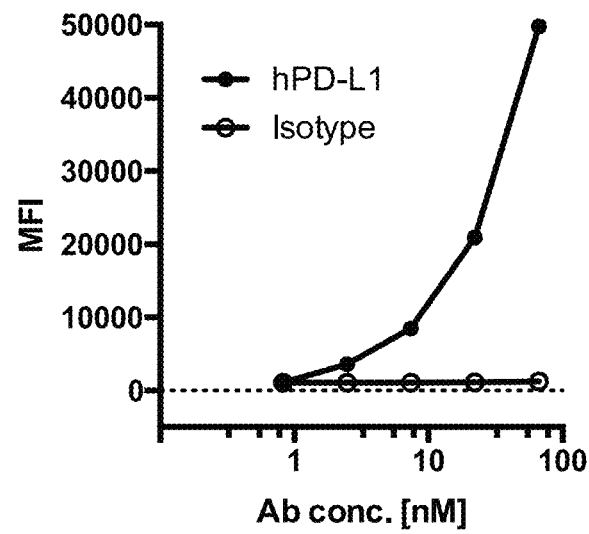
FIGS. 6A, 6B, 6C, and 6D shows hPD-L1 expression by tumor cell lines MC38-cOVA/eGFP-mPD-L1−/−hPD-L1$^{Tg}$ (FIG. 6A), LOX-IMVI (FIG. 6B), MDA-MB-231 (FIG. 6C), and SK-Br-3 (FIG. 6D) in vitro, as described in Example 5 herein.
Figure 6B:
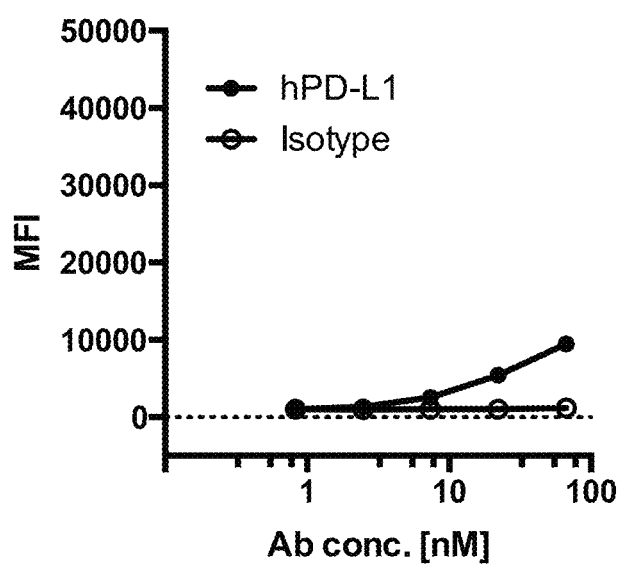
Figure 6C:
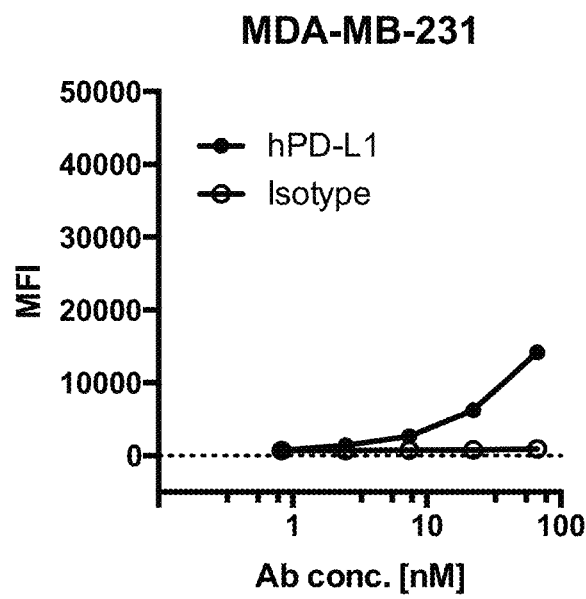
Figure 6D:
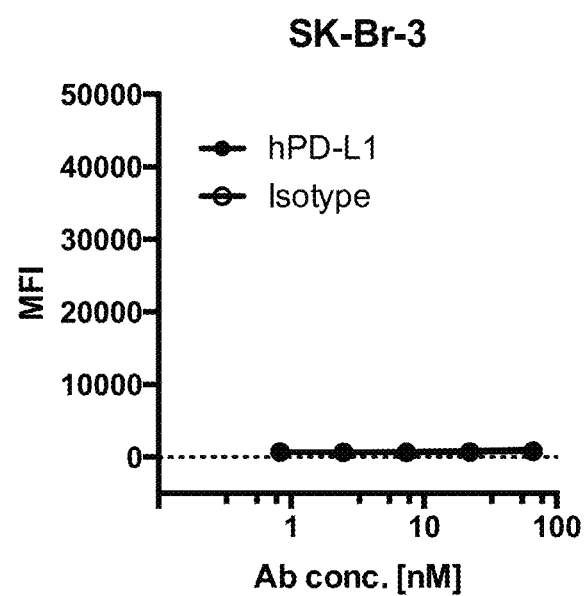

The results are consolidated in Table 7. The radio-SEC-HPLC chromatograms are shown in FIGS. 2-4. An example of UV280 HPLC SEC chromatogram and radio-iTLC is shown in FIG. 5 for the $^{89}$Zr radiolabeling, Study 1. The UV280-HPLC SEC chromatogram confirms the highly monomeric product (99%). The radio-iTLC trace was processed with a 7-point binomial smoothing function. The origin and solvent front was approximately 16 and 100 mm, respectively. No detectable $^{89}$Zr was observed beyond 22 mm and corroborates the radiochemical purity determined by radio-SEC-HPLC SEC in FIG. 2B.

TABLE 4

DFO-antibody conjugate preparation for radiolabeling

| Radio-labeling # | Study # | Radiolabeling Lots | Concentration (mg/mL) | DAR* | Conjugate mass (mg) | Total volume (uL) | Final Concentration (mg/mL) |
|---|---|---|---|---|---|---|---|
| 1 | 1 | Isotype-DFO-$^{89}$Zr | 3.7 | 1.6 | 250 | 200 | 1.25 |
| 2 | 1 | H4H8314N-DFO-$^{89}$Zr | 3.34 | 1.2 | 250 | 200 | 1.25 |
| 3 | 2 | H4H8314N-DFO-$^{89}$Zr | 3.34 | 1.2 | 750 | 600 | 1.25 |
| 4 | 3 | Isotype-DFO-$^{89}$Zr | 3.7 | 1.6 | 250 | 200 | 1.25 |
| 5 | 3 | H4H8314N-DFO-$^{89}$Zr | 3.34 | 1.2 | 250 | 200 | 1.25 |

*DAR is defined as the DFO to Antibody Ratio

TABLE 5

$^{89}$Zr reaction solution preparation for radiolabeling

| Radio-labeling | Study # | Radiolabeling Lots | $^{89}$Zr-oxalate (uL) | Add'l 1M oxalic acid added (uL) | 1M borate, pH 9.0 added (uL) | 1M HEPES, pH 7.2 (uL) | Final Vol (uL) | Final Activity (uCi) | Specific Activity (uCi/UL) |
|---|---|---|---|---|---|---|---|---|---|
| 1 | 1 | Isotype-DFO-$^{89}$Zr | 50 | 50 | 400 | 500 | 1000 | 1009 | 1.01 |
| 2 | 1 | H4H8314N-DFO-$^{89}$Zr | 50 | 50 | 400 | 500 | 1000 | 1000 | 1 |
| 3 | 2 | H4H8314N-DFO-$^{89}$Zr | 150 | 150 | 1200 | 1500 | 3000 | 3070 | 1.02 |
| 4 | 3 | Isotype-DFO-$^{89}$Zr | ~1 | 0 | 0 | 1000 | 1000 | 1680 | 1.68 |
| 5 | 3 | H4H8314N-DFO-$^{89}$Zr | ~1 | 0 | 0 | 1000 | 1000 | 1640 | 1.64 |

TABLE 6

Extinction coefficients for conjugate lots

| Radiolabeling Lot | $\varepsilon_{280}$ (AU ml mg$^{-1}$ cm$^{-1}$) |
|---|---|
| Isotype-DFO-$^{89}$Zr | 1.71 |
| H4H8314N-DFO-$^{89}$Zr | 1.61 |

TABLE 7

Summary of $^{89}$Zr labeled DFO-Ab conjugates for in vivo imaging and biodistribution studies

| Radio-labeling # | Study # | Conjugate Lots | Appearance | Radio-chemical Purity* (%) | Mono-meric Purity* (%) | Protein Recovery (%) | Conc. (mg/mL) | Specific Activity (mCi/mg) |
|---|---|---|---|---|---|---|---|---|
| 1 | 1 | Isotype-DFO-$^{89}$Zr | Clear | >99% | >95% | 60% | 0.106 | 3.35 |
| 2 | 1 | H4H8341N-DFO-$^{89}$Zr | Clear | >99% | >95% | 63% | 0.121 | 2.75 |
| 3 | 2 | H4H8341N-DFO-$^{89}$Zr | Clear | >99% | >95% | 62% | 0.134 | 3.58 |
| 4 | 3 | Isotype-DFO-$^{89}$Zr | Clear | >99% | >95% | 66% | 0.074 | 5.38 |
| 5 | 3 | H4H8341N-DFO-$^{89}$Zr | Clear | >99% | >95% | 74% | 0.084 | 5.13 |

*by radio-SEC-HPLC

Example 4: Immunoreactivity

The immunoreactivity (IR) of the radiolabeled anti-PD-L1 antibody and isotype control antibody was measured as follows. For the initial studies, MC38-cOVA/eGFP-mPD-L1$^{-/-}$hPD-L1$^{Tg}$ cells were used and subsequently LOX-IMVI cells (see detailed description of cell lines in Example 5) were also used in the later study. In these assays, 20 ng of the respective $^{89}$Zr labeled antibodies were added to 15×10$^6$ MC38-cOVA/eGFP-mPD-L1$^{-/-}$hPD-L1$^{Tg}$ or 30×10$^6$ LOX-IMVI cells in a final volume of 1 mL. Samples were incubated for 45 minutes with continuous mixing before undergoing 3 washes with media to remove any unbound antibody. The radioactivity of the test cell pellets was then counted in an automatic gamma counter (Wizard 2470, Perkin Elmer) against 2 reference standards containing the same 20 ng of $^{89}$Zr labeled antibody. The percentage immunoreactivity was determined for the samples using the average of the standards as a measure of total activity.

As seen in Table 8, $^{89}$Zr labeled anti-PD-L1 antibody retained immunoreactivity following conjugation and radiolabeling, with % IR ranging from 88 to 98% across the studies. The specificity of binding is apparent in the control antibodies having a background % IR of less than 1%.

TABLE 8

Immunoreactivity of $^{89}$Zr chelated DFO-conjugates

| | Study 1 | | Study 2 | | Study 3 | | | |
|---|---|---|---|---|---|---|---|---|
| | Cell Line | | | | | | | |
| | MC38-cOVA/eGFP-mPD-L1$^{-/-}$hPD-L1$^{Tg}$ | | MC38-cOVA/eGFP-mPD-L1$^{-/-}$hPD-L1$^{Tg}$ | | MC38-cOVA/eGFP-mPD-L1$^{-/-}$hPD-L1$^{Tg}$ | | LOX-IMVI | |
| | Antibody | | | | | | | |
| | $^{89}$Zr-Anti-PD-L1 | $^{89}$Zr-Control | $^{89}$Zr-Anti-PD-L1 | $^{89}$Zr-Control | $^{89}$Zr-Anti-PD-L1 | $^{89}$Zr-Control | $^{89}$Zr-Anti-PD-L1 | $^{89}$Zr-Control |
| Cell pellet activity | 4048.4 | 29.6 | 8311.9 | na | 6262.4 | 68 | 5587.54 | 65.4 |
| Average Standard activity | 4536.5 | 6432.4 | 8567.2 | na | 6386.6 | 9544.8 | 6386.6 | 9544.8 |
| Percent IR | 89.2 | 0.5 | 97.0 | na | 98.1 | 0.7 | 87.5 | 0.7 |

Example 5: In Vitro and Ex Vivo Characterization of Human PD-L1 Expression on Tumor Cell Lines Several tumor cell lines were studied to evaluate the expression level of human PD-L1, aiming at the detection of human PD-L1 expressed endogenously by tumors in vivo in either male NCr nude (Taconic, Hudson N.Y.) mice or in mice that were engineered to be homozygous for the expression of the extracellular domain of human PD-L1 in place of extracellular domain of mouse PD-L1 (PD-L1 HumIn mice) on a 75% C57/Bl6/25% 129 strain background using VelociGene® technology (Valenzuela et al 2003, Nat. Biotechnol. 21: 652-659; US Patent Application Publication US2016/0157469).

Cell lines used in these studies include: 1) a murine colon carcinoma cell line MC38 (obtained from NCI at Frederick, Md., Laboratory of Tumor Immunology and Biology), which has been engineered in house to knock out murine PD-L1, but over-express full-length human PD-L1 and full-length chicken ovalbumin fused with eGFP, thus referred here as MC38-cOVA/eGFP-mPD-L1$^{-/-}$hPD-L1$^{Tg}$; 2) several human tumor cell lines: human melanoma cell line LOX-IMVI (endogenous PD-L1 positive line, obtained from NCI at Frederick, Md., Division of Cancer Treatment and Diagnosis, Tumor Repository), human breast cancer cell lines MDA-MB-231 (endogenous PD-L1 positive line) and SK-Br-3 (PD-L1 negative cell line) (both obtained from ATCC). In some cases, human PD-L1 was directly evaluated without any induction in vitro; in some cases, human PD-L1 expression was evaluated with overnight murine or human IFNγ (100 ng/ml) treatment (obtained from Peprotech); in some cases, human PD-L1 was evaluated ex vivo on enzymatically dissociated tumor cells extracted from tumor bearing nude mice or humanized mice. All surface staining of human PD-L1 was performed following a standard protocol. Briefly, tumor cells were washed with PBS once, washed with ice cold staining buffer once, stained with commercial available fluorochrome directly conjugated anti-human PD-L1 antibody (eBioscience, clone MIH1) in staining buffer for 30 minutes on ice in the dark, and then washed with 2 mL of PBS once again. Fixable dye eFluor506 was also included following manufacturer's protocol (eBioscience, Cat #17-5983). Samples were acquired on BD FACSCanto II™ IVD10 equipped with DIVA v8. Data were further analyzed with FlowJo v10.0.6 or above.

PD-L1 expression by MC38-cOVA/eGFP-mPD-L1$^{-/-}$hPD-L1$^{Tg}$ cells prior to implantation and seven days post implantation in nude mice is shown in Table 9.

TABLE 9

Percentage of human PD-L1 positive MC38-cOVA/eGFP-mPD-L1$^{-/-}$hPD-L1$^{Tg}$ cells prior to implantation and 7 days post implantation in nude mice

| | Isotype staining | hPD-L1 staining |
|---|---|---|
| Prior to implantation | 0.6% | 94.7% |
| Post implantation | 1.09% | 74.0% |

Prior to implantation, a vast majority of MC38-cOVA/eGFP-mPD-L1$^{-/-}$hPD-L1$^{Tg}$ cells were human PD-L1 positive, compared to isotype control staining. Seven days post implantation in nude mice and upon enzymatic and mechanical processing for tumor dissociation, ~70% of MC38-cOVA/eGFP-mPD-L1$^{-/-}$hPD-L1$^{Tg}$ cells were still human PD-L1 positive.

PD-L1 expression by MC38-cOVA/eGFP-mPD-L1$^{-/-}$hPD-L1$^{Tg}$ cells prior to implantation and fourteen days post implantation in PD-L1 humanized mice is shown in Table 10.

TABLE 10

Percentage of human PD-L1 positive MC38-cOVA/eGFP-mPD-L1$^{-/-}$hPD-L1$^{Tg}$ cells prior to implantation and 14 days post implantation in PD-L1 humanized mice

| | Isotype staining | hPD-L1 staining |
|---|---|---|
| Prior to implantation | 0.2% | 92.5% |
| Post implantation | 3.6 | 46.2% |

Prior to implantation, a vast majority of MC38-cOVA/eGFP-mPD-L1$^{-/-}$hPD-L1$^{Tg}$ cells were human PD-L1 positive, compared to isotype control staining. Fourteen days post implantation in PD-1/PD-L1 double humanized mice and upon enzymatic and mechanical processing for tumor dissociation; ~50% of MC38-cOVA/eGFP-mPD-L1$^{-/-}$hPD-L1$^{Tg}$ cells were still human PD-L1 positive.

PD-L1 expression by multiple tumor cell lines in vitro is shown in FIG. 6. To evaluate how comparable the expression level of PD-L1 by the engineered cell line (MC38-cOVA/eGFP-mPD-L1$^{-/-}$hPD-L1$^{T}$g) and other human tumor cell lines (LOX-IMVI melanoma cells, MDA-MB-231 breast cancer cells, and SK-Br-3 breast cancer cells) was, dose titration of anti-PD-L1 antibody staining was performed. FIG. 6 illustrates that MC38-cOVA/eGFP-mPD-L1$^{-/-}$hPD-L1$^{Tg}$ had the highest level of human PD-L1 expression (FIG. 6A) and SK-Br-3 had the lowest expression with no PD-L1 detectable (FIG. 6D), whereas PD-L1 expression by LOX-IMVI and MDA-MB-231 was moderate (about 5 times lower than MC38-cOVA/eGFP-mPD-L1$^{-/-}$hPD-L1$^{T}$g) (FIGS. 6B and 6C).

Figure 7:
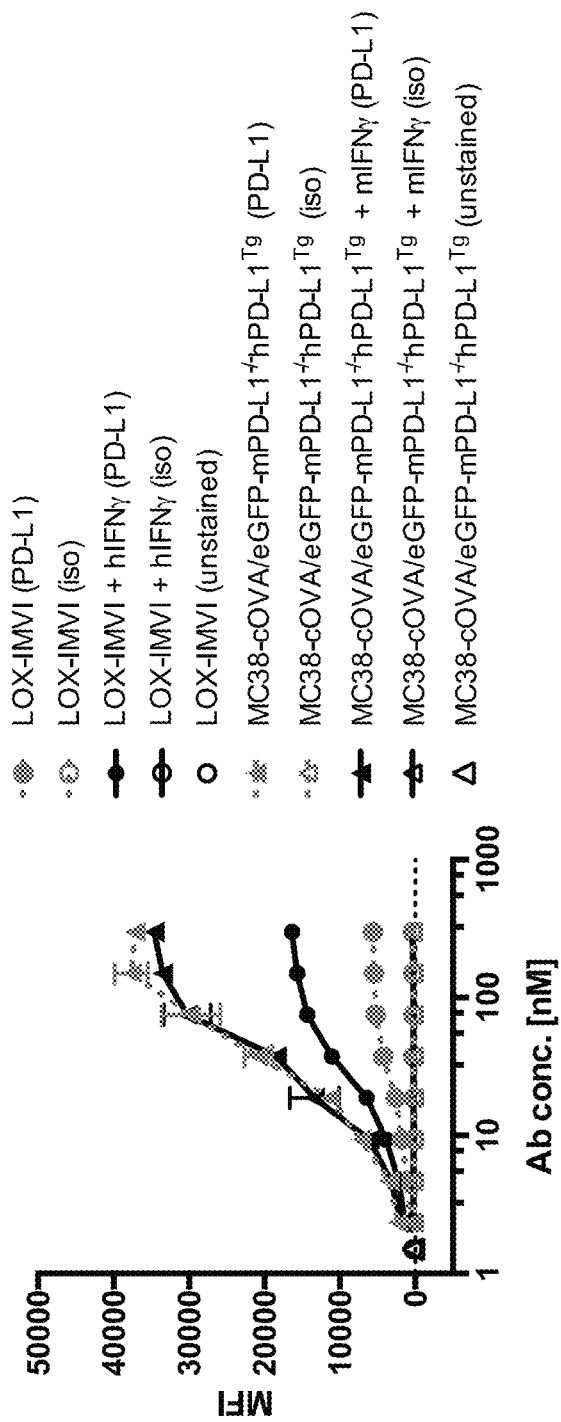
FIG. 7 shows hPD-L1 expression by MC38-cOVA/eGFP-mPD-L1−/−hPD-L1$^{Tg}$ and LOX-IMVI tumor cells with or without interferon-gamma treatment in vitro in a second experiment, as described in Example 5 herein.
Figure 8A:
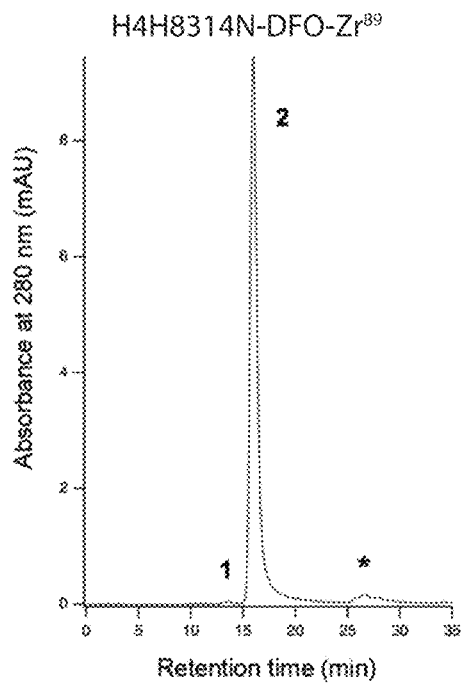
In FIG. 8A-FIG. 8C, elution of buffer components was also detected. These peaks of salts in the sample buffer (retention time>25 min, asterisk "*") were excluded from the integration of peak areas. Peaks are labeled to indicate HMW (high molecular weight) immunoconjugate ("1"), monomeric immunoconjugate ("2"), unincorporated $^{89}$Zr ("3"), and salts in the sample buffer ("*"). Abbreviations: mAU=milli absorbance units; cps=counts per second.
Figure 8B:
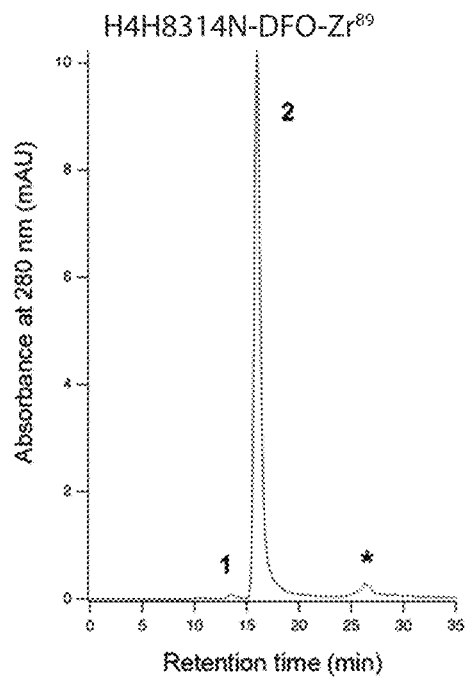
Figure 8C:
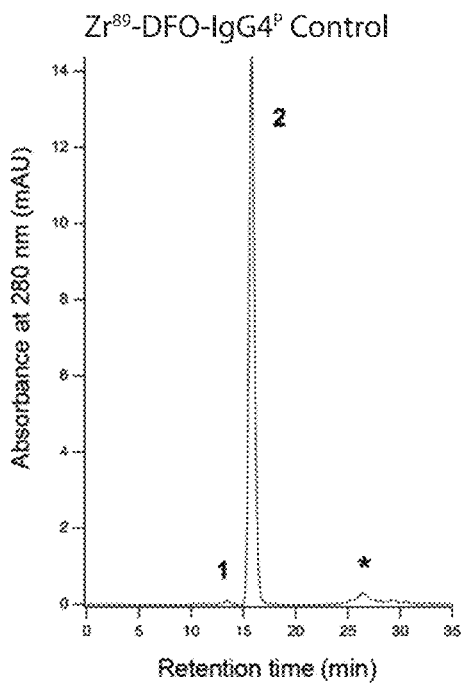
Figure 8D:
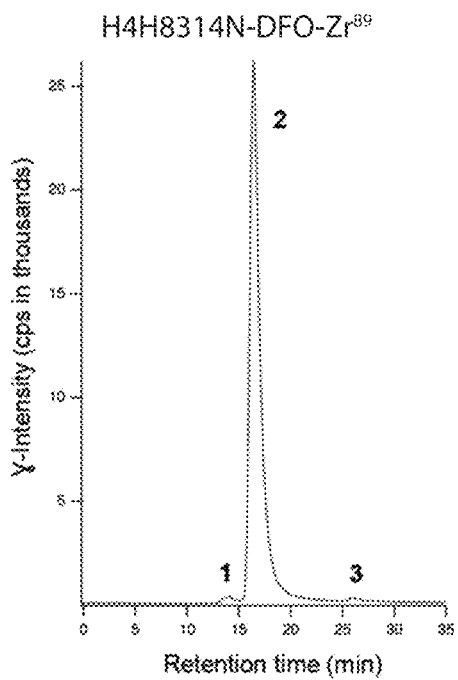
FIG. 8 depicts chromatograms generated by SEC-HPLC analysis using samples from radioimmunoconjugate preparations of $^{89}$Zr-DFO-anti-PD-L1 antibody conjugate for studies shown in FIG. 8A, FIG. 8B, FIG. 8D, and FIG. 8E, and of isotype control radioimmunoconjugate $^{89}$Zr-DFO-IgG4$^P$ for studies shown in FIG. 8C and FIG. 8F. Chromatograms for absorbance at 280 nm are shown in FIG. 8A-FIG. 8C and radio-chromatograms for intensity of γ-emission are shown in FIG. 8D-FIG. 8F.
Figure 8E:
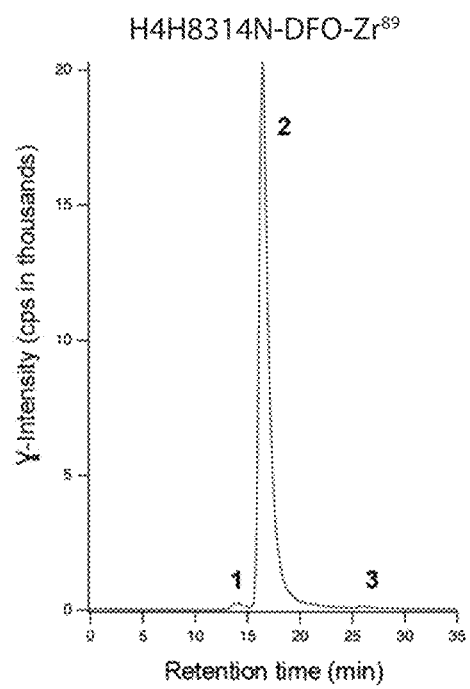
Figure 8F:
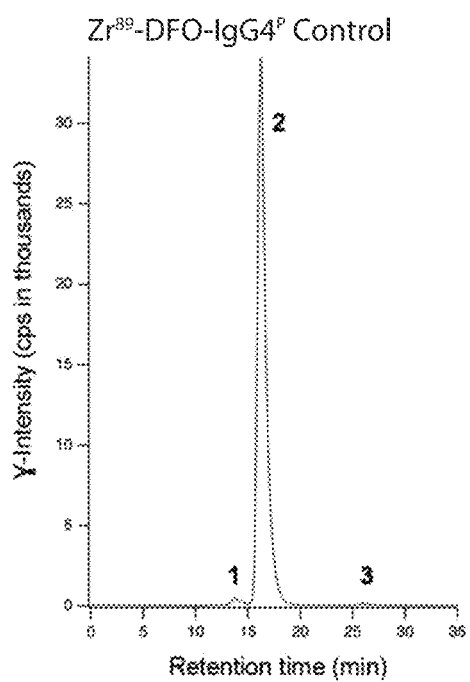

In a second experiment, further comparison between LOX-IMVI and MC38-cOVA/eGFP-mPD-L1$^{-/-}$hPD-L1$^{T}$g was done with or without in vitro treatment by 100 ng/mL of hIFNγ/mIFNγ overnight, respectively. FIG. 7 illustrated that median fluorescence intensity of PD-L1 reached the plateau at ~150 nM of anti-PD-L1 antibody used for staining. At the baseline, PD-L1 expression by LOX-IMVI was moderate (about 6-7 times lower than MC38-cOVA/eGFP-mPD-L1$^{-/-}$hPD-L1$^{Tg}$). Upon treatment with mIFNγ, there was no change for PD-L1 staining on MC38-cOVA/eGFP-mPD-L1$^{-/-}$hPD-L1$^{T}$g, whereas 3-fold increase of human PD-L1 staining was seen in LOX-IMVI after treatment with hIFNγ.

Ex vivo PD-L1 expression by LOX-IMVI and MC38-cOVA/eGFP-mPD-L1$^{-/-}$hPD-L1$^{Tg}$ cells about three weeks post implantation in nude mice were shown in Tables 11 and 12.

TABLE 11

Percentage of PD-L1 positive LOX-IMVI and MC38-cOVA/eGFP-mPD-L1$^{-/-}$hPD-L1$^{Tg}$ cells ~3 weeks post implantation in nude mice

|  | Isotype staining | hPD-L1 staining |
| --- | --- | --- |
| LOX-IMVI | 0.2% | 56.6% |
| MC38-cOVA/eGFP-mPD-L1$^{-/-}$hPD-L1$^{Tg}$ | 0.2% | 96.2% |

TABLE 12

Mean fluorescence intensity of PD-L1 by LOX-IMVI and MC38-cOVA/eGFP-mPD-L1$^{-/-}$hPD-L1$^{Tg}$ cells ~3 weeks post implantation in nude mice

|  | Tumor 1 | Tumor 2 |
| --- | --- | --- |
| LOX-IMVI | 8479.1 | 12121.5 |
| MC38-cOVA/eGFP-mPD-L1$^{-/-}$hPD-L1$^{Tg}$ | 49589.1 | 51445.0 |

Upon enzymatic and mechanical processing to allow for tumor dissociation, cells were stained with the anti-PD-L1 antibody (20 µg/mL). The PD-L1 expression level on LOX-IMVI was about 5 times lower than that on MC38-cOVA/eGFP-mPD-L1$^{-/-}$hPD-L1$^{Tg}$ tumor cells.

Example 6: Selective Localization of Radiolabeled Anti-PD-L1 Antibody to hPD-L1 Positive Tumors in Nude Mice To determine the in vivo localization of anti-PD-L1 antibody, Zirconium-89 labeled DFO-antibody conjugate was administered intravenously to nude mice bearing PD-L1 positive tumors.

The tumor line used for the study was a murine colon carcinoma cell-line referred to as MC38-cOVA/eGFP-mPD-L1$^{-/-}$hPD-L1$^{Tg}$, which has been engineered to knock out murine PD-L1 off the wild type MC38, but over-express full-length human PD-L1 and full-length chicken ovalbumin fused with eGFP. For the second study of tumors with endogenous expression of human PD-L1, the human melanoma cell line LOX-IMVI was used to establish tumors in vivo for subsequent anti-PD-L1 antibody localization studies.

The exemplary radiolabeled anti-PD-L1 antibody used for this study was H1H8314N, comprising HCVR/LCVR of SEQ ID NOs: 82/90.

For the first study, 1×10$^6$ MC38-cOVA/eGFP-mPD-L1−/−hPD-L1$^{Tg}$ cells were implanted subcutaneously into the left flank of male 8-10 week old NCr nude mice (Taconic, Hudson N.Y.). For LOX-IMVI tumors, 1×10$^6$ cells were implanted subcutaneously into the left flank of male 8-10 week old NCr nude mice. Once tumors had reached an average volume of 50-150 mm$^3$ (~Day 7-10), mice were randomized into groups, and dosed with either $^{89}$Zr labeled anti-PD-L1 DFO-antibody conjugate (H1H8314N) or a $^{89}$Zr labeled non-binding isotype control DFO-antibody conjugate. The nude mice bearing MC38-cOVA/eGFP-mPD-L1−/−hPD-L1$^{Tg}$ tumors received 50±1 uCi of $^{89}$Zr labeled antibody with a protein dose ~0.6 mg/kg. In the study using mice bearing LOX-IMVI tumors, mice received 35±1 uCi of $^{89}$Zr labeled antibody with a final antibody dose of 0.3 or 1 mg/kg.

PET imaging of antibody localization was assessed 6 days after administration of the antibodies. A Sofie Biosciences G8 PET/CT (Sofie Biosciences and Perkin Elmer) was used to acquire images). The instrument was pre-calibrated for detection of $^{89}$Zr prior to image acquisition. The energy window ranged from 150 to 650 keV with a reconstructed resolution of 1.4 mm at the center of the field of view. Mice underwent induction anesthesia using isoflurane and were kept under continuous flow of isoflurane during imaging. Static 10-minute images were acquired using the G8 acquisition software and subsequently reconstructed using the pre-configured settings. Image data was corrected for decay and other parameters. CT images were acquired following PET acquisition and later co-registered with the PET images. Images were prepared using VivoQuant post-processing software (inviCRO Imaging Services).

For bio distribution, mice were euthanized at the final time-point (5-6 days post-dosing) and blood was collected via cardiac puncture. Tumors and normal tissues were then excised and placed in counting tubes. Weight for each sample were measured and recorded. Count data for $^{89}$Zr in CPM was then collected by measuring samples on an automatic gamma counter (Wizard 2470, Perkin Elmer). The percent-injected dose per gram (% ID/g) was calculated for each sample using standards prepared from the injected material.

The average % ID/g for each antibody is presented in Table 13.

TABLE 13

Average % ID/g in analyzed tissues

| SAMPLE | $^{89}$Zr-H1H8314N AVERAGE % ID/g | $^{89}$Zr-H1H8314N STDEV % ID/g | $^{89}$Zr-Isotype Control Antibody AVERAGE % ID/g | $^{89}$Zr-Isotype Control Antibody STDEV % ID/g |
|---|---|---|---|---|
| LIVER | 3.1 | 0.4 | 0.9 | 0.9 |
| SPLEEN | 4.4 | 1.1 | 1.5 | 1.3 |
| KIDNEY | 4.0 | 0.7 | 1.4 | 1.6 |

TABLE 13-continued

Average % ID/g in analyzed tissues

| SAMPLE | $^{89}$Zr-H1H8314N AVERAGE % ID/g | $^{89}$Zr-H1H8314N STDEV % ID/g | $^{89}$Zr-Isotype Control Antibody AVERAGE % ID/g | $^{89}$Zr-Isotype Control Antibody STDEV % ID/g |
|---|---|---|---|---|
| BONE | 5.1 | 2.6 | 1.7 | 1.6 |
| LUNG | 5.1 | 1.1 | 2.5 | 3.0 |
| HEART | 2.4 | 0.2 | 1.3 | 1.4 |
| BLOOD | 7.6 | 1.6 | 3.8 | 4.6 |
| THYMUS | 5.3 | 3.0 | 2.8 | 2.2 |
| MC38-cOVA/eGFP-mPD-L1$^{-/-}$hPD-L1$^{Tg}$ | 55.3 | 12.2 | 3.0 | 3.3 |
| S. BOWEL | 1.5 | 0.3 | 0.6 | 0.6 |

From this, the clear high uptake in MC38-cOVA/eGFP-mPD-L1-/-hPD-L1$^{Tg}$ tumors was apparent over other normal tissues, with tumor uptake of 55.3% ID/g being significantly higher than the next highest uptake of 5.3% ID/g observed in the thymus. Tumor uptake was 7.3-fold and 17.8-fold higher than activity in blood and liver, respectively. The specificity of anti-PD-L1 uptake into tumor (55.3% ID/g) was apparent as compared to significantly reduced tumor uptake of 3% observed for the non-binding isotype control antibody. Pilot PET imaging performed here demonstrated a clear localization of the $^{89}$Zr labeled anti-PD-L1 DFO-antibody conjugate to the MC38-cOVA/eGFP-mPD-L1-/-hPD-L1$^{Tg}$ tumors. Little background signal was observed in the animals at this Day 6 post-dosing time-point. In contrast to the clear tumor localization that was apparent using anti-PD-L1 antibody, only faint background activity was apparent in imaging of the control antibody in this model. Imaging clearly indicated high, specific uptake of anti-PD-L1 antibody in human PD-L1 positive tumor, showing the localization of $^{89}$Zr radiolabeled anti-PD-L1 antibody to a MC38-cOVA/eGFP-mPD-L1-/-hPD-L1$^{Tg}$ tumor in an NCr nude mouse.

In a second study, the ability of anti-PD-L1 antibody to selectively target tumors expressing endogenous levels of human PD-L1 antigen was assessed. Here, mice bearing human LOX-IMVI melanoma tumors received $^{89}$Zr labeled antibody at doses of 0.3 and 1 mg/kg. Again, blood, tumor and tissues were taken at Day 6 post-injection and the % ID/g for the samples was calculated. The average % ID/g for each antibody is presented in Table 14.

TABLE 14

Average % ID/G in analyzed tissues from second study (LOX-IMVI tumors)

| SAMPLE | $^{89}$Zr-DFO-H1H8314N 0.3 mg/kg AVERAGE % ID/g | $^{89}$Zr-DFO-H1H8314N 0.3 mg/kg STDEV % ID/g | $^{89}$Zr-DFO-H1H8314N 1 mg/kg AVERAGE % ID/g | $^{89}$Zr-DFO-H1H8314N 1 mg/kg STDEV % ID/g | $^{89}$Zr-Isotype control antibody 1 mg/kg AVERAGE % ID/g | $^{89}$Zr-Isotype control antibody 1 mg/kg STDEV % ID/g |
|---|---|---|---|---|---|---|
| LIVER | 2.9 | 0.3 | 3.3 | 0.2 | 3.9 | 0.3 |
| SPLEEN | 4.2 | 0.2 | 4.3 | 0.9 | 4.2 | 0.7 |
| KIDNEY | 4.3 | 0.4 | 4.3 | 0.8 | 3.4 | 0.4 |
| BONE | 3.2 | 0.6 | 2.7 | 0.5 | 3.6 | 0.4 |
| LUNG | 5.7 | 1.0 | 6.6 | 1.6 | 5.9 | 1.2 |
| HEART | 3.2 | 0.8 | 3.2 | 0.4 | 2.9 | 0.6 |
| BLOOD | 8.1 | 1.4 | 9.5 | 1.0 | 11.1 | 6.2 |
| THYMUS | 5.3 | 2.3 | 5.6 | 0.7 | 4.9 | 1.4 |
| LOX-IMVI TUMOR | 20.6 | 2.7 | 10.6 | 2.6 | 12.0 | 1.8 |
| S.BOWEL | 1.5 | 0.2 | 1.8 | 0.4 | 2.0 | 0.3 |

At the lower 0.3 mg/kg dose, clear targeting to tumor over normal tissues was observed, with a 20.6% ID/g observed in the LOX-IMVI tumors. When mice received the higher 1 mg/kg dose, reduced tumor uptake 10.6% ID/g of was observed relative to the 0.3 mg/kg level. This suggests that the higher protein dose and possibly the subsequent higher fraction of unlabeled antibody led to blocking of tumor uptake by the $^{89}$Zr labeled anti-PD-L1 antibody. In accordance with this, PET imaging conducted immediately prior to the biodistribution study also showed that uptake of anti-PD-L1 antibody at the 1 mg/kg dose was roughly equivalent to that of the control antibody. At the lower dose of 0.3 mg/kg, a clear increase in tumor localization of the anti-PD-L1 antibody was apparent relative to control antibody. Overall, the PET images and the biodistribution data demonstrate specific targeting of the LOX-IMVI tumors at the 0.3 mg/kg dose of anti-PD-L1 antibody.

Example 7: Selective Localization of Radiolabeled Anti-PD-L1 Antibody to hPD-L1 Positive Tumors in Mice This Example describes the in vivo localization of a Zirconium-89 labeled DFO-anti-PD-L1 antibody conjugate in mice humanized for PD-L1. The exemplary antibody used in this Example was H1H8314N, comprising HCVR/LCVR of SEQ ID NOs: 82/90.

Mice humanized for PD-L1 were engineered using VelociGene® technology (Valenzuela et al 2003, Nat. Biotechnol. 21: 652-659; US Patent Application Publication US2016/0157469).

The tumor line used was a murine colon carcinoma cell-line referred to as MC38-cOVA/eGFP-mPD-L1$^{-/-}$hPD-L1$^{Tg}$, engineered in-house to express full-length chicken ovalbumin fused with eGFP and to knock out murine PD-L1 off the wild type MC38, but over-express full-length human PD-L1.

1×10$^6$ cells of MC38-cOVA/eGFP-mPD-L1$^{-/-}$hPD-L1$^{Tg}$ were implanted subcutaneously into the left flank of male humanized PD-L1 mice. Once tumors had reached an average volume of 50-150 mm$^3$ (~Day 7), mice were randomized into groups, and dosed with either $^{89}$Zr labeled anti-PD-L1 DFO-antibody conjugate or a $^{89}$Zr labeled non-binding isotype control DFO-antibody conjugate. The mice received 50±1 uCi of $^{89}$Zr labeled antibody with a final protein dose of 1 or 3 mg/kg.

PET imaging of antibody localization was assessed 6 days after administration of the antibodies. A Sofie Biosciences G8 PET/CT (Sofie Biosciences and Perkin Elmer) was used to acquire images). The instrument was pre-calibrated for detection of $^{89}$Zr prior to image acquisition. The energy window ranged from 150 to 650 keV with a reconstructed resolution of 1.4 mm at the center of the field of view. Mice underwent induction anesthesia using isoflurane and were kept under continuous flow of isoflurane during imaging. Static 10-minute images were acquired using the G8 acquisition software and subsequently reconstructed using the pre-configured settings. Image data was corrected for decay and other parameters. CT images were acquired following PET acquisition and later co-registered with the PET images. Images were prepared using VivoQuant post-processing software (inviCRO Imaging Services).

For biodistribution, mice were euthanized at the final time-point (5-6 days post-dosing) and blood was collected via cardiac puncture. Tumors and normal tissues were then excised and placed in counting tubes. Weight for each sample were measured and recorded. Count data for $^{89}$Zr in CPM was then collected by measuring samples on an automatic gamma counter (Wizard 2470, Perkin Elmer). The percent-injected dose per gram (% ID/g) was calculated for each sample using standards prepared from the injected material.

Results

Humanized PD-L1 mice bearing MC38-cOVA/eGFP-mPD-L1$^{-/-}$hPD-L1$^{Tg}$ tumors received $^{89}$Zr labeled anti-PD-L1 DFO-antibody conjugate at a final antibody dose of 1 or 3 mg/kg. Blood, tumor and tissues were taken and weighed at Day 6 post-injection and the % ID/g for the samples was calculated based on the counts from each sample. The average % ID/g for dose at 1 and 3 mg/kg is presented in Table 15 and Table 16 respectively.

TABLE 15

Average % ID/g in analyzed tissues of anti-PD-L1 antibody at 1 mg/kg

| SAMPLE | AVERAGE % ID/g | STDEV % ID/g |
| --- | --- | --- |
| LIVER | 8.6 | 1.5 |
| SPLEEN | 14.1 | 1.1 |
| KIDNEY | 7.8 | 1.0 |
| BONE | 4.5 | 1.4 |
| LUNG | 7.9 | 3.0 |
| HEART | 4.3 | 1.1 |
| BLOOD | 9.1 | 4.6 |
| THYMUS | 9.7 | 3.5 |
| MC38-cOVA/eGFP-mPD-L1$^{-/-}$hPD-L1$^{Tg}$ | 34.1 | 18.0 |
| S. BOWEL | 2.4 | 0.9 |

At the 1 mg/kg dose level, clear tumor targeting of the MC38-cOVA/eGFP-mPD-L1$^{-/-}$hPD-L1$^{Tg}$ tumors is apparent with a % ID/g of 34.1% despite the expression of PD-L1 in normal tissues in these humanized mice. At this dose, some localization of the $^{89}$Zr labeled anti-PD-L1 antibody was apparent in the spleen, where antibody uptake of 14.1% ID/g was observed. Such uptake is expected because of the normal expression of human PD-L1 in place of mouse PD-L1 expression of human PD-L1 in the spleen. At the 3 mg/kg antibody dose, localization of $^{89}$Zr-DFO-anti-PD-L1 antibody conjugate to the spleen was reduced, as uptake now averaged 9.7% ID/g in mice that received this antibody dose (Table 16).

TABLE 16

Average % ID/g in analyzed tissues of anti-PD-L1 antibody at 3 mg/kg

| SAMPLE | AVERAGE % ID/g | STDEV % ID/g |
| --- | --- | --- |
| LIVER | 6.7 | 1.4 |
| SPLEEN | 9.7 | 1.3 |
| KIDNEY | 7.0 | 1.1 |
| BONE | 3.6 | 0.6 |
| LUNG | 11.0 | 1.0 |
| HEART | 4.7 | 0.7 |
| BLOOD | 12.4 | 2.1 |
| THYMUS | 7.6 | 0.5 |
| MC38-cOVA/eGFP-mPD-L1$^{-/-}$hPD-L1$^{Tg}$ | 28.7 | 13.1 |
| S. BOWEL | 0.4 | 0.2 |

Clear tumor targeting was still observed at the 3 mg/kg dose, with an average of 28.7% ID/g taken up by the MC38-cOVA/eGFP-mPD-L1$^{-/-}$hPD-L1$^{Tg}$ tumors. Therefore although reduced normal tissue localization was apparent in imaging the 3 mg/kg dose, clear localization of anti-PD-L1 labeled antibody to the MC38-cOVA/eGFP-mPD-L1$^{-/-}$hPD-L1$^{Tg}$ tumors remained clear at this dose. Overall, these results indicate that clear targeting of the MC38-cOVA/eGFP-mPD-L1$^{-/-}$hPD-L1$^{Tg}$ tumors was possible in mice expressing PD-L1 on regular sites of normal tissue expression.

The results from the studies performed here clearly demonstrate that anti-PD-L1 antibody labeled with $^{89}$Zr can significantly and specifically localize to tumors. One may envisage a scenario where the anti-PD-L1 antibody is used in the selection of patients with PD-L1 positive tumors for subsequent treatment with inhibitors of the PD-1/PD-L1 signaling axis.

Example 8: Scaled-Up Manufacturing Process for Producing DFO-Anti-PD-L1 Antibody Conjugates This example details the scaled-up manufacturing process for preparing the anti-PD-L1 antibody to be suitable for radiolabeling by attaching p-SCN-bn-Deferoxamine (DFO) to the anti-PD-L1 antibody (mAb, H4H8314N) described herein: (1) ultrafiltration and diafiltration (UFDF) processes prior to mAb conjugation removes excipients that inhibit the conjugation process; (2) following the pre-conjugation UFDF, conjugation of the mAb with p-SCN-Bn-deferoxamine is performed to produce DFO-mAb conjugates; and (3) a post-conjugation UFDF to remove residual salts provides a suitable concentration, excipient level, and pH of the conjugated monoclonal antibody. The resulting DFO-mAb conjugates are then provided in a buffered state with improved stability for subsequent formulation.

(1) Pre-Conjugation Ultrafiltration and Diafiltration (UFDF)

100 g anti-PD-L1 antibody was buffer exchanged into a 5 mM acetate buffer solution having a pH of 5.50 using a Sius Prostream (TangenX Technology Corporation) membrane (membrane capacity of ≤500 g/m²) to remove residual salts prior to conjugation. The process volume was reduced to further concentrate the antibody, then the antibody was sterile filtered using a Sartopore 2 (Sartorius) membrane having a 0.45/0.2 μm (heterogeneous PES double layer) or equivalent pore size. The acetate buffer temperature was kept at a target temperature of 20±5° C. The solutions were well mixed.

(2) Conjugation

The concentrated and filtered antibody (20 g) was transferred into a conjugation vessel containing an amine free carbonate buffer system (56 mM Carbonate, 167 mM Sodium Chloride, pH 9.40) resulting in negligible levels of residual acetate. DFO (25 mM p-SCN-Bn-Deferoxamine) was solubilized in DMSO and added to the conjugation vessel, along with additional DMSO such that the DMSO was present in a final amount of 5%. DFO was added in molar excess at a ratio of 4.5:1 DFO to mAb. The total reaction volume equaled 2.0 L. The buffer system was mixed throughout the addition of the reaction ingredients and throughout the reaction time.

The reaction temperature was controlled for specific time by using an equation which relates temperature to reaction time. In this instance, the reaction temperature was held at 18° C. for 120 minutes. The reaction was quenched by the addition of 2M acetic acid (23 mL/L), resulting in the solution having a pH of 6.

(3) Post-Conjugation UFDF

After the conjugation step, the quenched DFO-mAb conjugation solution was buffer exchanged into histidine buffer (10 mM Histidine, pH 5.50 with 0.0005% (w/v) super refined polysorbate 80 added as a shear protectant) to remove residual process salts, DMSO, and unreacted DFO. Once diafiltered, the solution was then concentrated and subsequently formulated. The histidine buffer was selected for long term storage of protein at −80° C. The same Sius Prostream membrane mentioned in step (1) was used in the final UFDF step. The resulting concentrated DFO-mAb conjugate solution was sterile filtered using the Sartopore 2 filter mentioned above.

UV-DAR (target of 1.5) and protein concentration determination was performed as described in Example 2.

TABLE 17

Molar Extinction Coefficients and Molecular Weight

| Antibody | MW (g mol$^{-1}$) | ε280 (L g$^{-1}$cm$^{-1}$) | ε252 (L g$^{-1}$cm$^{-1}$) |
|---|---|---|---|
| H4H8314N | 144984 | 211480 | 80172 |

Example 9: Predicted Whole Body and Tissue Exposure of Radioactivity in Human Subjects to be Given an IV Dose of $^{89}$Zr-DFO-Anti-PD-L1 Antibody Conjugate The purpose of the following experiment was to estimate the predicted whole body and tissue exposures to radioactivity in human subjects due to an intravenous (IV) dose of $^{89}$Zr-DFO-anti-PD-L1 antibody conjugate. The exemplary anti-PD-L1 antibody used in the radiolabeled conjugate was H4H8314N.

Characterization of Radioimmunoconjugates

Anti-PD-L1 immunoconjugate (DFO-Ab) and isotype control immunoconjugate (DFO-IgG4$^P$ Control) were radiolabeled and purified for use in in vivo imaging and biodistribution studies. SEC-HPLC analysis and a MC38/mPD-L1$^{-/-}$hPD-L1 (murine MC38 colon adenocarcinoma cells engineered to knock out mouse PD-L1 and stably express human PD-L1) cell-based in vitro assay were performed to characterize the resultant radioimmunoconjugates.

Monomeric and Radiochemical Purity

SEC-HPLC using UV- and γ-emission detectors was performed to assess monomeric and radiochemical purity. Results for radioimmunoconjugate preparations of $^{89}$Zr-DFO-anti-PD-L1 antibody conjugate and of isotype control radioimmunoconjugate $^{89}$Zr-DFO-IgG4$^P$ are shown in FIG. 8.

Analysis of chromatograms for absorption at 280 nm was performed to evaluate the relative amounts of high molecular weight (HMW) and monomeric protein in the radioimmunoconjugate preparations. As summarized in Table 18, the monomeric peaks (a readout of monomeric purity) constitute 99.6, 99.2, and 98.6%, respectively, of the total protein peak area for preparations of $^{89}$Zr-DFO-anti-PD-L1 antibody conjugate and isotype control $^{89}$Zr-DFO-IgG4$^P$; low levels of HMW species (0.4, 0.8, and 1.4%, respectively) were also detected. Low molecular weight (LMW) species were not observed for any of the tested samples.

Analysis of radio-chromatograms for γ-emission was performed to evaluate the relative amounts of $^{89}$Zr incorporated into radioimmunoconjugates compared with unincorporated $^{89}$Zr (such as free $^{89}$Zr or $^{89}$Zr chelated with free DFO-derivatives). As summarized in Table 18, the peaks for unincorporated $^{89}$Zr constitute ≤1.1% of the total γ-emission peak area, while the combined peaks for radiolabeled monomeric and HMW species (a readout of radiochemical purity) constitute 98.9, 99.5, and 99.5%, respectively, of the total γ-emission peak area for preparations of $^{89}$Zr-DFO-anti-PD-L1 antibody conjugate and isotype control $^{89}$Zr-DFO-IgG4$^P$.

TABLE 18

Summary of SEC-HPLC Data

| | | | Peak Area (%) | |
|---|---|---|---|---|
| Peak Number | Species | Approximate Retention Time (min) | UV-Chromatogram | Radio-Chromatogram |
| $^{89}$Zr-DFO-H4H8314N Study 1 | | | | |
| 1 | HMW | 13 | 0.4 | 1.1 |
| 2 | Monomer | 16 | 99.6 | 97.8 |
| 3 | Unincorporated $^{89}$Zr | 26 | n/a | 1.1 |
| $^{89}$Zr-DFO-H4H8314N Study 2 | | | | |
| 1 | HMW | 14 | 0.8 | 1.3 |
| 2 | Monomer | 16 | 99.2 | 98.2 |
| 3 | Unincorporated $^{89}$Zr | 26 | n/a | 0.5 |
| $^{89}$Zr-DFO-IgG4$^P$ Control | | | | |
| 1 | HMW | 13 | 1.4 | 1.5 |
| 2 | Monomer | 16 | 98.6 | 98.0 |
| 3 | Unincorporated $^{89}$Zr | 26 | n/a | 0.5 |

Numerical values for SEC-HPLC analysis graphically represented in FIG. 8. UV-chromatogram indicated the chromatogram for absorption at 280 nm and radio-chromatogram indicates the chromatogram for intensity of γ-emission.
HMW: high molecular weight;
n/a: not applicable.

Immunoreactivity

The immunoreactivity, a measure of the percent of radiolabeled, conjugated antibody that is capable of binding its antigen, was determined by incubating $^{89}$Zr-DFO-anti-PD-L1 antibody conjugate with MC38/mPD-L1$^{-/-}$hPD-L1 cells. The 2 tested lots of $^{89}$Zr-DFO-anti-PD-L1 antibody conjugate demonstrated 84.5 and 88.8% immunoreactivity on MC38/mPD-L1$^{-/-}$hPD-L1 cells (Table 19). Background, nonspecific immunoreactivity of 8.8% was observed for the isotype control radioimmunoconjugate.

TABLE 19

Immunoreactivity of $^{89}$Zr labeled anti-PD-L1 DFO-antibody conjugate and isotype control $^{89}$Zr-DFO-IgG4$^P$

| Radioimmunoconjugate | Immunoreactivity |
|---|---|
| $^{89}$Zr-DFO-anti-PD-L1 antibody conjugate (lot 1) | 84.5% |
| $^{89}$Zr-DFO-anti-PD-L1 antibody conjugate (lot 2) | 88.8% |
| isotype control $^{89}$Zr-DFO-IgG4$^P$ | 8.8% |

In conclusion, two separate lots of $^{89}$Zr-DFO-anti-PD-L1 antibody conjugate showed high immunoreactivity, percentage of monomer, and radiochemical purity.

$^{89}$Zr-DFO-anti-PD-L1 Biodistribution in Mice

This experiment evaluated the biodistribution of the anti-human PD-L1 radioimmunoconjugate, $^{89}$Zr-DFO-anti-PD-L1 antibody conjugate, over time following administration of a single 50 µCi (1 mg/kg) intravenous (IV) dose to PD-L1/PD-1-humanized mice (PD-1hu/huPD-L1 hu/hu). Since H4H8314N does not bind mouse PD-L1, the portion of the mouse PD-L1 gene encoding the PD-L1 ectodomain was replaced by the corresponding human sequence in PD-1hu/hu-PD-L1hu/hu mice. In this strain, the ectodomain of mouse PD-1 was similarly humanized. These mice were not subjected to immune/inflammatory challenge, and are therefore expected to have unstimulated levels of PD-L1 expression on immune cells. Two groups of 8 animals each were sacrificed 6 days (144 hours) or 10 days (240 hours) post dosing, blood was collected and the following tissues were harvested: heart, lungs, liver, spleen, kidneys, stomach, small intestine, caecum, large intestine, bone (femur), thymus, muscle, bladder, and brain. The percentage of radioactivity of the total injected dose (% ID) localized to specific tissues or blood was determined and reported as average % ID per gram (% ID/g) of tissue. In advance of sacrifice, immuno-PET/computed tomography (CT) images were acquired 1, 24, 48, 72, 144, 192 (10-day group only), and 240 (10-day group only) hours post dosing from the same animals.

Figure 9:
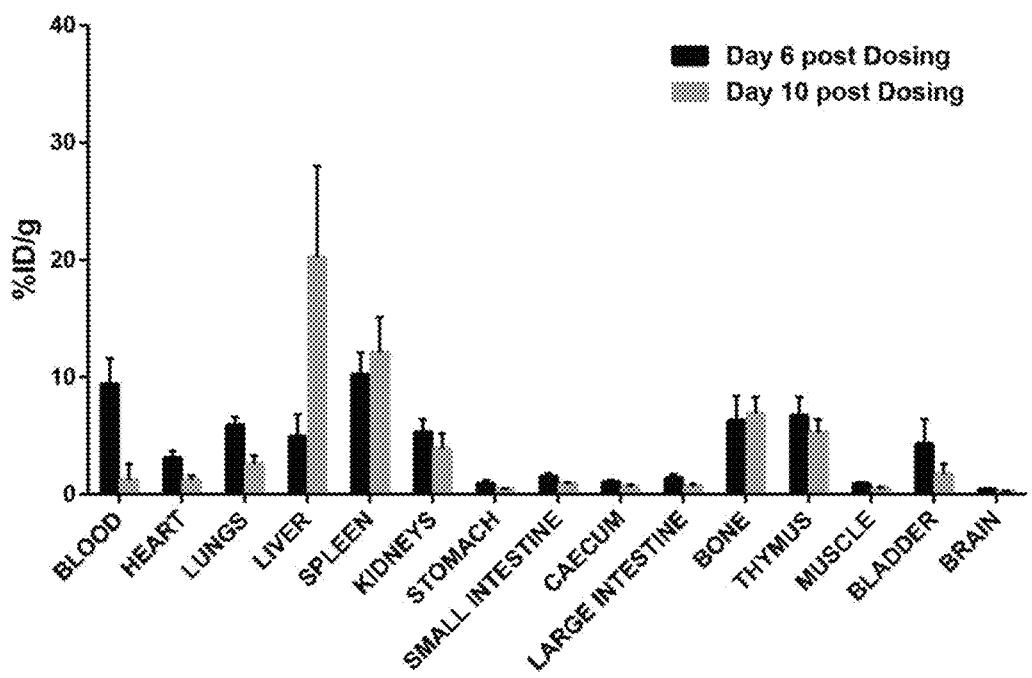
FIG. 9 provides ex vivo biodistribution data for $^{89}$Zr-DFO-anti-PD-L1 antibody conjugate in PD-1hu/hu-PD-L1hu/hu mice. Sixteen mice (2 groups of 8 animals each) were administered a single IV dose of 50 μCi (1 mg/kg) $^{89}$Zr-DFO-anti-PD-L1 antibody conjugate on day 0 and were sacrificed on day 6 (black columns) or day 10 (gray columns) post dosing. Blood, collected via cardiac puncture, and the indicated harvested tissues were weighed and radioactivity was determined. The percent injected dose per gram (% ID/g) values for individual samples collected on day 6 or 10 were calculated relative to the radioactivity of a dose-standard from injected material ($^{89}$Zr-DFO-anti-PD-L1 antibody conjugate) and the weight of the individual samples. Data are plotted as mean±SD.

Relative to $^{89}$Zr levels in blood, uptake of $^{89}$Zr-DFO-anti-PD-L1 antibody conjugate into specific tissues was negligible throughout the 10-day study period, as evaluated by ex vivo tissue analysis (Table 20 and FIG. 9) and in vivo imaging. Compared with blood (9.4±2.2% ID/g), all harvested tissues, with the exception of spleen, demonstrated lower $^{89}$Zr levels (≤6.7% ID/g) on day 6 post dosing. A small degree of target-mediated $^{89}$Zr-DFO-anti-PD-L1 antibody conjugate uptake (10.2±1.9% ID/g) was observed in the spleen, in agreement with PD-L1 expression on splenocytes, as demonstrated by flow cytometry. At 10 days post-dosing, $^{89}$Zr levels in blood had decreased 7.8-fold relative to day 6 post dosing, suggesting a mouse-anti-human antibody (MAHA) response affecting $^{89}$Zr-DFO-anti-PD-L1 antibody conjugate levels. This observed MAHA response is likely due to the fact that the target, PD-L1, is expressed on antigen-presenting cells (Francisco, 2010), leading to the presentation of the human antibody to the mouse immune system and subsequent MAHA formation. In parallel, $^{89}$Zr levels in the liver were 4.1-fold increased on day 10 compared with day 6 post dosing, possibly as a result of MAHA/$^{89}$Zr-DFO-anti-PD-L1 antibody conjugate immune complex (IC) formation and subsequent liver-mediated IC clearance (Rojko, 2014). Whole animal in vivo PET imaging did not uncover marked tissue-specific uptake of $^{89}$Zr-DFO-anti-PD-L1 antibody conjugate beyond a low signal for spleen and the MAHA-mediated accumulation in the liver described above.

In summary, marked target-mediated uptake of $^{89}$Zr-DFO-anti-PD-L1 antibody conjugate into specific tissues above $^{89}$Zr levels in blood was not observed over a 6-day period in PD-L1/PD-1-humanized mice administered a single IV dose of 1 mg/kg (50 µCi) of $^{89}$Zr-DFO-anti-PD-L1 antibody conjugate with the exception of the spleen, where a small degree of target-mediated uptake was observed in agreement with the demonstrated expression of PD-L1 on splenocytes. Data collected beyond day 6 until the end of the study on day 10 post dosing were affected by a MAHA response.

TABLE 20

Average Ex Vivo Biodistribution Data

| Tissue | $^{89}$Zr Levels on Day 6 post Dosing (% ID/g) | | $^{89}$Zr Levels on Day 10 post Dosing (% ID/g) | |
|---|---|---|---|---|
| | Average | SD | Average | SD |
| Blood | 9.4 | 2.2 | 1.2 | 1.4 |
| Heart | 3.1 | 0.6 | 1.2 | 0.4 |
| Lungs | 5.9 | 0.7 | 2.6 | 0.7 |
| Liver | 4.9 | 1.9 | 20.2 | 7.8 |
| Spleen | 10.2 | 1.9 | 12.1 | 3.0 |
| Kidneys | 5.3 | 1.1 | 3.9 | 1.3 |
| Stomach | 0.9 | 0.3 | 0.4 | 0.1 |
| Small Intestine | 1.5 | 0.3 | 0.9 | 0.1 |
| Caecum | 1.0 | 0.2 | 0.6 | 0.2 |
| Large Intestine | 1.4 | 0.3 | 0.7 | 0.2 |
| Bone (Femur) | 6.3 | 2.1 | 6.9 | 1.4 |
| Thymus | 6.7 | 1.6 | 5.3 | 1.1 |
| Muscle | 0.9 | 0.1 | 0.5 | 0.1 |
| Bladder | 4.3 | 2.1 | 1.7 | 0.9 |
| Brain | 0.4 | 0.1 | 0.2 | 0.1 |

Abbreviation:
% ID/g = Percent injected dose per gram (of tissue)

Estimates of Whole Body and Tissue Exposures to Radioactivity in Humans

This experiment used PET/CT image data for four PD-1/PD-L1-humanized male mice and four PD-1/PD-L1-humanized female mice imaged at 1, 24, 48, 72, 144, 192, and 240 hours following single IV administration of 50 µCi (1 mg/kg) of $^{89}$Zr-DFO-anti-PD-L1 antibody conjugate. The data generated by administration of this clinically relevant dose was used in calculating estimates of human exposure to radioactivity. Tissue concentration data was determined using volume of interest (VOI) analysis.

For radiation dosimetry estimation, the mean residence time was determined for the following regions: brain, stomach contents, heart contents, kidneys, liver, lungs, muscle, red marrow, spleen, bladder contents, and remainder of body. These mean residence time values were used as an input into the OLINDA/EXM 1.1 software program to estimate the mean absorbed tissue doses and effective dose in humans.

The effective human dose for $^{89}$Zr-DFO-anti-PD-L1 antibody conjugate was estimated to be 0.513 mSv/MBq (millisievert/megabecquerel) in the adult male and 0.622 mSv/MBq in the adult female. The organs predicted to have the highest absorbed dose in humans were the spleen and liver. The estimated absorbed dose in the spleen was 0.856 mSv/MBq in the adult male and 1.12 mSv/MBq in the adult female. The estimated absorbed dose in the liver was 0.764 mSv/MBq in the adult male and 0.974 mSv/MBq in the adult female.

Average decay-corrected percent of the injected dose per mL (DC % ID/mL) values for male and female mice (n=4 male, n=4 female) for each VOI are summarized in Table 21.

TABLE 21

Biodistribution Data

Average Decay-corrected Percent Injected Dose Per mL (DC % ID/mL) ± SD
Time (h)

| | 1 | | 24 | | 48 |
|---|---|---|---|---|---|
| | Female | Male | Female | Male | Female |
| Brain | 1.365 ± 0.115 | 1.190 ± 0.050 | 0.903 ± 0.115 | 0.538 ± 0.071 | 0.640 ± 0.079 |
| Lungs | 12.503 ± 1.146 | 12.498 ± 0.414 | 8.293 ± 0.635 | 7.155 ± 1.175 | 6.715 ± 0.370 |
| Liver | 12.298 ± 0.664 | 12.078 ± 0.372 | 9.058 ± 0.793 | 7.200 ± 0.499 | 8.113 ± 0.969 |
| Heart | 27.688 ± 1.942 | 25.695 ± 0.934 | 15.685 ± 1.223 | 13.323 ± 1.133 | 12.088 ± 0.883 |
| Kidneys | 11.430 ± 0.387 | 12.100 ± 0.872 | 7.345 ± 0.322 | 6.783 ± 0.811 | 6.418 ± 0.761 |
| Spleen | 15.263 ± 2.166 | 15.860 ± 0.974 | 14.135 ± 2.010 | 11.265 ± 1.706 | 13.675 ± 2.195 |
| Bladder | 6.045 ± 3.910 | 9.688 ± 4.991 | 1.653 ± 0.107 | 1.820 ± 0.283 | 1.443 ± 0.205 |
| Muscle | 1.608 ± 0.182 | 1.435 ± 0.198 | 2.608 ± 0.196 | 1.780 ± 0.137 | 2.368 ± 0.259 |
| Stomach | 3.238 ± 1.063 | 3.978 ± 0.632 | 2.875 ± 0.921 | 3.073 ± 0.566 | 2.478 ± 0.296 |
| Bone | 3.683 ± 1.418 | 3.023 ± 0.244 | 3.310 ± 0.330 | 2.738 ± 0.171 | 4.600 ± 0.511 |

Average Decay-corrected Percent Injected Dose Per mL (DC % ID/mL) ± SD
Time (h)

| | 48 | | 72 | | 144 |
|---|---|---|---|---|---|
| | Male | Female | Male | Female | Male |
| Brain | 0.548 ± 0.218 | 0.685 ± 0.096 | 0.623 ± 0.224 | 0.465 ± 0.231 | 0.398 ± 0.073 |
| Lungs | 5.888 ± 0.990 | 6.060 ± 0.708 | 5.558 ± 0.385 | 4.863 ± 0.316 | 4.585 ± 0.339 |
| Liver | 6.125 ± 0.858 | 7.838 ± 0.932 | 6.203 ± 0.483 | 9.423 ± 1.885 | 6.208 ± 1.428 |
| Heart | 10.25 ± 1.335 | 11.740 ± 1.553 | 9.915 ± 0.171 | 8.140 ± 0.598 | 7.463 ± 0.768 |
| Kidneys | 5.565 ± 0.680 | 6.475 ± 0.493 | 5.568 ± 0.550 | 5.643 ± 0.222 | 4.815 ± 0.450 |
| Spleen | 9.388 ± 1.389 | 13.655 ± 3.606 | 9.920 ± 1.414 | 15.105 ± 2.959 | 10.303 ± 1.102 |
| Bladder | 1.403 ± 0.160 | 1.318 ± 0.108 | 1.710 ± 0.346 | 1.115 ± 0.224 | 1.293 ± 0.430 |
| Muscle | 1.955 ± 0.339 | 2.408 ± 0.181 | 2.148 ± 0.176 | 2.095 ± 0.168 | 1.918 ± 0.144 |
| Stomach | 2.238 ± 0.487 | 2.260 ± 0.306 | 2.233 ± 0.491 | 2.380 ± 0.405 | 1.665 ± 0.148 |
| Bone | 3.493 ± 0.716 | 4.850 ± 1.292 | 4.658 ± 1.399 | 8.993 ± 1.057 | 7.635 ± 0.872 |

Estimated human mean residence time (MRT) values are provided in Table 22 for each of the source organs. MRT in the remainder of the body was obtained by subtracting the sum of all source organ residence times from the reciprocal of the $^{89}$Zr decay constant (Huang et al., Biodistribution, toxicity and radiation dosimetry studies of the serotonin transporter radioligand 4-[18F]-ADAM in rats and monkeys. Eur J Nucl Med Mol Imaging, 2010; 37: 545-555). This represents a conservative estimation of the cumulative tissue radioactivity.

TABLE 22

Human Mean Residence Times (h)

| | Physical Decay[1] | | Biexponential Fit[2] | |
|---|---|---|---|---|
| Organ/Tissue | Female | Male | Female | Male |
| Brain | 0.398 | 0.364 | 0.372 | 0.344 |
| Stomach Contents | 0.511 | 0.476 | 0.492 | 0.480 |
| Heart Contents | 2.433 | 2.279 | 2.290 | 2.154 |
| Kidneys | 0.868 | 0.818 | 0.832 | 0.794 |
| Liver | 5.902 | 5.919 | 8.240 | 5.938 |
| Lungs | 2.508 | 2.772 | 2.411 | 2.642 |
| Muscle | 17.635 | 23.677 | 13.348 | 17.182 |
| Red Marrow | 2.777 | 2.024 | 2.613 | 1.913 |
| Spleen | 0.996 | 0.871 | 1.053 | 0.910 |

TABLE 22-continued

Human Mean Residence Times (h)

| | Physical Decay[1] | | Biexponential Fit[2] | |
|---|---|---|---|---|
| Organ/Tissue | Female | Male | Female | Male |
| Bladder Contents | 0.299 | 0.491 | 0.315 | 0.405 |
| Remainder of Body | 78.794 | 73.430 | 81.157 | 80.361 |

[1]Mean residence time calculated assuming only physical decay following day 6 time point
[2]Mean residence time calculated from a biexponential fit of the data The estimated absorbed tissue doses for all target organs for the OLINDA/EXM 1.1 adult male and adult female phantoms are provided in Table 23. The effective dose, defined by the International Commission on Radiological Protection (ICRP) (International Commission on Radiological Protection. 1990 Recommendations of the International Commission on Radiological Protection. ICRP Publication 60, Pergamon Press, New York, 1991) is a quantity that is calculated by multiplying the absorbed dose for a given organ by a stochastic risk weighting factor and adding the weighted doses together. Estimated effective doses are provided at the end of Table 23. These values represent a conservative estimation of radioactive absorbed doses.

TABLE 23

Estimated Human Tissue Absorbed Doses and Effective Dose

| Organ/Tissue | Physical Decay[1] | | Biexponential Fit[2] | |
|---|---|---|---|---|
| | Adult Male (mSv/MBq) | Adult Female (mSv/MBq) | Adult Male (mSv/MBq) | Adult Female (mSv/MBq) |
| Adrenals | 0.561 | 0.702 | 0.567 | 0.726 |
| Brain | 0.179 | 0.237 | 0.182 | 0.234 |
| Breasts | 0.366 | 0.459 | 0.379 | 0.466 |
| Gallbladder Wall | 0.601 | 0.692 | 0.610 | 0.751 |
| LLI Wall | 0.519 | 0.652 | 0.530 | 0.651 |
| Small Intestine | 0.563 | 0.600 | 0.582 | 0.605 |
| Stomach Wall | 0.575 | 0.714 | 0.584 | 0.718 |
| ULI Wall | 0.553 | 0.685 | 0.571 | 0.700 |
| Heart Wall | 0.789 | 0.973 | 0.781 | 0.964 |
| Kidney | 0.650 | 0.773 | 0.641 | 0.774 |
| Liver | 0.764 | 0.974 | 0.764 | 1.220 |
| Lungs | 0.575 | 0.705 | 0.561 | 0.700 |
| Muscle | 0.396 | 0.481 | 0.381 | 0.464 |
| Ovaries | 0.533 | 0.645 | 0.542 | 0.642 |
| Pancreas | 0.597 | 0.743 | 0.606 | 0.765 |
| Red Marrow | 0.480 | 0.591 | 0.483 | 0.587 |
| Osteogenic Cells | 0.604 | 0.777 | 0.625 | 0.779 |
| Skin | 0.291 | 0.373 | 0.297 | 0.374 |
| Spleen | 0.856 | 1.120 | 0.876 | 1.160 |
| Testes | 0.399 | NA | 0.407 | NA |
| Thymus | 0.481 | 0.605 | 0.484 | 0.601 |
| Thyroid | 0.417 | 0.484 | 0.423 | 0.480 |
| Urinary Bladder Wall | 0.580 | 0.496 | 0.559 | 0.494 |
| Uterus | 0.545 | 0.638 | 0.554 | 0.636 |
| Total Body | 0.440 | 0.550 | 0.440 | 0.554 |
| Effective Dose | 0.513 | 0.622 | 0.516 | 0.625 |

[1] Absorbed doses calculated from MRT assuming only physical decay following day 6 time point
[2] Absorbed doses calculated from MRT with a biexponential fit of the data
Abbreviations:
LLI = lower large intestine,
ULI = upper large intestine,
NA = not applicable The estimated human tissue absorbed doses and effective human dose (Table 23) from the physical decay and the biexponential fit methods were similar. The physical decay method was selected to produce the final set of estimated human tissue absorbed doses and effective dose due to the apparent MAHA response in this murine model. Therefore, the effective human dose for $^{89}$Zr-DFO-anti-PD-L1 antibody conjugate was estimated to be 0.513 mSv/MBq in the adult male and 0.622 mSv/MBq in the adult female. The organs predicted to have the highest absorbed dose in humans are the spleen and liver. The estimated absorbed dose in the spleen was 0.856 mSv/MBq in the adult male and 1.12 mSv/MBq in the adult female. The estimated absorbed dose in the liver was 0.764 mSv/MBq in the adult male and 0.974 mSv/MBq in the adult female.

Example 10: ImmunoPET Imaging of PD-L1 in Tumors Using an $^{89}$Zr-DFO-Anti-PD-L1 Antibody Conjugate in Patients with Advanced Thoracic Malignancies The primary objective of this study is to determine the safety and tolerability of $^{89}$Zr-DFO-anti-PD-L1 antibody conjugate, in which the anti-PD-L1 antibody used in the radiolabeled conjugate is H4H8314N. The secondary objectives of the study are:

Study part A only: To establish adequate mass dose of $^{89}$Zr-DFO-anti-PD-L1 antibody conjugate and optimal post-infusion imaging time, as assessed by imaging and blood draw after tracer infusion.

Study part B only: To establish test/re-test reliability of PET measures as assessed on two separate tracer infusions at optimal mass dose and imaging time point as determined in Part A.

To characterize the pharmacokinetic (PK) profile of $^{89}$Zr-DFO-anti-PD-L1 antibody conjugate based on tracer plasma activity concentration.

This is an open label, 2-part study designed to evaluate the safety and tolerability of $^{89}$Zr-DFO-anti-PD-L1. Study Part A will establish an adequate mass dose and activity dose of $^{89}$Zr-DFO-anti-PD-L1 and an optimal post-infusion imaging time. Test/re-test variability of $^{89}$Zr-DFO-anti-PD-L1 will be evaluated in Part B.

All patients will undergo screening procedures. Patients who meet the eligibility criteria will undergo $^{18}$F-fluorodeoxyglucose ($^{18}$F-FDG) PET/computed tomography (CT) and diagnostic CT scans to assess lesion viability, location, and dimensions. These scans will not be required if adequate quality images are available that were acquired within 28 days of the expected first dose of $^{89}$Zr-DFO-anti-PD-L1.
Part A Three sequential dose cohorts are planned to be treated open-label with $^{89}$Zr-DFO-anti-PD-L1 at 5 mg, 10 mg, or 20 mg.

After infusion with $^{89}$Zr-DFO-anti-PD-L1, patients will undergo $^{89}$Zr-DFO-anti-PD-L1 PET/CT scans on day 1, day 4±1 and day 7±1. Additional imaging may be performed up to day 10. Patients will undergo safety assessments and provide samples for hematology, chemistry, immune safety assays, pharmacokinetics, anti-drug antibody analysis, and biomarker analysis.

Patients will continue to undergo safety evaluations, including physical examination, vital signs, and documentation of Adverse Events (AEs), up to day 21 after the infusion of the $^{89}$Zr-DFO-anti-PD-L1 tracer.

Dose escalation decisions to identify an adequate dose will be informed by safety and tolerability data and by evaluation of immune-positron emission tomography (iPET) positivity and tracer plasma activity concentration, as described below.

Dose Cohorts in Part A

Up to 3 ascending mass dose cohorts are planned. For each mass dose cohort, an initial 2 patients will be dosed, with at a minimum 48-hour interval between the dosing of each patient. Upon completion of the day 7±1 day PET/CT scan for the second patient at a given mass dose, all available imaging, tracer plasma activity concentration, clinical dosimetry, and safety data will be reviewed. Based upon this review, a decision will be made to:

Expand the cohort 6 patients, if there is tumor uptake positivity/tumor localization in at least 1 patient, as defined by a tumor-to-blood ratio>1

Ascend to the next mass dose cohort if there is inadequate tumor uptake and plasma tracer activity concentration, with adequate defined by blood standardized uptake value (SUV) range of 1 to 5 at the optimum imaging time point Proceed with the next mass dose cohort at a lower mass dose, based on inadequate tumor uptake and adequate plasma tracer activity concentration.

If tumor localization is inadequate in at least 2 patients at all three proposed mass dose levels, and this is determined to be due to low image signal-to-noise, the activity dose will be increased up to a maximum of 185 MBq for further expansion of previously tested mass dose cohorts.

Part B

Study Part B will begin once an adequate $^{89}$Zr-DFO-anti-PD-L1 dose and an optimal imaging time have been determined in Part A. On day 1 of Part B, patients will receive the tracer mass dose. Subsequent to receiving the tracer, patients will undergo a scan at the optimal time as identified in Part A. Patients in Part B will receive a second tracer dose and scan after an inter-dose interval of 14 to 28 days. The actual timing of the second tracer dose after the interval will be determined based on results from Part A.

Patients will undergo safety assessments, including physical examination, vital signs, and documentation of adverse events (AEs) during and after visits where $^{89}$Zr-DFO-anti-PD-L1 tracer is administered. During these visits, patients will provide samples for PK, hematology, chemistry, and immune safety assays.

For both Part A and Part B, patients will continue to undergo safety evaluations, including physical examination, vital signs, and documentation of AEs, up to 21 days after the last infusion of the $^{89}$Zr-DFO-anti-PD-L1 tracer.

Study Duration

For Part A, patients will have a screening period of up to 28 days (4 weeks) and a follow-up period of up to 21 days (approximately 3 weeks) after infusion of the tracer dose. The duration of study Part A is approximately 7 weeks, including the screening period.

For Part B, patients will have a screening period of up to 28 days (4 weeks), an inter-infusion interval of up to 28 days (4 weeks), and a 21-day (3 week) safety follow-up period that includes the second scan period. The total duration of the study for each patient will be up to 11 weeks, including the screening period.

The end of study for this study is defined as the last visit of the last patient.

For study Part A, 3 sequential dose levels of up to 6 patients each are planned per cohort, with 3 cohorts planned, for a total of up to 18 patients. For study Part B, up to 10 patients will be enrolled. Enrollment of a maximum of 28 patients in a single study site is planned for the entire study.

Patient Target Population

The target population will consist of patients 18 years of age or older with advanced thoracic malignancies and PD-L1 IHC score on a diagnostic or subsequent biopsy of 1% (positive PD-L1 IHC score by 22C3 PharmDx assay, Dako North America Inc.).

For Part A, the thoracic malignancies will be limited to NSCLC, gastro-esophageal junction adenocarcinoma, and gastric cancer, with PD-L1 score of ≥1% by IHC.

For Part B, all patients with advanced thoracic malignancies and a PD-L1 score of ≥1% by IHC will be eligible. Patients must also have stable disease as per RECIST 1.1 between the two most recent imaging studies.

All patients requiring therapy should be on standard of care therapy.

Treatment $^{89}$Zr-DFO-anti-PD-L1, a radioimmunoconjugate formed by covalently conjugating bifunctional chelator (p-SCN-Bn-DFO) to H4H8314N (anti-PD-L1 monoclonal antibody) and radiolabeling this compound with $^{89}$Zr. $^{89}$Zr-DFO-anti-PD-L1 is supplied in an aqueous buffered vehicle.

For Part A, $^{89}$Zr-DFO-anti-PD-L1 will be administered IV on day 1 (baseline). For Part B, $^{89}$Zr-DFO-anti-PD-L1 will be administered IV on day 1 and day 7±3. Actual timing of the second dose in Part B will be determined from results in Part A.

The $^{89}$Zr-DFO-anti-PD-L1 tracer will be administered at a dose level well below the estimated cumulative exposure levels in humans based on PK models and lower than the levels at which currently available anti-PD-1 agents are used for anti-cancer treatment. This study will exclude patients who are currently treated with anti-PD-L1 to avoid competition for target.

Endpoints

The primary endpoint in the study is the incidence and severity of Treatment-emergent adverse events (TEAEs) through day 21 of the last dose of tracer infusion in patients with thoracic malignancies dosed with $^{89}$Zr-DFO-anti-PD-L1.

For Part A only, the study will establish an adequate mass dose and activity dose of $^{89}$Zr-DFO-anti-PD-L1 and optimal post-infusion imaging time, and the following will be determined via blood drawing and imaging at day 1, 4, and 7 after tracer infusion:

Standardized uptake value of $^{89}$Zr-DFO-anti-PD-L1 in the blood pool, with subsequent calculation of tumor-to-blood ratios at the time of imaging Clinical dosimetry based on the absorbed dose and effective tissue radiation, as calculated from PET image acquisition data and tracer activity concentration in blood Standardized Uptake Values (SUVs) across the tumor regions of interest (ROIs)

Maximal SUVs (SUVmax) within tumor ROIs

Plasma tracer activity concentration, expressed as SUV, with calculation of area under the curve through day 7 ($AUC_{0-7}$)

For Part B only, the study will establish the test/re-test reliability of $^{89}$Zr-DFO-anti-PD-L1 PET measures, and the following will be determined from measures of 2 separate tracer infusions at an adequate mass dose and optimal imaging time points, as determined from Part A:
  Blood pool SUV with subsequent calculation of tumor-to-blood ratio
  SUVs across the tumor ROIs
  SUVmax within the tumor ROIs
  Biodistribution of $^{89}$Zr-DFO-anti-PD-L1
The resulting data will be indicative of the safety and tolerability of $^{89}$Zr-DFO-anti-PD-L1 in humans.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

---

What is claimed is:

1. A radiolabeled antibody conjugate comprising an antibody or antigen binding fragment thereof that binds monomeric human program death ligand 1 (PD-L1), a chelating moiety, and a positron emitter, wherein:
   (i) the antibody or antigen-binding fragment thereof comprises three CDRs within a HCVR of SEQ ID NO: 82; and three CDRs within a LCVR of SEQ ID NO: 90;
   (ii) the chelating moiety comprises desferrioxamine; and
   (iii) the positron emitter is $^{89}$Zr.

2. The conjugate of claim 1, wherein said antibody or antigen-binding fragment thereof is covalently bonded to one or more moieties of formula (A):

-L-Mz         (A)

wherein L is the chelating moiety; M is the positron emitter; and z, independently at each occurrence, is 0 or 1 wherein at least one of z is 1; and wherein -L-M is

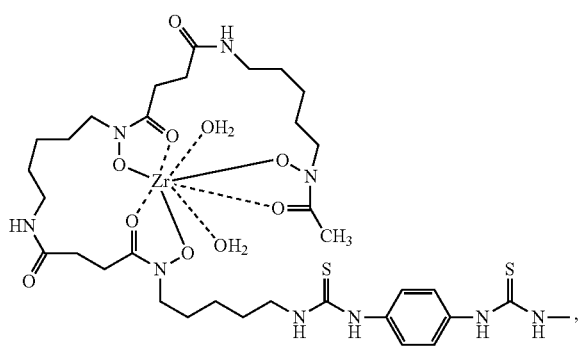

wherein Zr is the positron emitter $^{89}$Zr.

3. The compound of claim 1, wherein antibody or antigen-binding fragment thereof is covalently bonded to one, two, or three moieties of Formula (A).

4. The conjugate of claim 1, wherein the antibody comprises three heavy chain complementarity determining regions, HCDR1, HCDR2, and HCDR3, and three light chain complementarity determining regions, LCDR1, LCDR2, and LCDR3, wherein the HCDR1 comprises the amino acid sequence of SEQ ID NO: 84; the HCDR2 comprises the amino acid sequence of SEQ ID NO: 86; the HCDR3 comprises the amino acid sequence of SEQ ID NO: 88; the LCDR1 comprises the amino acid sequence of SEQ ID NO: 92; the LCDR2 comprises the amino acid sequence of SEQ ID NO: 94; and the LCDR3 comprises the amino acid sequence of SEQ ID NO: 96.

5. A method of imaging a tissue that expresses PD-L1 comprising administering a radiolabeled antibody conjugate of claim 1 to the tissue; and visualizing PD-L1 expression by positron emission tomography (PET) imaging.

6. A radiolabeled antibody conjugate comprising an antibody or antigen binding fragment thereof that binds human program death ligand 1 (PD-L1), a chelating moiety, and a positron emitter, wherein:

(i) the antibody or antigen-binding fragment thereof comprises three heavy chain CDRs (HCDR1, HCDR2, and HCDR3) and three light chain CDRs (LCDR1, LCDR2, and LCDR3), wherein the HCDR1 comprises the amino acid sequence of SEQ ID NO: 84; the HCDR2 comprises the amino acid sequence of SEQ ID NO: 86; the HCDR3 comprises the amino acid sequence of SEQ ID NO: 88; the LCDR1 comprises the amino acid sequence of SEQ ID NO: 92; the LCDR2 comprises the amino acid sequence of SEQ ID NO: 94; and the LCDR3 comprises the amino acid sequence of SEQ ID NO: 96;

(ii) the chelating moiety comprises

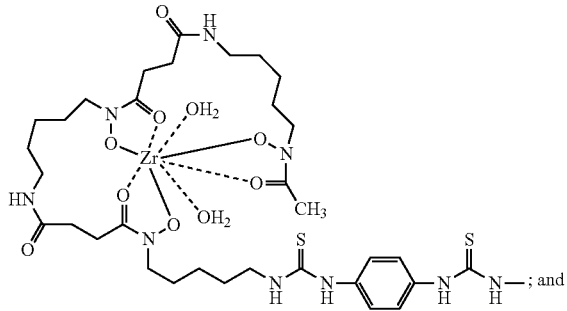

(iii) Zr is the positron emitter $^{89}$Zr.

SEQUENCE LISTING

```
<160> NUMBER OF SEQ ID NOS: 344

<210> SEQ ID NO 1
<211> LENGTH: 363
<212> TYPE: DNA
<213> ORGANISM: Artificial Sequence
<220> FEATURE:
<223> OTHER INFORMATION: synthetic

<400> SEQUENCE: 1
gaggtgcagc tggtggagtc tgggggaggc ttggtccagc ctgggggtc cctgagactc        60 tcctgtgcag cctctggatt cacctttagt aggttttgga tgagctgggt ccgccaggct      120
ccagggaagg ggctggagtg ggtggccaac ataaaccaag atggaactga aaatactat       180 gtggactctg tgaagggccg attcaccatc tccagagaca acgccaagaa ctcactgtat      240
ctgcaaatga acagcctgag agccggggac acggctgtgt attactgtgc gaatacgtat      300
tacgattttt ggagtggtca ctttgactac tggggccagg gaaccctggt caccgtctcc      360
tca                                                                    363

<210> SEQ ID NO 2
<211> LENGTH: 121
<212> TYPE: PRT
<213> ORGANISM: Artificial Sequence
<220> FEATURE:
<223> OTHER INFORMATION: synthetic

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Phe
            20                  25                  30

Trp Met Ser Trp Val Arg Gln Ala Pro Gly Lys Gly Leu Glu Trp Val
        35                  40                  45

Ala Asn Ile Asn Gln Asp Gly Thr Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Gly Asp Thr Ala Val Tyr Tyr Cys
                85                  90                  95

Ala Asn Thr Tyr Tyr Asp Phe Trp Ser Gly His Phe Asp Tyr Trp Gly
            100                 105                 110

Gln Gly Thr Leu Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: synthetic
```

<400> SEQUENCE: 3
ggattcacct ttagtaggtt ttgg                                                24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Ser Arg Phe Trp
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
ataaaccaag atggaactga gaaa                                                24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Asn Gln Asp Gly Thr Glu Lys
1               5

<210> SEQ ID NO 7
<211> LENGTH: 42
<212> TYPE: DNA
<213> ORGANISM: Artificial Sequence
<220> FEATURE:
<223> OTHER INFORMATION: synthetic

<400> SEQUENCE: 7
gcgaatacgt attacgattt ttggagtggt cactttgact ac                            42

<210> SEQ ID NO 8
<211> LENGTH: 14
<212> TYPE: PRT
<213> ORGANISM: Artificial Sequence
<220> FEATURE:
<223> OTHER INFORMATION: synthetic

<400> SEQUENCE: 8

Ala Asn Thr Tyr Tyr Asp Phe Trp Ser Gly His Phe Asp Tyr
1               5                   10

<210> SEQ ID NO 9
<211> LENGTH: 321
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccttccacc ctgtctgcat ctgtaggaga cagagtcacc         60

```
atcacttgtc gggccagtca gagtattagt aattggttgg cctggtatca gcagaaacca      120
gggaaagccc ctaagctcct gatctataag gcgtctagtt tagaaagtgg ggtcccatca      180
aggttcagcg gcagtggatc tgggacagaa ttcactctca ccatcagcag cctgcagcct      240
gatgattttg caacttatta ctgccaacag tatcatagtt attcgtacac ttttggccag      300
gggaccaagc tggagatcaa a                                                321
```

<210> SEQ ID NO 10
<211> LENGTH: 107
<212> TYPE: PRT
<213> ORGANISM: Artificial Sequence
<220> FEATURE:
<223> OTHER INFORMATION: synthetic

<400> SEQUENCE: 10

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Tyr Ser Tyr
                85                  90                  95

Thr Phe Gly Gln Gly Thr Lys Leu Glu Ile Lys
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11

```
cagagtatta gtaattgg                                                     18
```

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

```
Gln Ser Ile Ser Asn Trp
1               5
```

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13

```
aaggcgtct                                                                9
```

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Lys Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
caacagtatc atagttattc gtacact                                       27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Tyr His Ser Tyr Ser Tyr Thr
1               5

<210> SEQ ID NO 17
<211> LENGTH: 363
<212> TYPE: DNA
<213> ORGANISM: Artificial Sequence
<220> FEATURE:
<223> OTHER INFORMATION: synthetic

<400> SEQUENCE: 17
caggagcacc tggtggagtc tgggggaggc gtggtccagc ctgggaggtc cctgagactc     60
tcctgtgaag cgtctggatt caccttcagt aactttggca tgcactgggt ccgccaggct    120
ccaggcaagg ggctggagtg ggtggcagct ttatggtctg atggaagtaa taaatactat    180
gcagactccg tgaagggtcg agtcaccatc tccagagaca attccaagaa cacactgtat    240
ctgcaaatga acagcctgag agccgaggac acggctgtct attactgtgc gagagggaga    300 ggagccccg gtattccgat ttttgggtac tggggccagg aaccctggt caccgtctcc    360 tca                                                                 363

<210> SEQ ID NO 18
<211> LENGTH: 121
<212> TYPE: PRT
<213> ORGANISM: Artificial Sequence
<220> FEATURE:
<223> OTHER INFORMATION: synthetic

<400> SEQUENCE: 18

Gln Glu His Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Asn Phe
            20                  25                  30

Gly Met His Trp Val Arg Gln Ala Pro Gly Lys Gly Leu Glu Trp Val

```
            35                  40                  45
Ala Ala Leu Trp Ser Asp Gly Ser Asn Lys Tyr Tyr Ala Asp Ser Val
    50                  55                  60

Lys Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Gly Ala Pro Gly Ile Pro Ile Phe Gly Tyr Trp Gly
            100                 105                 110

Gln Gly Thr Leu Val Thr Val Ser Ser
            115                 120
```

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct tcagtaactt tggc                                          24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Phe Thr Phe Ser Asn Phe Gly
1               5

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
ttatggtctg atggaagtaa taaa                                          24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Leu Trp Ser Asp Gly Ser Asn Lys
1               5

<210> SEQ ID NO 23
<211> LENGTH: 42
<212> TYPE: DNA
<213> ORGANISM: Artificial Sequence
<220> FEATURE:
<223> OTHER INFORMATION: synthetic

<400> SEQUENCE: 23
gcgagaggga gaggagcccc cggtattccg attttttgggt ac                     42

<210> SEQ ID NO 24
<211> LENGTH: 14
<212> TYPE: PRT
<213> ORGANISM: Artificial Sequence
<220> FEATURE:
<223> OTHER INFORMATION: synthetic

<400> SEQUENCE: 24

Ala Arg Gly Arg Gly Ala Pro Gly Ile Pro Ile Phe Gly Tyr
1               5                   10

<210> SEQ ID NO 25
<211> LENGTH: 321
<212> TYPE: DNA
<213> ORGANISM: Artificial Sequence
<220> FEATURE:
<223> OTHER INFORMATION: synthetic

<400> SEQUENCE: 25
gacatccaga tgacccagtc tccatcctcc ctgtctgcat ctgttggaga cagagtcacc    60
atcacttgcc gggcaagtca gggcattaga aatgatttag gctggtatca gcagaaacca   120
gggaaagccc ctaagcgcct gatctatact gcatccagtt tgcaaagtgg ggtcccatca   180
agattcagcg gcagtggatc tgggacagaa ttcactctca caatcagcag cctacagcct   240
gaagattttg caacttatta ctgtctacaa cataatagtt accctctcac attcggcgga   300
gggaccaagg tggcgatcaa a                                             321

<210> SEQ ID NO 26
<211> LENGTH: 107
<212> TYPE: PRT
<213> ORGANISM: Artificial Sequence
<220> FEATURE:
<223> OTHER INFORMATION: synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Ala Ile Lys
            100                 105

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagggcatta gaaatgat                                                  18

```
<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

Gln Gly Ile Arg Asn Asp
1               5

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 actgcatcc                                                                 9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Thr Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
ctacaacata atagttaccc tctcaca                                             27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Leu Gln His Asn Ser Tyr Pro Leu Thr
1               5

<210> SEQ ID NO 33
<211> LENGTH: 390
<212> TYPE: DNA
<213> ORGANISM: Artificial Sequence
<220> FEATURE:
<223> OTHER INFORMATION: synthetic

<400> SEQUENCE: 33
gaggtgcagc tggtggagtc tgggggaggc ttggtaaagc ctggggggtc ccttagactc          60
tcctgtgcag cctctggatt cactttcagt aacgcctgga tgagctgggt ccgccaggct         120
ccagggaagg ggctggagtg ggttggccgt attaaaagga aaactgatgg tgggacaaca         180
gactacgctg cacccgtgaa aggcagattc accatctcaa gagatgattc aaaaaatacg         240
```
ctgcatctgc aaatgaacag cctgaaaacc gaggacacag ccgtgtatta ctgtaccaca    300
gatgatattg tagttgtacc agctgttatg agggaatact acttcggtat ggacgtctgg    360
ggccaaggga ccacggtcac cgtctcctca                                     390

<210> SEQ ID NO 34
<211> LENGTH: 130
<212> TYPE: PRT
<213> ORGANISM: Artificial Sequence
<220> FEATURE:
<223> OTHER INFORMATION: synthetic

<400> SEQUENCE: 34

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Arg Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu His Leu Gln Met Asn Ser Leu Lys Thr Glu Asp Thr Ala Val Tyr
                85                  90                  95

Tyr Cys Thr Thr Asp Asp Ile Val Val Val Pro Ala Val Met Arg Glu
            100                 105                 110

Tyr Tyr Phe Gly Met Asp Val Trp Gly Gln Gly Thr Thr Val Thr Val
        115                 120                 125

Ser Ser
    130

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggattcactt tcagtaacgc ctgg                                            24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Phe Thr Phe Ser Asn Ala Trp
1               5

<210> SEQ ID NO 37
<211> LENGTH: 30
<212> TYPE: DNA
<213> ORGANISM: Artificial Sequence
<220> FEATURE:
<223> OTHER INFORMATION: synthetic

<400> SEQUENCE: 37

-continued attaaaagga aaactgatgg tgggacaaca    30

<210> SEQ ID NO 38
<211> LENGTH: 10
<212> TYPE: PRT
<213> ORGANISM: Artificial Sequence
<220> FEATURE:
<223> OTHER INFORMATION: synthetic

<400> SEQUENCE: 38

Ile Lys Arg Lys Thr Asp Gly Gly Thr Thr
1               5                   10

<210> SEQ ID NO 39
<211> LENGTH: 63
<212> TYPE: DNA
<213> ORGANISM: Artificial Sequence
<220> FEATURE:
<223> OTHER INFORMATION: synthetic

<400> SEQUENCE: 39
accacagatg atattgtagt tgtaccagct gttatgaggg aatactactt cggtatggac    60
gtc    63

<210> SEQ ID NO 40
<211> LENGTH: 21
<212> TYPE: PRT
<213> ORGANISM: Artificial Sequence
<220> FEATURE:
<223> OTHER INFORMATION: synthetic

<400> SEQUENCE: 40

Thr Thr Asp Asp Ile Val Val Val Pro Ala Val Met Arg Glu Tyr Tyr
1               5                   10                  15

Phe Gly Met Asp Val
            20

<210> SEQ ID NO 41
<211> LENGTH: 321
<212> TYPE: DNA
<213> ORGANISM: Artificial Sequence
<220> FEATURE:
<223> OTHER INFORMATION: synthetic

<400> SEQUENCE: 41
gacatccaga tgacccagtc tccatcctcc ctgtctgcat ctgtaggaga cagagtcacc    60
atcacttgcc ggacaagtca gggcattaga aatgatttag ctggtatca gcagaaacca   120 gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataataatt acccgtacac ttttggccag   300
gggaccaagc tggagatcaa a    321

<210> SEQ ID NO 42
<211> LENGTH: 107
<212> TYPE: PRT
<213> ORGANISM: Artificial Sequence
<220> FEATURE:
<223> OTHER INFORMATION: synthetic

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Tyr
                85                  90                  95

Thr Phe Gly Gln Gly Thr Lys Leu Glu Ile Lys
            100                 105

```
<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43
cagggcatta gaaatgat                                                 18

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44
```

Gln Gly Ile Arg Asn Asp
1               5

```
<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 gctgcatcc                                                            9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46
```

Ala Ala Ser
1

```
<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
```

```
ctacagcata ataattaccc gtacact                                              27
```

<210> SEQ ID NO 48
<211> LENGTH: 9
<212> TYPE: PRT
<213> ORGANISM: Artificial Sequence
<220> FEATURE:
<223> OTHER INFORMATION: synthetic

<400> SEQUENCE: 48

Leu Gln His Asn Asn Tyr Pro Tyr Thr
1               5

<210> SEQ ID NO 49
<211> LENGTH: 363
<212> TYPE: DNA
<213> ORGANISM: Artificial Sequence
<220> FEATURE:
<223> OTHER INFORMATION: synthetic

<400> SEQUENCE: 49

```
caggtgcaat tggtgcagtc tggggcggag gtgaagaagc ctggggcctc agtgcaggtc    60
tcctgcaagg cttctggata ctccttcacc ggctactata tacactgggt gcgacaggcc   120
cctggacaag gacttgagtg gatgggatgg atcaacccta acagtggcac caaaaagtat   180
gcacacaagt tccagggcag ggtcaccatg accaggaca cgtccatcga cacagcctac   240
atgattttga gcagtctgat atccgacgac acggccgtgt attactgtgc gagagatgag   300
gactggaact ttgggagctg gttcgactcc tggggccagg gaaccctggt caccgtctcc   360
tca                                                                 363
```

<210> SEQ ID NO 50
<211> LENGTH: 121
<212> TYPE: PRT
<213> ORGANISM: Artificial Sequence
<220> FEATURE:
<223> OTHER INFORMATION: synthetic

<400> SEQUENCE: 50

Gln Val Gln Leu Val Gln Ser Gly Ala Glu Val Lys Lys Pro Gly Ala
1               5                   10                  15

Ser Val Gln Val Ser Cys Lys Ala Ser Gly Tyr Ser Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Thr Lys Lys Tyr Ala His Lys Phe
    50                  55                  60

Gln Gly Arg Val Thr Met Thr Arg Asp Thr Ser Ile Asp Thr Ala Tyr
65                  70                  75                  80

Met Ile Leu Ser Ser Leu Ile Ser Asp Asp Thr Ala Val Tyr Tyr Cys
                85                  90                  95

Ala Arg Asp Glu Asp Trp Asn Phe Gly Ser Trp Phe Asp Ser Trp Gly
            100                 105                 110

Gln Gly Thr Leu Val Thr Val Ser Ser
        115                 120

<210> SEQ ID NO 51
<211> LENGTH: 24
<212> TYPE: DNA
<213> ORGANISM: Artificial Sequence
<220> FEATURE:

<223> OTHER INFORMATION: synthetic

<400> SEQUENCE: 51
ggatactcct tcaccggcta ctat            24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Tyr Ser Phe Thr Gly Tyr Tyr
1               5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
atcaacccta acagtggcac caaa            24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Asn Pro Asn Ser Gly Thr Lys
1               5

<210> SEQ ID NO 55
<211> LENGTH: 42
<212> TYPE: DNA
<213> ORGANISM: Artificial Sequence
<220> FEATURE:
<223> OTHER INFORMATION: synthetic

<400> SEQUENCE: 55
gcgagagatg aggactggaa ctttgggagc tggttcgact cc            42

<210> SEQ ID NO 56
<211> LENGTH: 14
<212> TYPE: PRT
<213> ORGANISM: Artificial Sequence
<220> FEATURE:
<223> OTHER INFORMATION: synthetic

<400> SEQUENCE: 56

Ala Arg Asp Glu Asp Trp Asn Phe Gly Ser Trp Phe Asp Ser
1               5                   10

<210> SEQ ID NO 57
<211> LENGTH: 336
<212> TYPE: DNA
<213> ORGANISM: Artificial Sequence
<220> FEATURE:
<223> OTHER INFORMATION: synthetic

<400> SEQUENCE: 57

```
gatattgtga tgacccagac tccactctcc tcacctgtca cccttggaca gccggcctcc    60
atctcctgca ggtctagtca aaccctcgta cacggtgatg aaacacgta cttgagttgg   120 attcagcaga ggccaggcca gcctccgaga ctcctcattt ataaggtttc taatcagttc   180
tctggggtcc cagacagatt cagtggcagt ggggcaggga cagatttcac actgaaaatc   240
agcagggtgg aagctgagga tgtcgggctt tatttctgca tgcaagctac acattttccg   300
atcaccttcg ccaagggac acgactggag attaaa                              336
```

<210> SEQ ID NO 58
<211> LENGTH: 112
<212> TYPE: PRT
<213> ORGANISM: Artificial Sequence
<220> FEATURE:
<223> OTHER INFORMATION: synthetic

<400> SEQUENCE: 58

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Thr Leu Val His Gly
            20                  25                  30

Asp Gly Asn Thr Tyr Leu Ser Trp Ile Gln Gln Arg Pro Gly Gln Pro
        35                  40                  45

Pro Arg Leu Leu Ile Tyr Lys Val Ser Asn Gln Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Leu Tyr Phe Cys Met Gln Ala
                85                  90                  95

Thr His Phe Pro Ile Thr Phe Gly Gln Gly Thr Arg Leu Glu Ile Lys
            100                 105                 110
```

<210> SEQ ID NO 59
<211> LENGTH: 33
<212> TYPE: DNA
<213> ORGANISM: Artificial Sequence
<220> FEATURE:
<223> OTHER INFORMATION: synthetic

<400> SEQUENCE: 59

```
caaaccctcg tacacggtga tggaaacacg tac                                 33
```

<210> SEQ ID NO 60
<211> LENGTH: 11
<212> TYPE: PRT
<213> ORGANISM: Artificial Sequence
<220> FEATURE:
<223> OTHER INFORMATION: synthetic

<400> SEQUENCE: 60

```
Gln Thr Leu Val His Gly Asp Gly Asn Thr Tyr
1               5                   10
```

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61

```
aaggtttct                                                             9
```

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Lys Val Ser
1

<210> SEQ ID NO 63
<211> LENGTH: 27
<212> TYPE: DNA
<213> ORGANISM: Artificial Sequence
<220> FEATURE:
<223> OTHER INFORMATION: synthetic

<400> SEQUENCE: 63
atgcaagcta cacattttcc gatcacc                                          27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Met Gln Ala Thr His Phe Pro Ile Thr
1               5

<210> SEQ ID NO 65
<211> LENGTH: 363
<212> TYPE: DNA
<213> ORGANISM: Artificial Sequence
<220> FEATURE:
<223> OTHER INFORMATION: synthetic

<400> SEQUENCE: 65
caggtacacc tggtgcagtc tggggctgag gtgaagaagc ctggggcctc agtgaaggtc        60
tcctgcaagg cttctggata caccttcacc ggctactata cattgggt gcgacaggcc        120 cctggacacg gcttgagtg gatgggatgg ctcaaccta atactggtac acaaagtat        180 atacagaact ttcagggcag ggtcaccatg accagggaca cgtccagcag cacagcctac        240
atggagctga ccaggctgag atctgacgac acggccgtgt attactgtgc gagagatgag        300
gactggaatt atgggagctg gttcgacacc tggggccagg gaaccctggt cacagtctcc        360
tca                                                                   363

<210> SEQ ID NO 66
<211> LENGTH: 121
<212> TYPE: PRT
<213> ORGANISM: Artificial Sequence
<220> FEATURE:
<223> OTHER INFORMATION: synthetic

<400> SEQUENCE: 66

Gln Val His Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly His Gly Leu Glu Trp Met
            35                  40                  45

Gly Trp Leu Asn Pro Asn Thr Gly Thr Thr Lys Tyr Ile Gln Asn Phe
 50                  55                  60

Gln Gly Arg Val Thr Met Thr Arg Asp Thr Ser Ser Thr Ala Tyr
 65                  70                  75                  80

Met Glu Leu Thr Arg Leu Arg Ser Asp Thr Ala Val Tyr Tyr Cys
                85                  90                  95

Ala Arg Asp Glu Asp Trp Asn Tyr Gly Ser Trp Phe Asp Thr Trp Gly
            100                 105                 110

Gln Gly Thr Leu Val Thr Val Ser Ser
        115                 120

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
ggatacacct tcaccggcta ctat                                          24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Tyr Thr Phe Thr Gly Tyr Tyr
 1               5

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
ctcaacccta atactggtac caca                                          24

<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

Leu Asn Pro Asn Thr Gly Thr Thr
 1               5

<210> SEQ ID NO 71
<211> LENGTH: 42
<212> TYPE: DNA
<213> ORGANISM: Artificial Sequence
<220> FEATURE:
<223> OTHER INFORMATION: synthetic

<400> SEQUENCE: 71
gcgagagatg aggactggaa ttatgggagc tggttcgaca cc                      42

<210> SEQ ID NO 72
<211> LENGTH: 14
<212> TYPE: PRT
<213> ORGANISM: Artificial Sequence
<220> FEATURE:
<223> OTHER INFORMATION: synthetic

<400> SEQUENCE: 72

```
Ala Arg Asp Glu Asp Trp Asn Tyr Gly Ser Trp Phe Asp Thr
1               5                   10
```

<210> SEQ ID NO 73
<211> LENGTH: 336
<212> TYPE: DNA
<213> ORGANISM: Artificial Sequence
<220> FEATURE:
<223> OTHER INFORMATION: synthetic

<400> SEQUENCE: 73

```
gatattgtaa tgacccagac tccactctcc tcacctgtca cccttggaca gccggcctcc      60
atctcctgca ggtctagtcc aagcctcgta cacagtgatg gaaacaccta cttgagttgg     120
cttcagcaga ggccaggcca gcctccaaga ctcctaattt ataagatttc taaccgattc     180
tctggggtcc cagacagatt cagtggcagt ggggcaggga cagatttcac gctgaaaatc     240
agcagggtgg aagctgagga tgtcggggtt tattactgca tgcaagctac acattttccg     300
atcaccttcg gccaagggac acgactggag attaga                               336
```

<210> SEQ ID NO 74
<211> LENGTH: 112
<212> TYPE: PRT
<213> ORGANISM: Artificial Sequence
<220> FEATURE:
<223> OTHER INFORMATION: synthetic

<400> SEQUENCE: 74

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Pro Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Phe Pro Ile Thr Phe Gly Gln Gly Thr Arg Leu Glu Ile Arg
            100                 105                 110
```

<210> SEQ ID NO 75
<211> LENGTH: 33
<212> TYPE: DNA
<213> ORGANISM: Artificial Sequence
<220> FEATURE:
<223> OTHER INFORMATION: synthetic

<400> SEQUENCE: 75

```
ccaagcctcg tacacagtga tggaaacacc tac                                   33
```

<210> SEQ ID NO 76
<211> LENGTH: 11
<212> TYPE: PRT
<213> ORGANISM: Artificial Sequence
<220> FEATURE:
<223> OTHER INFORMATION: synthetic

<400> SEQUENCE: 76

```
Pro Ser Leu Val His Ser Asp Gly Asn Thr Tyr
1               5                   10
```

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 aagatttct                                                                 9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

```
Lys Ile Ser
1
```

<210> SEQ ID NO 79
<211> LENGTH: 27
<212> TYPE: DNA
<213> ORGANISM: Artificial Sequence
<220> FEATURE:
<223> OTHER INFORMATION: synthetic

<400> SEQUENCE: 79
atgcaagcta cacattttcc gatcacc                                            27

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

```
Met Gln Ala Thr His Phe Pro Ile Thr
1               5
```

<210> SEQ ID NO 81
<211> LENGTH: 360
<212> TYPE: DNA
<213> ORGANISM: Artificial Sequence
<220> FEATURE:
<223> OTHER INFORMATION: synthetic

<400> SEQUENCE: 81
gaggtgcagc tggtggaatc tgggggaggt gtggtgcggc ctgggggggtc cctgagactc        60 tcctgtgcag cctctggatt cacttttgat gattatggca tgacctgggt ccgccaagct       120
ccagggaggg gcctggaatg ggtctctggt attcattggc atggtaaacg cacaggttat       180

```
gcagactctg tgaagggccg attcaccata tccagagaca acgccaagaa atccctgtat    240
ctgcaaatga acagtctgaa aggcgaggac acggccttgt atcattgtgt gaggggggga    300
atgagtacag gggactggtt cgaccnctgg ggccaggaa ccctggtcat cgtctcctca     360
```

<210> SEQ ID NO 82
<211> LENGTH: 120
<212> TYPE: PRT
<213> ORGANISM: Artificial Sequence
<220> FEATURE:
<223> OTHER INFORMATION: synthetic

<400> SEQUENCE: 82

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Thr Trp Val Arg Gln Ala Pro Gly Arg Gly Leu Glu Trp Val
        35                  40                  45

Ser Gly Ile His Trp His Gly Lys Arg Thr Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Lys Gly Glu Asp Thr Ala Leu Tyr His Cys
                85                  90                  95

Val Arg Gly Gly Met Ser Thr Gly Asp Trp Phe Asp Pro Trp Gly Gln
            100                 105                 110

Gly Thr Leu Val Ile Val Ser Ser
        115                 120
```

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83

```
ggattcactt ttgatgatta tggc                                           24
```

<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

```
Gly Phe Thr Phe Asp Asp Tyr Gly
1               5
```

<210> SEQ ID NO 85
<211> LENGTH: 24
<212> TYPE: DNA
<213> ORGANISM: Artificial Sequence
<220> FEATURE:
<223> OTHER INFORMATION: synthetic

<400> SEQUENCE: 85

```
attcattggc atggtaaacg caca                                           24
```

<210> SEQ ID NO 86

```
<211> LENGTH: 8
<212> TYPE: PRT
<213> ORGANISM: Artificial Sequence
<220> FEATURE:
<223> OTHER INFORMATION: synthetic

<400> SEQUENCE: 86

Ile His Trp His Gly Lys Arg Thr
1               5

<210> SEQ ID NO 87
<211> LENGTH: 39
<212> TYPE: DNA
<213> ORGANISM: Artificial Sequence
<220> FEATURE:
<223> OTHER INFORMATION: synthetic

<400> SEQUENCE: 87 gtgaggggg gaatgagtac agggactgg ttcgacccc                            39

<210> SEQ ID NO 88
<211> LENGTH: 13
<212> TYPE: PRT
<213> ORGANISM: Artificial Sequence
<220> FEATURE:
<223> OTHER INFORMATION: synthetic

<400> SEQUENCE: 88

Val Arg Gly Gly Met Ser Thr Gly Asp Trp Phe Asp Pro
1               5                   10

<210> SEQ ID NO 89
<211> LENGTH: 324
<212> TYPE: DNA
<213> ORGANISM: Artificial Sequence
<220> FEATURE:
<223> OTHER INFORMATION: synthetic

<400> SEQUENCE: 89
gacatccaga tgacccagtc tccatcctcc ctgtctgcat ctctaggaga cagagtcacc    60
atcacttgcc gggcaagtca gagcattaac agttatttaa attggtatca gcagaaacca   120
gggaaagccc ctaaactcct gatctatgtt gcatccagtt tgcaaagtgg ggtcccatca   180
aggttcagtg gcagtggatc tgggacagaa ttcactctca ccatcagcaa tctgcaacct   240
gaagattttg caacttacta ctgtcaacag agttacagta cccctccgat caccttcggc   300
caagggacac gactggagat taaa                                          324

<210> SEQ ID NO 90
<211> LENGTH: 108
<212> TYPE: PRT
<213> ORGANISM: Artificial Sequence
<220> FEATURE:
<223> OTHER INFORMATION: synthetic

<400> SEQUENCE: 90

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60
```

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: synthetic

<400> SEQUENCE: 91
cagagcatta acagttat                                               18

<210> SEQ ID NO 92
<211> LENGTH: 6
<212> TYPE: PRT
<213> ORGANISM: Artificial Sequence
<220> FEATURE:
<223> OTHER INFORMATION: synthetic

<400> SEQUENCE: 92

Gln Ser Ile Asn Ser Tyr
1               5

<210> SEQ ID NO 93
<211> LENGTH: 9
<212> TYPE: DNA
<213> ORGANISM: Artificial Sequence
<220> FEATURE:
<223> OTHER INFORMATION: synthetic

<400> SEQUENCE: 93 gttgcatcc                                                          9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Val Ala Ser
1

<210> SEQ ID NO 95
<211> LENGTH: 30
<212> TYPE: DNA
<213> ORGANISM: Artificial Sequence
<220> FEATURE:
<223> OTHER INFORMATION: synthetic

<400> SEQUENCE: 95
caacagagtt acagtacccc tccgatcacc                                  30

<210> SEQ ID NO 96
<211> LENGTH: 10
<212> TYPE: PRT
<213> ORGANISM: Artificial Sequence
<220> FEATURE:
<223> OTHER INFORMATION: synthetic

<400> SEQUENCE: 96

Gln Gln Ser Tyr Ser Thr Pro Pro Ile Thr
1               5                   10

<210> SEQ ID NO 97
<211> LENGTH: 360
<212> TYPE: DNA
<213> ORGANISM: Artificial Sequence
<220> FEATURE:
<223> OTHER INFORMATION: synthetic

<400> SEQUENCE: 97

```
gaggtgcagc tggtggagtc tgggggaggt gtggtacggc cgggggggtc cctgagactc     60
tcctgtgcag cctctggatt cacctttgat gattatggca tgacctgggt ccgccaagtt    120
ccagggaagg ggctggagtg ggtctctggt attcattgga gtggtagaag cacaggttat    180
gcagactctg tgaagggccg attcaccatc tccagagaca acgccaagaa ctccctgtat    240
ctgcaaatga acagtctgag agccgaggac acggccttgt attactgtgc gagggggga    300
atgagtacgg gggactggtt cgaccccctgg ggccagggaa ccctggtcac cgtctcctca   360
```

<210> SEQ ID NO 98
<211> LENGTH: 120
<212> TYPE: PRT
<213> ORGANISM: Artificial Sequence
<220> FEATURE:
<223> OTHER INFORMATION: synthetic

<400> SEQUENCE: 98

Glu Val Gln Leu Val Glu Ser Gly Gly Gly Val Val Arg Pro Gly Gly
1               5                   10                  15
Ser Leu Arg Leu Ser Cys Ala Ala Ser Gly Phe Thr Phe Asp Asp Tyr
            20                  25                  30
Gly Met Thr Trp Val Arg Gln Val Pro Gly Lys Gly Leu Glu Trp Val
        35                  40                  45
Ser Gly Ile His Trp Ser Gly Arg Ser Thr Gly Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Leu Tyr Tyr Cys
                85                  90                  95
Ala Arg Gly Gly Met Ser Thr Gly Asp Trp Phe Asp Pro Trp Gly Gln
            100                 105                 110
Gly Thr Leu Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99

```
ggattcacct ttgatgatta tggc                                            24
```

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Gly Phe Thr Phe Asp Asp Tyr Gly
1               5

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101
attcattgga gtggtagaag caca                                            24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile His Trp Ser Gly Arg Ser Thr
1               5

<210> SEQ ID NO 103
<211> LENGTH: 39
<212> TYPE: DNA
<213> ORGANISM: Artificial Sequence
<220> FEATURE:
<223> OTHER INFORMATION: synthetic

<400> SEQUENCE: 103 gcgaggggggg gaatgagtac gggggactgg ttcgacccc                           39

<210> SEQ ID NO 104
<211> LENGTH: 13
<212> TYPE: PRT
<213> ORGANISM: Artificial Sequence
<220> FEATURE:
<223> OTHER INFORMATION: synthetic

<400> SEQUENCE: 104

Ala Arg Gly Gly Met Ser Thr Gly Asp Trp Phe Asp Pro
1               5                   10

<210> SEQ ID NO 105
<211> LENGTH: 324
<212> TYPE: DNA
<213> ORGANISM: Artificial Sequence
<220> FEATURE:
<223> OTHER INFORMATION: synthetic

<400> SEQUENCE: 105
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgtt gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                           324

<210> SEQ ID NO 106
<211> LENGTH: 108
<212> TYPE: PRT
<213> ORGANISM: Artificial Sequence
<220> FEATURE:
<223> OTHER INFORMATION: synthetic

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107
cagagcatta gcagctat                                                        18

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

Gln Ser Ile Ser Ser Tyr
1               5

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 gttgcatcc                                                                   9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Val Ala Ser
1

<210> SEQ ID NO 111
<211> LENGTH: 30
<212> TYPE: DNA
<213> ORGANISM: Artificial Sequence
<220> FEATURE:
<223> OTHER INFORMATION: synthetic

<400> SEQUENCE: 111
caacagagtt acagtacccc tccgatcacc                             30

<210> SEQ ID NO 112
<211> LENGTH: 10
<212> TYPE: PRT
<213> ORGANISM: Artificial Sequence
<220> FEATURE:
<223> OTHER INFORMATION: synthetic

<400> SEQUENCE: 112

Gln Gln Ser Tyr Ser Thr Pro Pro Ile Thr
1               5                   10

<210> SEQ ID NO 113
<211> LENGTH: 345
<212> TYPE: DNA
<213> ORGANISM: Artificial Sequence
<220> FEATURE:
<223> OTHER INFORMATION: synthetic

<400> SEQUENCE: 113
gaggtgcagt tggtggagtc tggaggaggc ttggtccagc ctgggggtc cctaagactc      60 tcctgtgcag cctctgggtt caccgtcggt agtaactaca tgaactgggt ccgtcaggct    120
ccagggaagg gactggagtg ggtctcagtt atttatagtg gtggtagtac atactacgca    180
gattccgtga agggccgatt caccatctcc agactcactt ccaagaacac actgtatctt    240
caaatgagca gcctgagacc tgaggacacg gccgtgtatt attgtgcgag agggattagg    300
ggtctggacg tctggggcca agggaccacg gtcaccgtct cttca                    345

<210> SEQ ID NO 114
<211> LENGTH: 115
<212> TYPE: PRT
<213> ORGANISM: Artificial Sequence
<220> FEATURE:
<223> OTHER INFORMATION: synthetic

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Gly Ser Asn
            20                  25                  30

Tyr Met Asn Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Leu Thr Ser Lys Asn Thr Leu Tyr Leu
65                  70                  75                  80

Gln Met Ser Ser Leu Arg Pro Glu Asp Thr Ala Val Tyr Tyr Cys Ala
                85                  90                  95

Arg Gly Ile Arg Gly Leu Asp Val Trp Gly Gln Gly Thr Thr Val Thr

Val Ser Ser
        115

<210> SEQ ID NO 115
<211> LENGTH: 24
<212> TYPE: DNA
<213> ORGANISM: Artificial Sequence
<220> FEATURE:
<223> OTHER INFORMATION: synthetic

<400> SEQUENCE: 115
gggttcaccg tcggtagtaa ctac                                          24

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

Gly Phe Thr Val Gly Ser Asn Tyr
1               5

<210> SEQ ID NO 117
<211> LENGTH: 21
<212> TYPE: DNA
<213> ORGANISM: Artificial Sequence
<220> FEATURE:
<223> OTHER INFORMATION: synthetic

<400> SEQUENCE: 117
atttatagtg gtggtagtac a                                             21

<210> SEQ ID NO 118
<211> LENGTH: 7
<212> TYPE: PRT
<213> ORGANISM: Artificial Sequence
<220> FEATURE:
<223> OTHER INFORMATION: synthetic

<400> SEQUENCE: 118

Ile Tyr Ser Gly Gly Ser Thr
1               5

<210> SEQ ID NO 119
<211> LENGTH: 27
<212> TYPE: DNA
<213> ORGANISM: Artificial Sequence
<220> FEATURE:
<223> OTHER INFORMATION: synthetic

<400> SEQUENCE: 119
gcgagaggga ttagggtct ggacgtc                                        27

<210> SEQ ID NO 120
<211> LENGTH: 9
<212> TYPE: PRT
<213> ORGANISM: Artificial Sequence
<220> FEATURE:
<223> OTHER INFORMATION: synthetic

<400> SEQUENCE: 120

Ala Arg Gly Ile Arg Gly Leu Asp Val
1               5

<210> SEQ ID NO 121
<211> LENGTH: 324
<212> TYPE: DNA
<213> ORGANISM: Artificial Sequence
<220> FEATURE:
<223> OTHER INFORMATION: synthetic

<400> SEQUENCE: 121

```
gacatccaga tgacccagtc tccatcctcc ctgtctgcat ctgtaggaga cagagtcacc      60
atcacttgcc gggcaagtca gaccattaac atctatttaa attggtatca gcagaaacca     120
gggagagccc ctaggctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaccag agttacagta cccctccgat caccttcggc     300
caagggacac gactggagat taaa                                            324
```

<210> SEQ ID NO 122
<211> LENGTH: 108
<212> TYPE: PRT
<213> ORGANISM: Artificial Sequence
<220> FEATURE:
<223> OTHER INFORMATION: synthetic

<400> SEQUENCE: 122

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Thr Ile Asn Ile Tyr
            20                  25                  30
Leu Asn Trp Tyr Gln Gln Lys Pro Gly Arg Ala Pro Arg Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys His Gln Ser Tyr Ser Thr Pro Pro
                85                  90                  95
Ile Thr Phe Gly Gln Gly Thr Arg Leu Glu Ile Lys
            100                 105
```

<210> SEQ ID NO 123
<211> LENGTH: 18
<212> TYPE: DNA
<213> ORGANISM: Artificial Sequence
<220> FEATURE:
<223> OTHER INFORMATION: synthetic

<400> SEQUENCE: 123

```
cagaccatta acatctat                                                    18
```

<210> SEQ ID NO 124
<211> LENGTH: 6
<212> TYPE: PRT
<213> ORGANISM: Artificial Sequence
<220> FEATURE:
<223> OTHER INFORMATION: synthetic

<400> SEQUENCE: 124

```
Gln Thr Ile Asn Ile Tyr
1               5
```

```
<210> SEQ ID NO 125
<211> LENGTH: 9
<212> TYPE: DNA
<213> ORGANISM: Artificial Sequence
<220> FEATURE:
<223> OTHER INFORMATION: synthetic

<400> SEQUENCE: 125 gctgcatcc                                                              9

<210> SEQ ID NO 126
<211> LENGTH: 3
<212> TYPE: PRT
<213> ORGANISM: Artificial Sequence
<220> FEATURE:
<223> OTHER INFORMATION: synthetic

<400> SEQUENCE: 126

Ala Ala Ser
1

<210> SEQ ID NO 127
<211> LENGTH: 30
<212> TYPE: DNA
<213> ORGANISM: Artificial Sequence
<220> FEATURE:
<223> OTHER INFORMATION: synthetic

<400> SEQUENCE: 127
caccagagtt acagtacccc tccgatcacc                                      30

<210> SEQ ID NO 128
<211> LENGTH: 10
<212> TYPE: PRT
<213> ORGANISM: Artificial Sequence
<220> FEATURE:
<223> OTHER INFORMATION: synthetic

<400> SEQUENCE: 128

His Gln Ser Tyr Ser Thr Pro Pro Ile Thr
1               5                   10

<210> SEQ ID NO 129
<211> LENGTH: 345
<212> TYPE: DNA
<213> ORGANISM: Artificial Sequence
<220> FEATURE:
<223> OTHER INFORMATION: synthetic

<400> SEQUENCE: 129
gaggaacggt tggtggagtc tggaggagac ttggtccagc ctggggggtc cctgagactc     60
tcctgtgcag cctctggcat caccgtcggt actaattata tgaactgggt ccgccaggct    120
ccagggaagg gactggagtg ggtctcagtt atttctagcg gtggtaatac acactacgca    180
gactccgtga agggccgatt cattatgtcc agacaaactt ccaaaaacac gctgtatctt    240
cagatgaata gcctggaaac tgaggacacg gccgtatatt attgtgcgag ggggatcaga    300
ggtttggacg tctggggcca agggaccatg gtcaccgtct cctca                    345

<210> SEQ ID NO 130
<211> LENGTH: 115
<212> TYPE: PRT
<213> ORGANISM: Artificial Sequence
<220> FEATURE:
<223> OTHER INFORMATION: synthetic
```

<400> SEQUENCE: 130

Glu Glu Arg Leu Val Glu Ser Gly Gly Asp Leu Val Gln Pro Gly Gly
1               5                   10                  15

Ser Leu Arg Leu Ser Cys Ala Ala Ser Gly Ile Thr Val Gly Thr Asn
            20                  25                  30

Tyr Met Asn Trp Val Arg Gln Ala Pro Gly Lys Gly Leu Glu Trp Val
        35                  40                  45

Ser Val Ile Ser Ser Gly Gly Asn Thr His Tyr Ala Asp Ser Val Lys
    50                  55                  60

Gly Arg Phe Ile Met Ser Arg Gln Thr Ser Lys Asn Thr Leu Tyr Leu
65                  70                  75                  80

Gln Met Asn Ser Leu Glu Thr Glu Asp Thr Ala Val Tyr Tyr Cys Ala
                85                  90                  95

Arg Gly Ile Arg Gly Leu Asp Val Trp Gly Gln Gly Thr Met Val Thr
            100                 105                 110

Val Ser Ser
    115

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131
ggcatcaccg tcggtactaa ttat                                          24

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

Gly Ile Thr Val Gly Thr Asn Tyr
1               5

<210> SEQ ID NO 133
<211> LENGTH: 21
<212> TYPE: DNA
<213> ORGANISM: Artificial Sequence
<220> FEATURE:
<223> OTHER INFORMATION: synthetic

<400> SEQUENCE: 133
atttctagcg gtggtaatac a                                             21

<210> SEQ ID NO 134
<211> LENGTH: 7
<212> TYPE: PRT
<213> ORGANISM: Artificial Sequence
<220> FEATURE:
<223> OTHER INFORMATION: synthetic

<400> SEQUENCE: 134

Ile Ser Ser Gly Gly Asn Thr
1               5

<210> SEQ ID NO 135

```
<211> LENGTH: 27
<212> TYPE: DNA
<213> ORGANISM: Artificial Sequence
<220> FEATURE:
<223> OTHER INFORMATION: synthetic

<400> SEQUENCE: 135
gcgaggggga tcagaggttt ggacgtc                                          27

<210> SEQ ID NO 136
<211> LENGTH: 9
<212> TYPE: PRT
<213> ORGANISM: Artificial Sequence
<220> FEATURE:
<223> OTHER INFORMATION: synthetic

<400> SEQUENCE: 136

Ala Arg Gly Ile Arg Gly Leu Asp Val
1               5

<210> SEQ ID NO 137
<211> LENGTH: 324
<212> TYPE: DNA
<213> ORGANISM: Artificial Sequence
<220> FEATURE:
<223> OTHER INFORMATION: synthetic

<400> SEQUENCE: 137
gacatccaga tgacccagtc tccatcctcc ctgtctgcat ctgtaggaga cagagtcacc      60
atcacttgcc gggcaagtca gagcatgagc agctatttaa attggtatca gcagaaacca    120
gggagagccc ctaagctcct gatctttgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                           324

<210> SEQ ID NO 138
<211> LENGTH: 108
<212> TYPE: PRT
<213> ORGANISM: Artificial Sequence
<220> FEATURE:
<223> OTHER INFORMATION: synthetic

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Met Ser Ser Tyr
            20                  25                  30

Leu Asn Trp Tyr Gln Gln Lys Pro Gly Arg Ala Pro Lys Leu Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 139
<211> LENGTH: 18
```

```
<212> TYPE: DNA
<213> ORGANISM: Artificial Sequence
<220> FEATURE:
<223> OTHER INFORMATION: synthetic

<400> SEQUENCE: 139
cagagcatga gcagctat                                                   18

<210> SEQ ID NO 140
<211> LENGTH: 6
<212> TYPE: PRT
<213> ORGANISM: Artificial Sequence
<220> FEATURE:
<223> OTHER INFORMATION: synthetic

<400> SEQUENCE: 140

Gln Ser Met Ser Ser Tyr
1               5

<210> SEQ ID NO 141
<211> LENGTH: 9
<212> TYPE: DNA
<213> ORGANISM: Artificial Sequence
<220> FEATURE:
<223> OTHER INFORMATION: synthetic

<400> SEQUENCE: 141 gctgcatcc                                                              9

<210> SEQ ID NO 142
<211> LENGTH: 3
<212> TYPE: PRT
<213> ORGANISM: Artificial Sequence
<220> FEATURE:
<223> OTHER INFORMATION: synthetic

<400> SEQUENCE: 142

Ala Ala Ser
1

<210> SEQ ID NO 143
<211> LENGTH: 30
<212> TYPE: DNA
<213> ORGANISM: Artificial Sequence
<220> FEATURE:
<223> OTHER INFORMATION: synthetic

<400> SEQUENCE: 143
caacagagtt acagtacccc tccgatcacc                                      30

<210> SEQ ID NO 144
<211> LENGTH: 10
<212> TYPE: PRT
<213> ORGANISM: Artificial Sequence
<220> FEATURE:
<223> OTHER INFORMATION: synthetic

<400> SEQUENCE: 144

Gln Gln Ser Tyr Ser Thr Pro Pro Ile Thr
1               5                   10

<210> SEQ ID NO 145
<211> LENGTH: 354
<212> TYPE: DNA
<213> ORGANISM: Artificial Sequence
<220> FEATURE:
<223> OTHER INFORMATION: synthetic
```

<400> SEQUENCE: 145

```
caggtccagc tggtgcagtc tggggctgag gtgaagatgc ctgggtcctc ggtgagggtc      60
tcctgcaagg cttctggagg catcttcagc agttctacta tcagttgggt gcgacaggcc     120
cctggacaag ggcttgaatg gatgggagag atcatccctg tctttggtac agtaaactac     180
gcacagaagt tccaggacag agtcatattt accgcggacg aatctacgac tacagcctac     240
atggagctga gcagcctgaa atctggggac acggccgtat attctgtgc gcgaaattgg      300
ggattaggct ctttttatat ctggggccaa gggacaatgg tcaccgtctc ttca           354
```

<210> SEQ ID NO 146
<211> LENGTH: 118
<212> TYPE: PRT
<213> ORGANISM: Artificial Sequence
<220> FEATURE:
<223> OTHER INFORMATION: synthetic

<400> SEQUENCE: 146

Gln Val Gln Leu Val Gln Ser Gly Ala Glu Val Lys Met Pro Gly Ser
1               5                   10                  15

Ser Val Arg Val Ser Cys Lys Ala Ser Gly Gly Ile Phe Ser Ser Ser
            20                  25                  30

Thr Ile Ser Trp Val Arg Gln Ala Pro Gly Gln Gly Leu Glu Trp Met
        35                  40                  45

Gly Glu Ile Ile Pro Val Phe Gly Thr Val Asn Tyr Ala Gln Lys Phe
    50                  55                  60

Gln Asp Arg Val Ile Phe Thr Ala Asp Glu Ser Thr Thr Thr Ala Tyr
65                  70                  75                  80

Met Glu Leu Ser Ser Leu Lys Ser Gly Asp Thr Ala Val Tyr Phe Cys
                85                  90                  95

Ala Arg Asn Trp Gly Leu Gly Ser Phe Tyr Ile Trp Gly Gln Gly Thr
            100                 105                 110

Met Val Thr Val Ser Ser
        115

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147

```
ggaggcatct tcagcagttc tact                                             24
```

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

Gly Gly Ile Phe Ser Ser Ser Thr
1               5

<210> SEQ ID NO 149
<211> LENGTH: 24
<212> TYPE: DNA
<213> ORGANISM: Artificial Sequence
<220> FEATURE:
<223> OTHER INFORMATION: synthetic

<400> SEQUENCE: 149
atcatccctg tctttggtac agta                                          24

<210> SEQ ID NO 150
<211> LENGTH: 8
<212> TYPE: PRT
<213> ORGANISM: Artificial Sequence
<220> FEATURE:
<223> OTHER INFORMATION: synthetic

<400> SEQUENCE: 150

Ile Ile Pro Val Phe Gly Thr Val
1               5

<210> SEQ ID NO 151
<211> LENGTH: 33
<212> TYPE: DNA
<213> ORGANISM: Artificial Sequence
<220> FEATURE:
<223> OTHER INFORMATION: synthetic

<400> SEQUENCE: 151
gcgcgaaatt ggggattagg ctcttttat atc                                 33

<210> SEQ ID NO 152
<211> LENGTH: 11
<212> TYPE: PRT
<213> ORGANISM: Artificial Sequence
<220> FEATURE:
<223> OTHER INFORMATION: synthetic

<400> SEQUENCE: 152

Ala Arg Asn Trp Gly Leu Gly Ser Phe Tyr Ile
1               5                   10

<210> SEQ ID NO 153
<211> LENGTH: 324
<212> TYPE: DNA
<213> ORGANISM: Artificial Sequence
<220> FEATURE:
<223> OTHER INFORMATION: synthetic

<400> SEQUENCE: 153
gaaattgtgt tgacgcagtc tccaggcacc ctgtctttgt ctccagggga aagagccacc    60
ctctcctgca gggccagtca gagttttaac ttcaactact tagcctggta ccagcagaaa   120
cctggccagg ctcccagact cctcatctat ggtgcatcca gcagggccac tggcatccca   180
gacaggttca gtggcagtgg gtctgggaca gacttcactc tcaccatcaa caggctggag   240
cctgaagatt ttggagtgtt ttattgtcag cagtatgaaa gcgcaccttg gacgttcggc   300
caagggacca aggtggaaat caaa                                         324

<210> SEQ ID NO 154
<211> LENGTH: 108
<212> TYPE: PRT
<213> ORGANISM: Artificial Sequence
<220> FEATURE:
<223> OTHER INFORMATION: synthetic

<400> SEQUENCE: 154

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Asn Phe Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Asn Arg Leu Glu
65                  70                  75                  80

Pro Glu Asp Phe Gly Val Phe Tyr Cys Gln Gln Tyr Glu Ser Ala Pro
                85                  90                  95

Trp Thr Phe Gly Gln Gly Thr Lys Val Glu Ile Lys
            100                 105

<210> SEQ ID NO 155
<211> LENGTH: 21
<212> TYPE: DNA
<213> ORGANISM: Artificial Sequence
<220> FEATURE:
<223> OTHER INFORMATION: synthetic

<400> SEQUENCE: 155 cagagttta acttcaacta c                                          21

<210> SEQ ID NO 156
<211> LENGTH: 7
<212> TYPE: PRT
<213> ORGANISM: Artificial Sequence
<220> FEATURE:
<223> OTHER INFORMATION: synthetic

<400> SEQUENCE: 156

Gln Ser Phe Asn Phe Asn Tyr
1               5

<210> SEQ ID NO 157
<211> LENGTH: 9
<212> TYPE: DNA
<213> ORGANISM: Artificial Sequence
<220> FEATURE:
<223> OTHER INFORMATION: synthetic

<400> SEQUENCE: 157 ggtgcatcc                                                       9

<210> SEQ ID NO 158
<211> LENGTH: 3
<212> TYPE: PRT
<213> ORGANISM: Artificial Sequence
<220> FEATURE:
<223> OTHER INFORMATION: synthetic

<400> SEQUENCE: 158

Gly Ala Ser
1

<210> SEQ ID NO 159
<211> LENGTH: 27
<212> TYPE: DNA
<213> ORGANISM: Artificial Sequence
<220> FEATURE:
<223> OTHER INFORMATION: synthetic

<400> SEQUENCE: 159

```
cagcagtatg aaagcgcacc ttggacg                                              27
```

<210> SEQ ID NO 160
<211> LENGTH: 9
<212> TYPE: PRT
<213> ORGANISM: Artificial Sequence
<220> FEATURE:
<223> OTHER INFORMATION: synthetic

<400> SEQUENCE: 160

Gln Gln Tyr Glu Ser Ala Pro Trp Thr
1               5

<210> SEQ ID NO 161
<211> LENGTH: 345
<212> TYPE: DNA
<213> ORGANISM: Artificial Sequence
<220> FEATURE:
<223> OTHER INFORMATION: synthetic

<400> SEQUENCE: 161

```
gaggtgcagc ttgtagagtc tgggggagac ttggtacatc ctggcaggtc cctgagactc      60
tcctgtgcag cctctggttt cccctttgat gagtatgcca tgcactgggt ccggcaagtt     120
ccagggaagg gcctggagtg ggtctcaggt attagttgga gtaataataa cataggctat     180
gcggactctg tgaagggccg attcaccatc tccagagaca cgccaaaaa ctccctgtat      240 ctacaaatga acagtctgag acctgaggac acggcctttt attactgtgc aaaatctgga     300
atctttgact cctggggcca gggaaccctg gtcaccgtct cctca                     345
```

<210> SEQ ID NO 162
<211> LENGTH: 115
<212> TYPE: PRT
<213> ORGANISM: Artificial Sequence
<220> FEATURE:
<223> OTHER INFORMATION: synthetic

<400> SEQUENCE: 162

Glu Val Gln Leu Val Glu Ser Gly Gly Asp Leu Val His Pro Gly Arg
1               5                   10                  15

Ser Leu Arg Leu Ser Cys Ala Ala Ser Gly Phe Pro Phe Asp Glu Tyr
            20                  25                  30

Ala Met His Trp Val Arg Gln Val Pro Gly Lys Gly Leu Glu Trp Val
        35                  40                  45

Ser Gly Ile Ser Trp Ser Asn Asn Asn Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Phe Tyr Tyr Cys
                85                  90                  95

Ala Lys Ser Gly Ile Phe Asp Ser Trp Gly Gln Gly Thr Leu Val Thr
            100                 105                 110

Val Ser Ser
        115

<210> SEQ ID NO 163
<211> LENGTH: 24
<212> TYPE: DNA
<213> ORGANISM: Artificial Sequence
<220> FEATURE:
<223> OTHER INFORMATION: synthetic

```
<400> SEQUENCE: 163 ggtttccect ttgatgagta tgcc                                              24

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

Gly Phe Pro Phe Asp Glu Tyr Ala
1               5

<210> SEQ ID NO 165
<211> LENGTH: 24
<212> TYPE: DNA
<213> ORGANISM: Artificial Sequence
<220> FEATURE:
<223> OTHER INFORMATION: synthetic

<400> SEQUENCE: 165
attagttgga gtaataataa cata                                              24

<210> SEQ ID NO 166
<211> LENGTH: 8
<212> TYPE: PRT
<213> ORGANISM: Artificial Sequence
<220> FEATURE:
<223> OTHER INFORMATION: synthetic

<400> SEQUENCE: 166

Ile Ser Trp Ser Asn Asn Asn Ile
1               5

<210> SEQ ID NO 167
<211> LENGTH: 24
<212> TYPE: DNA
<213> ORGANISM: Artificial Sequence
<220> FEATURE:
<223> OTHER INFORMATION: synthetic

<400> SEQUENCE: 167
gcaaaatctg gaatctttga ctcc                                              24

<210> SEQ ID NO 168
<211> LENGTH: 8
<212> TYPE: PRT
<213> ORGANISM: Artificial Sequence
<220> FEATURE:
<223> OTHER INFORMATION: synthetic

<400> SEQUENCE: 168

Ala Lys Ser Gly Ile Phe Asp Ser
1               5

<210> SEQ ID NO 169
<211> LENGTH: 315
<212> TYPE: DNA
<213> ORGANISM: Artificial Sequence
<220> FEATURE:
<223> OTHER INFORMATION: synthetic

<400> SEQUENCE: 169
gacatccaga tgacccagtc tccatcctcc ctgtctgcat ctgtaggaga cagagtcacc       60
```
atcacttgcc gggcaagtca gagcattagc agctatttaa attggtatca gcagaaacca 120
gggaagctcc tgatctatgc tgcatccagt ttgcaaagtg gggtcccatc acggttcagt 180
ggcggtggat ctgggacaga tttcactctc accatcagca gtctgcgacc tgaagatttt 240
gcaacttact actgtcaaca gagttactgt accccctccga tcaccttcgg ccaagggaca 300
cgactggaga ttaaa 315

<210> SEQ ID NO 170
<211> LENGTH: 105
<212> TYPE: PRT
<213> ORGANISM: Artificial Sequence
<220> FEATURE:
<223> OTHER INFORMATION: synthetic

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Leu Leu Ile Tyr Ala Ala
        35                  40                  45

Ser Ser Leu Gln Ser Gly Val Pro Ser Arg Phe Ser Gly Gly Gly Ser
    50                  55                  60

Gly Thr Asp Phe Thr Leu Thr Ile Ser Ser Leu Arg Pro Glu Asp Phe
65                  70                  75                  80

Ala Thr Tyr Tyr Cys Gln Gln Ser Tyr Cys Thr Pro Pro Ile Thr Phe
                85                  90                  95

Gly Gln Gly Thr Arg Leu Glu Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: synthetic

<400> SEQUENCE: 171
cagagcatta gcagctat 18

<210> SEQ ID NO 172
<211> LENGTH: 6
<212> TYPE: PRT
<213> ORGANISM: Artificial Sequence
<220> FEATURE:
<223> OTHER INFORMATION: synthetic

<400> SEQUENCE: 172

Gln Ser Ile Ser Ser Tyr
1               5

<210> SEQ ID NO 173
<211> LENGTH: 9
<212> TYPE: DNA
<213> ORGANISM: Artificial Sequence
<220> FEATURE:
<223> OTHER INFORMATION: synthetic

<400> SEQUENCE: 173 gctgcatcc 9

<210> SEQ ID NO 174
<211> LENGTH: 3
<212> TYPE: PRT
<213> ORGANISM: Artificial Sequence
<220> FEATURE:
<223> OTHER INFORMATION: synthetic

<400> SEQUENCE: 174

Ala Ala Ser
1

<210> SEQ ID NO 175
<211> LENGTH: 30
<212> TYPE: DNA
<213> ORGANISM: Artificial Sequence
<220> FEATURE:
<223> OTHER INFORMATION: synthetic

<400> SEQUENCE: 175
caacagagtt actgtacccc tccgatcacc                                      30

<210> SEQ ID NO 176
<211> LENGTH: 10
<212> TYPE: PRT
<213> ORGANISM: Artificial Sequence
<220> FEATURE:
<223> OTHER INFORMATION: synthetic

<400> SEQUENCE: 176

Gln Gln Ser Tyr Cys Thr Pro Pro Ile Thr
1               5                   10

<210> SEQ ID NO 177
<211> LENGTH: 354
<212> TYPE: DNA
<213> ORGANISM: Artificial Sequence
<220> FEATURE:
<223> OTHER INFORMATION: synthetic

<400> SEQUENCE: 177
gaggtgcagc tggtggagtc cggggggaggc gtggtccagc ctggggaggtc cctgagactc     60 tcctgtgcag cctctggatt caccttcagt agttatggca tgcactgggt ccgccaggct    120
ccaggcaagg gactggagtg ggtgacactt atatcatatg agggaaggaa taaatactat    180
gcagactccg tgaagggccg attcaccatt tccagagaca attccaagaa cacgctgtat    240
ctgcaaatga acagcctgag agctgaggac acggctgtat attactgtgc gaaagatagg    300
accctttacg gtatggacgt ctggggccaa ggaaccacgg tcaccgtctc ctca          354

<210> SEQ ID NO 178
<211> LENGTH: 118
<212> TYPE: PRT
<213> ORGANISM: Artificial Sequence
<220> FEATURE:
<223> OTHER INFORMATION: synthetic

<400> SEQUENCE: 178

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Thr Leu Ile Ser Tyr Glu Gly Arg Asn Lys Tyr Tyr Ala Asp Ser Val

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Thr Leu Tyr Gly Met Asp Val Trp Gly Gln Gly Thr
            100                 105                 110

Thr Val Thr Val Ser Ser
            115

<210> SEQ ID NO 179
<211> LENGTH: 24
<212> TYPE: DNA
<213> ORGANISM: Artificial Sequence
<220> FEATURE:
<223> OTHER INFORMATION: synthetic

<400> SEQUENCE: 179
ggattcacct tcagtagtta tggc                                            24

<210> SEQ ID NO 180
<211> LENGTH: 8
<212> TYPE: PRT
<213> ORGANISM: Artificial Sequence
<220> FEATURE:
<223> OTHER INFORMATION: synthetic

<400> SEQUENCE: 180

Gly Phe Thr Phe Ser Ser Tyr Gly
 1               5

<210> SEQ ID NO 181
<211> LENGTH: 24
<212> TYPE: DNA
<213> ORGANISM: Artificial Sequence
<220> FEATURE:
<223> OTHER INFORMATION: synthetic

<400> SEQUENCE: 181
atatcatatg agggaaggaa taaa                                            24

<210> SEQ ID NO 182
<211> LENGTH: 8
<212> TYPE: PRT
<213> ORGANISM: Artificial Sequence
<220> FEATURE:
<223> OTHER INFORMATION: synthetic

<400> SEQUENCE: 182

Ile Ser Tyr Glu Gly Arg Asn Lys
 1               5

<210> SEQ ID NO 183
<211> LENGTH: 33
<212> TYPE: DNA
<213> ORGANISM: Artificial Sequence
<220> FEATURE:
<223> OTHER INFORMATION: synthetic

<400> SEQUENCE: 183
gcgaaagata ggacccttta cggtatggac gtc                                  33

<210> SEQ ID NO 184
<211> LENGTH: 11
```

```
<212> TYPE: PRT
<213> ORGANISM: Artificial Sequence
<220> FEATURE:
<223> OTHER INFORMATION: synthetic

<400> SEQUENCE: 184

Ala Lys Asp Arg Thr Leu Tyr Gly Met Asp Val
1               5                   10

<210> SEQ ID NO 185
<211> LENGTH: 363
<212> TYPE: DNA
<213> ORGANISM: Artificial Sequence
<220> FEATURE:
<223> OTHER INFORMATION: synthetic

<400> SEQUENCE: 185
caggtcacct tgagggagtc tggtcctgcg ctggtgaaaa ccacacagac cctcacactg      60
acctgcacct tctctgggtt ctcactcagc actaatagaa tgtgtgtgac ctggatccgt     120
cagcccccag ggaaggccct ggagtggctt gcgcgcattg attgggatgg tgttaaatac     180
tacaacacat ctctgaagac caggctcacc atctccaagg acacctccaa aaaccaggtg     240
gtccttacaa tgaccaacat ggaccctgtg gacacagcca cttttttactg tgcacggtcg     300 acttcgttga cttttttacta ctttgactac tggggccagg gaaccctggt caccgtctcc     360
tca                                                                    363

<210> SEQ ID NO 186
<211> LENGTH: 121
<212> TYPE: PRT
<213> ORGANISM: Artificial Sequence
<220> FEATURE:
<223> OTHER INFORMATION: synthetic

<400> SEQUENCE: 186

Gln Val Thr Leu Arg Glu Ser Gly Pro Ala Leu Val Lys Thr Thr Gln
1               5                   10                  15

Thr Leu Thr Leu Thr Cys Thr Phe Ser Gly Phe Ser Leu Ser Thr Asn
            20                  25                  30

Arg Met Cys Val Thr Trp Ile Arg Gln Pro Pro Gly Lys Ala Leu Glu
        35                  40                  45

Trp Leu Ala Arg Ile Asp Trp Asp Gly Val Lys Tyr Tyr Asn Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Phe Tyr
                85                  90                  95

Cys Ala Arg Ser Thr Ser Leu Thr Phe Tyr Tyr Phe Asp Tyr Trp Gly
            100                 105                 110

Gln Gly Thr Leu Val Thr Val Ser Ser
        115                 120

<210> SEQ ID NO 187
<211> LENGTH: 30
<212> TYPE: DNA
<213> ORGANISM: Artificial Sequence
<220> FEATURE:
<223> OTHER INFORMATION: synthetic

<400> SEQUENCE: 187
gggttctcac tcagcactaa tagaatgtgt                                        30
```

<210> SEQ ID NO 188
<211> LENGTH: 10
<212> TYPE: PRT
<213> ORGANISM: Artificial Sequence
<220> FEATURE:
<223> OTHER INFORMATION: synthetic

<400> SEQUENCE: 188

Gly Phe Ser Leu Ser Thr Asn Arg Met Cys
1               5                   10

<210> SEQ ID NO 189
<211> LENGTH: 21
<212> TYPE: DNA
<213> ORGANISM: Artificial Sequence
<220> FEATURE:
<223> OTHER INFORMATION: synthetic

<400> SEQUENCE: 189
attgattggg atggtgttaa a                                        21

<210> SEQ ID NO 190
<211> LENGTH: 7
<212> TYPE: PRT
<213> ORGANISM: Artificial Sequence
<220> FEATURE:
<223> OTHER INFORMATION: synthetic

<400> SEQUENCE: 190

Ile Asp Trp Asp Gly Val Lys
1               5

<210> SEQ ID NO 191
<211> LENGTH: 39
<212> TYPE: DNA
<213> ORGANISM: Artificial Sequence
<220> FEATURE:
<223> OTHER INFORMATION: synthetic

<400> SEQUENCE: 191
gcacggtcga cttcgttgac tttttactac tttgactac                     39

<210> SEQ ID NO 192
<211> LENGTH: 13
<212> TYPE: PRT
<213> ORGANISM: Artificial Sequence
<220> FEATURE:
<223> OTHER INFORMATION: synthetic

<400> SEQUENCE: 192

Ala Arg Ser Thr Ser Leu Thr Phe Tyr Tyr Phe Asp Tyr
1               5                   10

<210> SEQ ID NO 193
<211> LENGTH: 324
<212> TYPE: DNA
<213> ORGANISM: Artificial Sequence
<220> FEATURE:
<223> OTHER INFORMATION: synthetic

<400> SEQUENCE: 193
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct      240
gaagattttg caacttacta ctgtcaacag agttacagta cccctccgat caccttcggc      300
caagggacac gactggagat taaa                                             324

<210> SEQ ID NO 194
<211> LENGTH: 108
<212> TYPE: PRT
<213> ORGANISM: Artificial Sequence
<220> FEATURE:
<223> OTHER INFORMATION: synthetic

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 195
<211> LENGTH: 18
<212> TYPE: DNA
<213> ORGANISM: Artificial Sequence
<220> FEATURE:
<223> OTHER INFORMATION: synthetic

<400> SEQUENCE: 195
cagagcatta gcagctat                                                    18

<210> SEQ ID NO 196
<211> LENGTH: 6
<212> TYPE: PRT
<213> ORGANISM: Artificial Sequence
<220> FEATURE:
<223> OTHER INFORMATION: synthetic

<400> SEQUENCE: 196

Gln Ser Ile Ser Ser Tyr
1               5

<210> SEQ ID NO 197
<211> LENGTH: 9
<212> TYPE: DNA
<213> ORGANISM: Artificial Sequence
<220> FEATURE:
<223> OTHER INFORMATION: synthetic

<400> SEQUENCE: 197 gctgcatcc                                                              9

<210> SEQ ID NO 198
<211> LENGTH: 3
<212> TYPE: PRT

<213> ORGANISM: Artificial Sequence
<220> FEATURE:
<223> OTHER INFORMATION: synthetic

<400> SEQUENCE: 198

Ala Ala Ser
1

<210> SEQ ID NO 199
<211> LENGTH: 30
<212> TYPE: DNA
<213> ORGANISM: Artificial Sequence
<220> FEATURE:
<223> OTHER INFORMATION: synthetic

<400> SEQUENCE: 199
caacagagtt acagtacccc tccgatcacc                                    30

<210> SEQ ID NO 200
<211> LENGTH: 10
<212> TYPE: PRT
<213> ORGANISM: Artificial Sequence
<220> FEATURE:
<223> OTHER INFORMATION: synthetic

<400> SEQUENCE: 200

Gln Gln Ser Tyr Ser Thr Pro Pro Ile Thr
1               5                   10

<210> SEQ ID NO 201
<211> LENGTH: 345
<212> TYPE: DNA
<213> ORGANISM: Artificial Sequence
<220> FEATURE:
<223> OTHER INFORMATION: synthetic

<400> SEQUENCE: 201
gaggtgcagc tggtggagtc tgaggaggc ttggtccagc cggggggtc cctgagactc     60
tcctgtgcag cctctgagtt caccgtcggt accaaccaca tgaactgggt ccgccaggct  120
ccagggaagg gactggagtg gtctcagtt atttatagcg gtggtaacac attctacgca  180
gactccgtga agggccgatt caccatctcc agacacactt ccaagaacac gctgtatctt  240
caaatgaaca gcctgacagc agaggacacg gccgtatatt actgtgcgcg aggattgggg  300
ggtatggacg tctggggcca agggaccacg gtcaccgtct cctca                  345

<210> SEQ ID NO 202
<211> LENGTH: 115
<212> TYPE: PRT
<213> ORGANISM: Artificial Sequence
<220> FEATURE:
<223> OTHER INFORMATION: synthetic

<400> SEQUENCE: 202

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Val Gly Thr Asn
            20                  25                  30

His Met Asn Trp Val Arg Gln Ala Pro Gly Lys Gly Leu Glu Trp Val
        35                  40                  45

Ser Val Ile Tyr Ser Gly Gly Asn Thr Phe Tyr Ala Asp Ser Val Lys
    50                  55                  60

Gly Arg Phe Thr Ile Ser Arg His Thr Ser Lys Asn Thr Leu Tyr Leu

```
                65                  70                  75                  80
Gln Met Asn Ser Leu Thr Ala Glu Asp Thr Ala Val Tyr Tyr Cys Ala
                    85                  90                  95

Arg Gly Leu Gly Gly Met Asp Val Trp Gly Gln Gly Thr Thr Val Thr
                100                 105                 110

Val Ser Ser
        115
```

<210> SEQ ID NO 203
<211> LENGTH: 24
<212> TYPE: DNA
<213> ORGANISM: Artificial Sequence
<220> FEATURE:
<223> OTHER INFORMATION: synthetic

<400> SEQUENCE: 203
gagttcaccg tcggtaccaa ccac          24

<210> SEQ ID NO 204
<211> LENGTH: 8
<212> TYPE: PRT
<213> ORGANISM: Artificial Sequence
<220> FEATURE:
<223> OTHER INFORMATION: synthetic

<400> SEQUENCE: 204

```
Glu Phe Thr Val Gly Thr Asn His
1               5
```

<210> SEQ ID NO 205
<211> LENGTH: 21
<212> TYPE: DNA
<213> ORGANISM: Artificial Sequence
<220> FEATURE:
<223> OTHER INFORMATION: synthetic

<400> SEQUENCE: 205
atttatagcg gtggtaacac a          21

<210> SEQ ID NO 206
<211> LENGTH: 7
<212> TYPE: PRT
<213> ORGANISM: Artificial Sequence
<220> FEATURE:
<223> OTHER INFORMATION: synthetic

<400> SEQUENCE: 206

```
Ile Tyr Ser Gly Gly Asn Thr
1               5
```

<210> SEQ ID NO 207
<211> LENGTH: 27
<212> TYPE: DNA
<213> ORGANISM: Artificial Sequence
<220> FEATURE:
<223> OTHER INFORMATION: synthetic

<400> SEQUENCE: 207
gcgcgaggat tgggggtat ggacgtc          27

<210> SEQ ID NO 208
<211> LENGTH: 9
<212> TYPE: PRT
<213> ORGANISM: Artificial Sequence
<220> FEATURE:

<223> OTHER INFORMATION: synthetic

<400> SEQUENCE: 208

Ala Arg Gly Leu Gly Gly Met Asp Val
1               5

<210> SEQ ID NO 209
<211> LENGTH: 321
<212> TYPE: DNA
<213> ORGANISM: Artificial Sequence
<220> FEATURE:
<223> OTHER INFORMATION: synthetic

<400> SEQUENCE: 209
gacatccaga tgacccagtc tccatcctcc ctgtctgcat ctgtaggaga cagagtcacc      60
atcacttgcc gggcgagtca ggtcattagc aattatttag cctggtatca gcagaaacca     120
gggaaagttc ctaggctcct gatctatgct gcatccactt tgcaatcagg ggtcccatct     180
cgtttcagtg gcagtggatc tgggacagat ttcactctca ccatcagcag cctgcagcct     240
gaagatgttg caacttatta ctgtcaaaag tataacagtg cccctcggac gttcggccaa     300
gggaccaagg tggaaatcaa a                                                321

<210> SEQ ID NO 210
<211> LENGTH: 107
<212> TYPE: PRT
<213> ORGANISM: Artificial Sequence
<220> FEATURE:
<223> OTHER INFORMATION: synthetic

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Ser Asn Tyr
            20                  25                  30

Leu Ala Trp Tyr Gln Gln Lys Pro Gly Lys Val Pro Arg Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Arg
                85                  90                  95

Thr Phe Gly Gln Gly Thr Lys Val Glu Ile Lys
            100                 105

<210> SEQ ID NO 211
<211> LENGTH: 18
<212> TYPE: DNA
<213> ORGANISM: Artificial Sequence
<220> FEATURE:
<223> OTHER INFORMATION: synthetic

<400> SEQUENCE: 211
caggtcatta gcaattat                                                    18

<210> SEQ ID NO 212
<211> LENGTH: 6
<212> TYPE: PRT
<213> ORGANISM: Artificial Sequence
<220> FEATURE:
<223> OTHER INFORMATION: synthetic

<400> SEQUENCE: 212

Gln Val Ile Ser Asn Tyr
1               5

<210> SEQ ID NO 213
<211> LENGTH: 9
<212> TYPE: DNA
<213> ORGANISM: Artificial Sequence
<220> FEATURE:
<223> OTHER INFORMATION: synthetic

<400> SEQUENCE: 213 gctgcatcc                                                              9

<210> SEQ ID NO 214
<211> LENGTH: 3
<212> TYPE: PRT
<213> ORGANISM: Artificial Sequence
<220> FEATURE:
<223> OTHER INFORMATION: synthetic

<400> SEQUENCE: 214

Ala Ala Ser
1

<210> SEQ ID NO 215
<211> LENGTH: 27
<212> TYPE: DNA
<213> ORGANISM: Artificial Sequence
<220> FEATURE:
<223> OTHER INFORMATION: synthetic

<400> SEQUENCE: 215
caaaagtata acagtgcccc tcggacg                                         27

<210> SEQ ID NO 216
<211> LENGTH: 9
<212> TYPE: PRT
<213> ORGANISM: Artificial Sequence
<220> FEATURE:
<223> OTHER INFORMATION: synthetic

<400> SEQUENCE: 216

Gln Lys Tyr Asn Ser Ala Pro Arg Thr
1               5

<210> SEQ ID NO 217
<211> LENGTH: 360
<212> TYPE: DNA
<213> ORGANISM: Artificial Sequence
<220> FEATURE:
<223> OTHER INFORMATION: synthetic

<400> SEQUENCE: 217
gaggtgcagc tggtggagtc tgggggaggc ttggtccagc cggggggagtc cctgagactt      60 tactgtgcag cctctggatt cacctttagt aaatattgga tgaactgggt ccgccaggct     120
ccagggaagg gctggagtg gtggccaac ataaagggag atggaagtga aaatactat         180 gtggactctg tgaagggccg gttcaccatc tccagagaca cgccaagaa ctcactatat       240 ctacaaatga acagcctgag agccgaggac acggctgttt attactgtgc gagagattat    300
tggggatcag gctactactt tgacttctgg ggccagggaa ccctggtcac cgtctcctca    360

```
<210> SEQ ID NO 218
<211> LENGTH: 120
<212> TYPE: PRT
<213> ORGANISM: Artificial Sequence
<220> FEATURE:
<223> OTHER INFORMATION: synthetic

<400> SEQUENCE: 218
```

Glu Val Gln Leu Val Glu Ser Gly Gly Gly Leu Val Gln Arg Gly Glu
1               5                   10                  15

Ser Leu Arg Leu Tyr Cys Ala Ala Ser Gly Phe Thr Phe Ser Lys Tyr
            20                  25                  30

Trp Met Asn Trp Val Arg Gln Ala Pro Gly Lys Gly Leu Glu Trp Val
        35                  40                  45

Ala Asn Ile Lys Gly Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Trp Gly Ser Gly Tyr Tyr Phe Asp Phe Trp Gly Gln
            100                 105                 110

Gly Thr Leu Val Thr Val Ser Ser
        115                 120

```
<210> SEQ ID NO 219
<211> LENGTH: 24
<212> TYPE: DNA
<213> ORGANISM: Artificial Sequence
<220> FEATURE:
<223> OTHER INFORMATION: synthetic

<400> SEQUENCE: 219
ggattcacct ttagtaaata ttgg                                         24

<210> SEQ ID NO 220
<211> LENGTH: 8
<212> TYPE: PRT
<213> ORGANISM: Artificial Sequence
<220> FEATURE:
<223> OTHER INFORMATION: synthetic

<400> SEQUENCE: 220
```

Gly Phe Thr Phe Ser Lys Tyr Trp
1               5

```
<210> SEQ ID NO 221
<211> LENGTH: 24
<212> TYPE: DNA
<213> ORGANISM: Artificial Sequence
<220> FEATURE:
<223> OTHER INFORMATION: synthetic

<400> SEQUENCE: 221
ataaagggag atggaagtga gaaa                                         24

<210> SEQ ID NO 222
<211> LENGTH: 8
<212> TYPE: PRT
<213> ORGANISM: Artificial Sequence
<220> FEATURE:
<223> OTHER INFORMATION: synthetic

<400> SEQUENCE: 222
```

Ile Lys Gly Asp Gly Ser Glu Lys
1               5

<210> SEQ ID NO 223
<211> LENGTH: 39
<212> TYPE: DNA
<213> ORGANISM: Artificial Sequence
<220> FEATURE:
<223> OTHER INFORMATION: synthetic

<400> SEQUENCE: 223
gcgagagatt attggggatc aggctactac tttgacttc                39

<210> SEQ ID NO 224
<211> LENGTH: 13
<212> TYPE: PRT
<213> ORGANISM: Artificial Sequence
<220> FEATURE:
<223> OTHER INFORMATION: synthetic

<400> SEQUENCE: 224

Ala Arg Asp Tyr Trp Gly Ser Gly Tyr Tyr Phe Asp Phe
1               5                   10

<210> SEQ ID NO 225
<211> LENGTH: 321
<212> TYPE: DNA
<213> ORGANISM: Artificial Sequence
<220> FEATURE:
<223> OTHER INFORMATION: synthetic

<400> SEQUENCE: 225
gacatccaga tgacccagtc tccatcctcc ctgtctgcat ctgtaggaga cagagtcacc    60
atcacttgcc gggcaagtca gaacattaac aactatttaa attggtatca gcagaaacca   120
gggaaagccc ctaaactcct gatctatgct gcatccagtt tccaaaatgc ggtcccatca   180
aggttcagtg gcagtggatc tgggacagat ttcactctca ccatcagcag tctgcaacct   240
gaagattttg caacttacta ctgtcaacag agttacaata ccccgctcac tttcggcggg   300
gggaccaagg tggagatcaa a                                             321

<210> SEQ ID NO 226
<211> LENGTH: 107
<212> TYPE: PRT
<213> ORGANISM: Artificial Sequence
<220> FEATURE:
<223> OTHER INFORMATION: synthetic

<400> SEQUENCE: 226

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Phe Gln Asn Ala Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Leu
                85                  90                  95

Thr Phe Gly Gly Gly Thr Lys Val Glu Ile Lys
            100                 105

<210> SEQ ID NO 227
<211> LENGTH: 18
<212> TYPE: DNA
<213> ORGANISM: Artificial Sequence
<220> FEATURE:
<223> OTHER INFORMATION: synthetic

<400> SEQUENCE: 227
cagaacatta acaactat                                                 18

<210> SEQ ID NO 228
<211> LENGTH: 6
<212> TYPE: PRT
<213> ORGANISM: Artificial Sequence
<220> FEATURE:
<223> OTHER INFORMATION: synthetic

<400> SEQUENCE: 228

Gln Asn Ile Asn Asn Tyr
1               5

<210> SEQ ID NO 229
<211> LENGTH: 9
<212> TYPE: DNA
<213> ORGANISM: Artificial Sequence
<220> FEATURE:
<223> OTHER INFORMATION: synthetic

<400> SEQUENCE: 229 gctgcatcc                                                            9

<210> SEQ ID NO 230
<211> LENGTH: 3
<212> TYPE: PRT
<213> ORGANISM: Artificial Sequence
<220> FEATURE:
<223> OTHER INFORMATION: synthetic

<400> SEQUENCE: 230

Ala Ala Ser
1

<210> SEQ ID NO 231
<211> LENGTH: 27
<212> TYPE: DNA
<213> ORGANISM: Artificial Sequence
<220> FEATURE:
<223> OTHER INFORMATION: synthetic

<400> SEQUENCE: 231
caacagagtt acaataccccc gctcact                                       27

<210> SEQ ID NO 232
<211> LENGTH: 9
<212> TYPE: PRT
<213> ORGANISM: Artificial Sequence
<220> FEATURE:
<223> OTHER INFORMATION: synthetic

<400> SEQUENCE: 232

Gln Gln Ser Tyr Asn Thr Pro Leu Thr
1               5

<210> SEQ ID NO 233
<211> LENGTH: 390
<212> TYPE: DNA
<213> ORGANISM: Artificial Sequence
<220> FEATURE:
<223> OTHER INFORMATION: synthetic

<400> SEQUENCE: 233

```
gaggtgcagc tggtggagtc tgggggaggc ttggtccagt ctgggggtc cctgagactc      60
tcctgtgcag cctctggatt cacctttagt agctattgga tgagctgggt ccgccaggct    120
ccagggaagg gctggagtg gtggccaac ataaagcaag atggaagtga aaatactat       180
gtggactctg tgaagggccg attcaccatc tccagagaca acgccaagaa ctcactgtat    240
ctgcaaatga acagcctgag agccgatgac acggctgtgt attactgtgc gagagatgat    300
attgtagtag taccagctcc tatgggatat tactactact acttcggtat ggacgtctgg    360
ggccaaggga ccacggtcac cgtctcctca                                     390
```

<210> SEQ ID NO 234
<211> LENGTH: 130
<212> TYPE: PRT
<213> ORGANISM: Artificial Sequence
<220> FEATURE:
<223> OTHER INFORMATION: synthetic

<400> SEQUENCE: 234

Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Asp Ile Val Val Val Pro Ala Pro Met Gly Tyr Tyr Tyr
            100                 105                 110

Tyr Tyr Phe Gly Met Asp Val Trp Gly Gln Gly Thr Thr Val Thr Val
        115                 120                 125

Ser Ser
    130

<210> SEQ ID NO 235
<211> LENGTH: 24
<212> TYPE: DNA
<213> ORGANISM: Artificial Sequence
<220> FEATURE:
<223> OTHER INFORMATION: synthetic

<400> SEQUENCE: 235

```
ggattcacct ttagtagcta ttgg                                           24
```

<210> SEQ ID NO 236
<211> LENGTH: 8
<212> TYPE: PRT
<213> ORGANISM: Artificial Sequence
<220> FEATURE:
<223> OTHER INFORMATION: synthetic

<400> SEQUENCE: 236

Gly Phe Thr Phe Ser Ser Tyr Trp
1               5

<210> SEQ ID NO 237
<211> LENGTH: 24
<212> TYPE: DNA
<213> ORGANISM: Artificial Sequence
<220> FEATURE:
<223> OTHER INFORMATION: synthetic

<400> SEQUENCE: 237
ataaagcaag atggaagtga gaaa                                          24

<210> SEQ ID NO 238
<211> LENGTH: 8
<212> TYPE: PRT
<213> ORGANISM: Artificial Sequence
<220> FEATURE:
<223> OTHER INFORMATION: synthetic

<400> SEQUENCE: 238

Ile Lys Gln Asp Gly Ser Glu Lys
1               5

<210> SEQ ID NO 239
<211> LENGTH: 69
<212> TYPE: DNA
<213> ORGANISM: Artificial Sequence
<220> FEATURE:
<223> OTHER INFORMATION: synthetic

<400> SEQUENCE: 239
gcgagagatg atattgtagt agtaccagct cctatgggat attactacta ctacttcggt    60
atggacgtc                                                           69

<210> SEQ ID NO 240
<211> LENGTH: 23
<212> TYPE: PRT
<213> ORGANISM: Artificial Sequence
<220> FEATURE:
<223> OTHER INFORMATION: synthetic

<400> SEQUENCE: 240

Ala Arg Asp Asp Ile Val Val Pro Ala Pro Met Gly Tyr Tyr Tyr
1               5                   10                  15

Tyr Tyr Phe Gly Met Asp Val
            20

<210> SEQ ID NO 241
<211> LENGTH: 321
<212> TYPE: DNA
<213> ORGANISM: Artificial Sequence
<220> FEATURE:
<223> OTHER INFORMATION: synthetic

<400> SEQUENCE: 241
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgtacac ttttggccag    300
gggaccaagc tggagatcaa a                                             321

<210> SEQ ID NO 242
<211> LENGTH: 107
<212> TYPE: PRT
<213> ORGANISM: Artificial Sequence
<220> FEATURE:
<223> OTHER INFORMATION: synthetic

<400> SEQUENCE: 242

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 243
<211> LENGTH: 18
<212> TYPE: DNA
<213> ORGANISM: Artificial Sequence
<220> FEATURE:
<223> OTHER INFORMATION: synthetic

<400> SEQUENCE: 243
cagggcatta gaaatgat                                                 18

<210> SEQ ID NO 244
<211> LENGTH: 6
<212> TYPE: PRT
<213> ORGANISM: Artificial Sequence
<220> FEATURE:
<223> OTHER INFORMATION: synthetic

<400> SEQUENCE: 244

Gln Gly Ile Arg Asn Asp
1               5

<210> SEQ ID NO 245
<211> LENGTH: 9
<212> TYPE: DNA
<213> ORGANISM: Artificial Sequence
<220> FEATURE:
<223> OTHER INFORMATION: synthetic

<400> SEQUENCE: 245 gctgcatcc                                                           9

<210> SEQ ID NO 246
<211> LENGTH: 3
<212> TYPE: PRT
<213> ORGANISM: Artificial Sequence
<220> FEATURE:
<223> OTHER INFORMATION: synthetic

<400> SEQUENCE: 246

Ala Ala Ser
1

<210> SEQ ID NO 247
<211> LENGTH: 27
<212> TYPE: DNA
<213> ORGANISM: Artificial Sequence
<220> FEATURE:
<223> OTHER INFORMATION: synthetic

<400> SEQUENCE: 247
ctacagcata atagttaccc gtacact                                          27

<210> SEQ ID NO 248
<211> LENGTH: 9
<212> TYPE: PRT
<213> ORGANISM: Artificial Sequence
<220> FEATURE:
<223> OTHER INFORMATION: synthetic

<400> SEQUENCE: 248

Leu Gln His Asn Ser Tyr Pro Tyr Thr
1               5

<210> SEQ ID NO 249
<211> LENGTH: 369
<212> TYPE: DNA
<213> ORGANISM: Artificial Sequence
<220> FEATURE:
<223> OTHER INFORMATION: synthetic

<400> SEQUENCE: 249
gaagtgcagc tggtggagtc tgggggaggc ttggttcagc ctggcaggtc cctgagactc      60
tcctgtgcag cctctggatt cacctttgat gattttgcca tgcactgggt ccgacaagct     120
ccagggaagg gcctggagtg ggtctcaggt attagttgga ctggtggtaa catggactat     180
gcgaactctg tgaagggccg attcaccatc tccagagagg acgccaagaa ttccctgtat     240
ctgcaaatga acagtctgag agctgcggac acggccttgt attactgtgt aaaagatata     300 aggggggatag tggctacggg gggggctttt gatatctggg gccgagggac aatggtcacc     360
gtctcttca                                                             369

<210> SEQ ID NO 250
<211> LENGTH: 123
<212> TYPE: PRT
<213> ORGANISM: Artificial Sequence
<220> FEATURE:
<223> OTHER INFORMATION: synthetic

<400> SEQUENCE: 250

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Phe
            20                  25                  30

Ala Met His Trp Val Arg Gln Ala Pro Gly Lys Gly Leu Glu Trp Val
        35                  40                  45

Ser Gly Ile Ser Trp Thr Gly Gly Asn Met Asp Tyr Ala Asn Ser Val
    50                  55                  60

Lys Gly Arg Phe Thr Ile Ser Arg Glu Asp Ala Lys Asn Ser Leu Tyr
65                  70                  75                  80

Leu Gln Met Asn Ser Leu Arg Ala Ala Asp Thr Ala Leu Tyr Tyr Cys
                85                  90                  95

Val Lys Asp Ile Arg Gly Ile Val Ala Thr Gly Gly Ala Phe Asp Ile
            100                 105                 110

Trp Gly Arg Gly Thr Met Val Thr Val Ser Ser
        115                 120

<210> SEQ ID NO 251
<211> LENGTH: 24
<212> TYPE: DNA
<213> ORGANISM: Artificial Sequence
<220> FEATURE:
<223> OTHER INFORMATION: synthetic

<400> SEQUENCE: 251
ggattcacct ttgatgattt tgcc                                              24

<210> SEQ ID NO 252
<211> LENGTH: 8
<212> TYPE: PRT
<213> ORGANISM: Artificial Sequence
<220> FEATURE:
<223> OTHER INFORMATION: synthetic

<400> SEQUENCE: 252

Gly Phe Thr Phe Asp Asp Phe Ala
1               5

<210> SEQ ID NO 253
<211> LENGTH: 24
<212> TYPE: DNA
<213> ORGANISM: Artificial Sequence
<220> FEATURE:
<223> OTHER INFORMATION: synthetic

<400> SEQUENCE: 253
attagttgga ctggtggtaa catg                                              24

<210> SEQ ID NO 254
<211> LENGTH: 8
<212> TYPE: PRT
<213> ORGANISM: Artificial Sequence
<220> FEATURE:
<223> OTHER INFORMATION: synthetic

<400> SEQUENCE: 254

Ile Ser Trp Thr Gly Gly Asn Met
1               5

<210> SEQ ID NO 255
<211> LENGTH: 48
<212> TYPE: DNA
<213> ORGANISM: Artificial Sequence
<220> FEATURE:
<223> OTHER INFORMATION: synthetic

<400> SEQUENCE: 255
gtaaaagata taaggggat agtggctacg ggggggcctt ttgatatc                    48

<210> SEQ ID NO 256
<211> LENGTH: 16
<212> TYPE: PRT
<213> ORGANISM: Artificial Sequence
<220> FEATURE:
<223> OTHER INFORMATION: synthetic

<400> SEQUENCE: 256

Val Lys Asp Ile Arg Gly Ile Val Ala Thr Gly Gly Ala Phe Asp Ile
1               5                   10                  15

<210> SEQ ID NO 257
<211> LENGTH: 321
<212> TYPE: DNA
<213> ORGANISM: Artificial Sequence
<220> FEATURE:
<223> OTHER INFORMATION: synthetic

<400> SEQUENCE: 257
gacatccaga tgacccagtc tccatcctcc ctgtctgcat ctgtaggaga cagagtcacc    60
atctcttgcc gggcaagtca gaccattagc acttatttaa attggtttca gcagaaacca   120
gggaaagccc ctaagctcct gatctatgtt gtgtccagtt tgcaaagtgg ggtcccatca   180
aggttcagtg gcagtggatc tgggacagat ttcactctca ccatcagcag tctgcaacct   240
gaagattttg caacttatta ctgtcaacag agttacagta cccccattca ctttggccct   300
gggaccaaag tggatatcaa a                                             321

<210> SEQ ID NO 258
<211> LENGTH: 107
<212> TYPE: PRT
<213> ORGANISM: Artificial Sequence
<220> FEATURE:
<223> OTHER INFORMATION: synthetic

<400> SEQUENCE: 258

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Thr Ile Ser Thr Tyr
                20                  25                  30

Leu Asn Trp Phe Gln Gln Lys Pro Gly Lys Ala Pro Lys Leu Leu Ile
            35                  40                  45

Tyr Val Val Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 259
<211> LENGTH: 18
<212> TYPE: DNA
<213> ORGANISM: Artificial Sequence
<220> FEATURE:
<223> OTHER INFORMATION: synthetic

<400> SEQUENCE: 259
cagaccatta gcacttat                                                  18

<210> SEQ ID NO 260
<211> LENGTH: 6
<212> TYPE: PRT
<213> ORGANISM: Artificial Sequence
<220> FEATURE:
<223> OTHER INFORMATION: synthetic

<400> SEQUENCE: 260

Gln Thr Ile Ser Thr Tyr
1               5

<210> SEQ ID NO 261
<211> LENGTH: 9
<212> TYPE: DNA
<213> ORGANISM: Artificial Sequence
<220> FEATURE:
<223> OTHER INFORMATION: synthetic

<400> SEQUENCE: 261 gttgtgtcc                                                                    9

<210> SEQ ID NO 262
<211> LENGTH: 3
<212> TYPE: PRT
<213> ORGANISM: Artificial Sequence
<220> FEATURE:
<223> OTHER INFORMATION: synthetic

<400> SEQUENCE: 262

Val Val Ser
1

<210> SEQ ID NO 263
<211> LENGTH: 27
<212> TYPE: DNA
<213> ORGANISM: Artificial Sequence
<220> FEATURE:
<223> OTHER INFORMATION: synthetic

<400> SEQUENCE: 263
caacagagtt acagtacccc attcact                                               27

<210> SEQ ID NO 264
<211> LENGTH: 9
<212> TYPE: PRT
<213> ORGANISM: Artificial Sequence
<220> FEATURE:
<223> OTHER INFORMATION: synthetic

<400> SEQUENCE: 264

Gln Gln Ser Tyr Ser Thr Pro Phe Thr
1               5

<210> SEQ ID NO 265
<211> LENGTH: 345
<212> TYPE: DNA
<213> ORGANISM: Artificial Sequence
<220> FEATURE:
<223> OTHER INFORMATION: synthetic

<400> SEQUENCE: 265
gaggtgcagc tggtggagtc tggaggaggc ttggtccagc cggggggtc cctgagactc            60 tcctgtgcag cctctggatt caccgtcggt accaactaca tgaactgggt ccgccaggct          120
ccagggaagg gactggagtg gatctcagtt atttatagcg gtggtagcac attctacgca          180
gactccgtga agggccgatt caccatctcc agacagactt cccagaacac gctgtatctt          240
caaatgaaca gcctgagacc tgaggacacg gccgtatatt actgtgcgag aggtatacgt          300
ggttttgata tctggggcca aggacaatg gtcaccgtct cttca                           345

<210> SEQ ID NO 266

```
<211> LENGTH: 115
<212> TYPE: PRT
<213> ORGANISM: Artificial Sequence
<220> FEATURE:
<223> OTHER INFORMATION: synthetic

<400> SEQUENCE: 266

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Gly Thr Asn
            20                  25                  30

Tyr Met Asn Trp Val Arg Gln Ala Pro Gly Lys Gly Leu Glu Trp Ile
        35                  40                  45

Ser Val Ile Tyr Ser Gly Gly Ser Thr Phe Tyr Ala Asp Ser Val Lys
    50                  55                  60

Gly Arg Phe Thr Ile Ser Arg Gln Thr Ser Gln Asn Thr Leu Tyr Leu
65                  70                  75                  80

Gln Met Asn Ser Leu Arg Pro Glu Asp Thr Ala Val Tyr Tyr Cys Ala
                85                  90                  95

Arg Gly Ile Arg Gly Phe Asp Ile Trp Gly Gln Gly Thr Met Val Thr
            100                 105                 110

Val Ser Ser
        115

<210> SEQ ID NO 267
<211> LENGTH: 24
<212> TYPE: DNA
<213> ORGANISM: Artificial Sequence
<220> FEATURE:
<223> OTHER INFORMATION: synthetic

<400> SEQUENCE: 267
ggattcaccg tcggtaccaa ctac                                      24

<210> SEQ ID NO 268
<211> LENGTH: 8
<212> TYPE: PRT
<213> ORGANISM: Artificial Sequence
<220> FEATURE:
<223> OTHER INFORMATION: synthetic

<400> SEQUENCE: 268

Gly Phe Thr Val Gly Thr Asn Tyr
1               5

<210> SEQ ID NO 269
<211> LENGTH: 21
<212> TYPE: DNA
<213> ORGANISM: Artificial Sequence
<220> FEATURE:
<223> OTHER INFORMATION: synthetic

<400> SEQUENCE: 269
atttatagcg gtggtagcac a                                         21

<210> SEQ ID NO 270
<211> LENGTH: 7
<212> TYPE: PRT
<213> ORGANISM: Artificial Sequence
<220> FEATURE:
<223> OTHER INFORMATION: synthetic

<400> SEQUENCE: 270
```

Ile Tyr Ser Gly Gly Ser Thr
1               5

<210> SEQ ID NO 271
<211> LENGTH: 27
<212> TYPE: DNA
<213> ORGANISM: Artificial Sequence
<220> FEATURE:
<223> OTHER INFORMATION: synthetic

<400> SEQUENCE: 271
gcgagaggta tacgtggttt tgatatc                                          27

<210> SEQ ID NO 272
<211> LENGTH: 9
<212> TYPE: PRT
<213> ORGANISM: Artificial Sequence
<220> FEATURE:
<223> OTHER INFORMATION: synthetic

<400> SEQUENCE: 272

Ala Arg Gly Ile Arg Gly Phe Asp Ile
1               5

<210> SEQ ID NO 273
<211> LENGTH: 324
<212> TYPE: DNA
<213> ORGANISM: Artificial Sequence
<220> FEATURE:
<223> OTHER INFORMATION: synthetic

<400> SEQUENCE: 273
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                           324

<210> SEQ ID NO 274
<211> LENGTH: 108
<212> TYPE: PRT
<213> ORGANISM: Artificial Sequence
<220> FEATURE:
<223> OTHER INFORMATION: synthetic

<400> SEQUENCE: 274

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys

```
<210> SEQ ID NO 275
<211> LENGTH: 18
<212> TYPE: DNA
<213> ORGANISM: Artificial Sequence
<220> FEATURE:
<223> OTHER INFORMATION: synthetic

<400> SEQUENCE: 275
cagagcatta gcagctat                                                 18

<210> SEQ ID NO 276
<211> LENGTH: 6
<212> TYPE: PRT
<213> ORGANISM: Artificial Sequence
<220> FEATURE:
<223> OTHER INFORMATION: synthetic

<400> SEQUENCE: 276

Gln Ser Ile Ser Ser Tyr
1               5

<210> SEQ ID NO 277
<211> LENGTH: 9
<212> TYPE: DNA
<213> ORGANISM: Artificial Sequence
<220> FEATURE:
<223> OTHER INFORMATION: synthetic

<400> SEQUENCE: 277 gctgcatcc                                                            9

<210> SEQ ID NO 278
<211> LENGTH: 3
<212> TYPE: PRT
<213> ORGANISM: Artificial Sequence
<220> FEATURE:
<223> OTHER INFORMATION: synthetic

<400> SEQUENCE: 278

Ala Ala Ser
1

<210> SEQ ID NO 279
<211> LENGTH: 30
<212> TYPE: DNA
<213> ORGANISM: Artificial Sequence
<220> FEATURE:
<223> OTHER INFORMATION: synthetic

<400> SEQUENCE: 279
caacagagtt acagtacccc tccgatcacc                                    30

<210> SEQ ID NO 280
<211> LENGTH: 10
<212> TYPE: PRT
<213> ORGANISM: Artificial Sequence
<220> FEATURE:
<223> OTHER INFORMATION: synthetic

<400> SEQUENCE: 280

Gln Gln Ser Tyr Ser Thr Pro Pro Ile Thr
1               5                   10

<210> SEQ ID NO 281
```

<211> LENGTH: 345
<212> TYPE: DNA
<213> ORGANISM: Artificial Sequence
<220> FEATURE:
<223> OTHER INFORMATION: synthetic

<400> SEQUENCE: 281

| | | |
|---|---|---|
| gaggtgcagc tggtggagtc tgggggaggc ttggtccagc cggggggtc cctgagactc | 60 |
| tcctgtgcag cctctgggtt taccatcagt accaactaca tgaactgggt ccgccaggct | 120 |
| ccagggaagg ggctggagtg ggtcgcagtt atttatagca gtggttccac atactatatc | 180 |
| gactccgtga agggccgatt caccatctcc agactcactt ccaagaacac ggtgtatctt | 240 |
| caaatgagca gcctgaattc tgaagacacg gccgtgtatt actgtgcgag ggggatcagg | 300 |
| ggttttgata tttggggcca agggacaatg gtcaccgtct cttca | 345 |

<210> SEQ ID NO 282
<211> LENGTH: 115
<212> TYPE: PRT
<213> ORGANISM: Artificial Sequence
<220> FEATURE:
<223> OTHER INFORMATION: synthetic

<400> SEQUENCE: 282

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Thr Asn
            20                  25                  30

Tyr Met Asn Trp Val Arg Gln Ala Pro Gly Lys Gly Leu Glu Trp Val
        35                  40                  45

Ala Val Ile Tyr Ser Ser Gly Ser Thr Tyr Tyr Ile Asp Ser Val Lys
    50                  55                  60

Gly Arg Phe Thr Ile Ser Arg Leu Thr Ser Lys Asn Thr Val Tyr Leu
65                  70                  75                  80

Gln Met Ser Ser Leu Asn Ser Glu Asp Thr Ala Val Tyr Tyr Cys Ala
                85                  90                  95

Arg Gly Ile Arg Gly Phe Asp Ile Trp Gly Gln Gly Thr Met Val Thr
            100                 105                 110

Val Ser Ser
        115

<210> SEQ ID NO 283
<211> LENGTH: 24
<212> TYPE: DNA
<213> ORGANISM: Artificial Sequence
<220> FEATURE:
<223> OTHER INFORMATION: synthetic

<400> SEQUENCE: 283
gggtttacca tcagtaccaa ctac                                          24

<210> SEQ ID NO 284
<211> LENGTH: 8
<212> TYPE: PRT
<213> ORGANISM: Artificial Sequence
<220> FEATURE:
<223> OTHER INFORMATION: synthetic

<400> SEQUENCE: 284

Gly Phe Thr Ile Ser Thr Asn Tyr
1               5

<210> SEQ ID NO 285
<211> LENGTH: 21
<212> TYPE: DNA
<213> ORGANISM: Artificial Sequence
<220> FEATURE:
<223> OTHER INFORMATION: synthetic

<400> SEQUENCE: 285
atttatagca gtggttccac a                                               21

<210> SEQ ID NO 286
<211> LENGTH: 7
<212> TYPE: PRT
<213> ORGANISM: Artificial Sequence
<220> FEATURE:
<223> OTHER INFORMATION: synthetic

<400> SEQUENCE: 286

Ile Tyr Ser Ser Gly Ser Thr
1               5

<210> SEQ ID NO 287
<211> LENGTH: 27
<212> TYPE: DNA
<213> ORGANISM: Artificial Sequence
<220> FEATURE:
<223> OTHER INFORMATION: synthetic

<400> SEQUENCE: 287
gcgaggggga tcagggdttt tgatatt                                         27

<210> SEQ ID NO 288
<211> LENGTH: 9
<212> TYPE: PRT
<213> ORGANISM: Artificial Sequence
<220> FEATURE:
<223> OTHER INFORMATION: synthetic

<400> SEQUENCE: 288

Ala Arg Gly Ile Arg Gly Phe Asp Ile
1               5

<210> SEQ ID NO 289
<211> LENGTH: 372
<212> TYPE: DNA
<213> ORGANISM: Artificial Sequence
<220> FEATURE:
<223> OTHER INFORMATION: synthetic

<400> SEQUENCE: 289
gaagtgcagc tggtggagtc ggggggaggc ttggtacagc ctggcaggtc cctgagactc      60
tcctgtgcag cctctggatt caccattgat gatagtgcca tgcactgggt ccggcaaact     120
ccagggaagg gcctgagtg gtctcaggt attagttgga aaagtggtag cataggttat       180
gcggactctg tgaggggccg attcaccatc tccagagaca cgccaagaa ttccctctat      240 ctgcaaatga acagtctgag agttgaggac acggccttgt attactgtgt aaaagatata    300
aggggcaact ggaactacgg gggaaactgg ttcgacccct ggggccaggg aaccctggtc    360
actgtctcct ca                                                        372

<210> SEQ ID NO 290
<211> LENGTH: 124
<212> TYPE: PRT
<213> ORGANISM: Artificial Sequence

```
<220> FEATURE:
<223> OTHER INFORMATION: synthetic

<400> SEQUENCE: 290

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Ile Asp Asp Ser
            20                  25                  30

Ala Met His Trp Val Arg Gln Thr Pro Gly Lys Gly Leu Glu Trp Val
        35                  40                  45

Ser Gly Ile Ser Trp Lys Ser Gly Ser Ile Gly Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
                85                  90                  95

Val Lys Asp Ile Arg Gly Asn Trp Asn Tyr Gly Gly Asn Trp Phe Asp
            100                 105                 110

Pro Trp Gly Gln Gly Thr Leu Val Thr Val Ser Ser
        115                 120

<210> SEQ ID NO 291
<211> LENGTH: 24
<212> TYPE: DNA
<213> ORGANISM: Artificial Sequence
<220> FEATURE:
<223> OTHER INFORMATION: synthetic

<400> SEQUENCE: 291
ggattcacca ttgatgatag tgcc                                              24

<210> SEQ ID NO 292
<211> LENGTH: 8
<212> TYPE: PRT
<213> ORGANISM: Artificial Sequence
<220> FEATURE:
<223> OTHER INFORMATION: synthetic

<400> SEQUENCE: 292

Gly Phe Thr Ile Asp Asp Ser Ala
1               5

<210> SEQ ID NO 293
<211> LENGTH: 24
<212> TYPE: DNA
<213> ORGANISM: Artificial Sequence
<220> FEATURE:
<223> OTHER INFORMATION: synthetic

<400> SEQUENCE: 293
attagttgga aaagtggtag cata                                              24

<210> SEQ ID NO 294
<211> LENGTH: 8
<212> TYPE: PRT
<213> ORGANISM: Artificial Sequence
<220> FEATURE:
<223> OTHER INFORMATION: synthetic

<400> SEQUENCE: 294

Ile Ser Trp Lys Ser Gly Ser Ile
1               5
```

<210> SEQ ID NO 295
<211> LENGTH: 51
<212> TYPE: DNA
<213> ORGANISM: Artificial Sequence
<220> FEATURE:
<223> OTHER INFORMATION: synthetic

<400> SEQUENCE: 295
gtaaaagata taaggggcaa ctggaactac gggggaaact ggttcgaccc c            51

<210> SEQ ID NO 296
<211> LENGTH: 17
<212> TYPE: PRT
<213> ORGANISM: Artificial Sequence
<220> FEATURE:
<223> OTHER INFORMATION: synthetic

<400> SEQUENCE: 296

Val Lys Asp Ile Arg Gly Asn Trp Asn Tyr Gly Gly Asn Trp Phe Asp
1               5                   10                  15

Pro

<210> SEQ ID NO 297
<211> LENGTH: 345
<212> TYPE: DNA
<213> ORGANISM: Artificial Sequence
<220> FEATURE:
<223> OTHER INFORMATION: synthetic

<400> SEQUENCE: 297
gaggtgcagc tggtggagtc tggaggaggc ttggtccagc ctggggggtc cctgagactc    60
tcatgtgaag cctctgggtt caccgtcggt gtcaaccaca tgaactgggt ccgccaggct   120
ccagggaagg gtctggagtg ggtctcagtt attttcagta gtggtaggac attctacgga   180
gactacgtga agggccgatt aaccatcttc agacaaacct cccagaacac ggtgtatctt   240
caaatgaata gcctgagaag tgaggacacg gccatatatt actgtgcgag agggattggc   300
ggtttggaca tctggggccg aggacaatg gtcaccgtct cttca                    345

<210> SEQ ID NO 298
<211> LENGTH: 115
<212> TYPE: PRT
<213> ORGANISM: Artificial Sequence
<220> FEATURE:
<223> OTHER INFORMATION: synthetic

<400> SEQUENCE: 298

Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Val Gly Val Asn
                20                  25                  30

His Met Asn Trp Val Arg Gln Ala Pro Gly Lys Gly Leu Glu Trp Val
            35                  40                  45

Ser Val Ile Phe Ser Ser Gly Arg Thr Phe Tyr Gly Asp Tyr Val Lys
        50                  55                  60

Gly Arg Leu Thr Ile Phe Arg Gln Thr Ser Gln Asn Thr Val Tyr Leu
65                  70                  75                  80

Gln Met Asn Ser Leu Arg Ser Glu Asp Thr Ala Ile Tyr Tyr Cys Ala
                85                  90                  95

Arg Gly Ile Gly Gly Leu Asp Ile Trp Gly Arg Gly Thr Met Val Thr
            100                 105                 110

Val Ser Ser
    115

<210> SEQ ID NO 299
<211> LENGTH: 24
<212> TYPE: DNA
<213> ORGANISM: Artificial Sequence
<220> FEATURE:
<223> OTHER INFORMATION: synthetic

<400> SEQUENCE: 299
gggttcaccg tcggtgtcaa ccac                                          24

<210> SEQ ID NO 300
<211> LENGTH: 8
<212> TYPE: PRT
<213> ORGANISM: Artificial Sequence
<220> FEATURE:
<223> OTHER INFORMATION: synthetic

<400> SEQUENCE: 300

Gly Phe Thr Val Gly Val Asn His
1               5

<210> SEQ ID NO 301
<211> LENGTH: 21
<212> TYPE: DNA
<213> ORGANISM: Artificial Sequence
<220> FEATURE:
<223> OTHER INFORMATION: synthetic

<400> SEQUENCE: 301
attttcagta gtggtaggac a                                             21

<210> SEQ ID NO 302
<211> LENGTH: 7
<212> TYPE: PRT
<213> ORGANISM: Artificial Sequence
<220> FEATURE:
<223> OTHER INFORMATION: synthetic

<400> SEQUENCE: 302

Ile Phe Ser Ser Gly Arg Thr
1               5

<210> SEQ ID NO 303
<211> LENGTH: 27
<212> TYPE: DNA
<213> ORGANISM: Artificial Sequence
<220> FEATURE:
<223> OTHER INFORMATION: synthetic

<400> SEQUENCE: 303
gcgagaggga ttggcggttt ggacatc                                       27

<210> SEQ ID NO 304
<211> LENGTH: 9
<212> TYPE: PRT
<213> ORGANISM: Artificial Sequence
<220> FEATURE:
<223> OTHER INFORMATION: synthetic

<400> SEQUENCE: 304

Ala Arg Gly Ile Gly Gly Leu Asp Ile
1               5

<210> SEQ ID NO 305
<211> LENGTH: 369
<212> TYPE: DNA
<213> ORGANISM: Artificial Sequence
<220> FEATURE:
<223> OTHER INFORMATION: synthetic

<400> SEQUENCE: 305

```
gaagtgcagc tggtggagtc tgggggaggc ttggttcagc ctggcaggtc cctaagactc      60
tcctgtgcag cctctggatt cacctttgat gattatgcct tgcactgggt ccggcaagct     120
ccagggaagg gcctggagtg gtctcaggt attagttgga ctggtggtac tatagactat     180
gcggactctg tgaagggccg attcaccatc tccagagaca acgccaagaa ctccctgtat     240
ctgcaaatga gcagtctgag aactgaggac acggccatat attactgtac aagagatatc     300
cgggggaact ggaagtacgg aggctggttc gaccctggg gccagggaac cctggtcacc     360
gtctcctca                                                            369
```

<210> SEQ ID NO 306
<211> LENGTH: 123
<212> TYPE: PRT
<213> ORGANISM: Artificial Sequence
<220> FEATURE:
<223> OTHER INFORMATION: synthetic

<400> SEQUENCE: 306

```
Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Asp Tyr
            20                  25                  30
Ala Leu His Trp Val Arg Gln Ala Pro Gly Lys Gly Leu Glu Trp Val
        35                  40                  45
Ser Gly Ile Ser Trp Thr Gly Gly Thr Ile Asp Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Ser Ser Leu Arg Thr Glu Asp Thr Ala Ile Tyr Tyr Cys
                85                  90                  95
Thr Arg Asp Ile Arg Gly Asn Trp Lys Tyr Gly Gly Trp Phe Asp Pro
            100                 105                 110
Trp Gly Gln Gly Thr Leu Val Thr Val Ser Ser
        115                 120
```

<210> SEQ ID NO 307
<211> LENGTH: 24
<212> TYPE: DNA
<213> ORGANISM: Artificial Sequence
<220> FEATURE:
<223> OTHER INFORMATION: synthetic

<400> SEQUENCE: 307

```
ggattcacct ttgatgatta tgcc                                            24
```

<210> SEQ ID NO 308
<211> LENGTH: 8
<212> TYPE: PRT
<213> ORGANISM: Artificial Sequence
<220> FEATURE:
<223> OTHER INFORMATION: synthetic

<400> SEQUENCE: 308

Gly Phe Thr Phe Asp Asp Tyr Ala
1               5

<210> SEQ ID NO 309
<211> LENGTH: 24
<212> TYPE: DNA
<213> ORGANISM: Artificial Sequence
<220> FEATURE:
<223> OTHER INFORMATION: synthetic

<400> SEQUENCE: 309
attagttgga ctggtggtac tata                                          24

<210> SEQ ID NO 310
<211> LENGTH: 8
<212> TYPE: PRT
<213> ORGANISM: Artificial Sequence
<220> FEATURE:
<223> OTHER INFORMATION: synthetic

<400> SEQUENCE: 310

Ile Ser Trp Thr Gly Gly Thr Ile
1               5

<210> SEQ ID NO 311
<211> LENGTH: 48
<212> TYPE: DNA
<213> ORGANISM: Artificial Sequence
<220> FEATURE:
<223> OTHER INFORMATION: synthetic

<400> SEQUENCE: 311
acaagagata tccgggggaa ctggaagtac ggaggctggt tcgacccc                48

<210> SEQ ID NO 312
<211> LENGTH: 16
<212> TYPE: PRT
<213> ORGANISM: Artificial Sequence
<220> FEATURE:
<223> OTHER INFORMATION: synthetic

<400> SEQUENCE: 312

Thr Arg Asp Ile Arg Gly Asn Trp Lys Tyr Gly Gly Trp Phe Asp Pro
1               5                   10                  15

<210> SEQ ID NO 313
<211> LENGTH: 360
<212> TYPE: DNA
<213> ORGANISM: Artificial Sequence
<220> FEATURE:
<223> OTHER INFORMATION: synthetic

<400> SEQUENCE: 313
caggtgcagc tggtgcagtc tgggactgag gtgaagaagc ctggggcctc agtgaaggtc    60
tcctgcaagg cttctggata caccttcacc gcctactata tgcactgggt gcgacaggcc   120
cctggtcaag gacttgactg gatgggatgg atcagcccta acagtggttt cacaaactat   180
gcacagaagt tcagggcag ggtcaccatg accagggaca cgtccatcaa cacattttat    240
atggagctga gtggactgag atctgacgac acggccgtat attactgtgc gcgagaggt    300 tctactcacc acaattcttt cgacccctgg ggccagggaa ccctggtcac cgtctcctca   360

<210> SEQ ID NO 314
<211> LENGTH: 120

```
<212> TYPE: PRT
<213> ORGANISM: Artificial Sequence
<220> FEATURE:
<223> OTHER INFORMATION: synthetic

<400> SEQUENCE: 314

Gln Val Gln Leu Val Gln Ser Gly Thr Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Met His Trp Val Arg Gln Ala Pro Gly Gln Gly Leu Asp Trp Met
        35                  40                  45

Gly Trp Ile Ser Pro Asn Ser Gly Phe Thr Asn Tyr Ala Gln Lys Phe
    50                  55                  60

Gln Gly Arg Val Thr Met Thr Arg Asp Thr Ser Ile Asn Thr Phe Tyr
65                  70                  75                  80

Met Glu Leu Ser Gly Leu Arg Ser Asp Asp Thr Ala Val Tyr Tyr Cys
                85                  90                  95

Ala Arg Glu Gly Ser Thr His His Asn Ser Phe Asp Pro Trp Gly Gln
            100                 105                 110

Gly Thr Leu Val Thr Val Ser Ser
        115                 120

<210> SEQ ID NO 315
<211> LENGTH: 24
<212> TYPE: DNA
<213> ORGANISM: Artificial Sequence
<220> FEATURE:
<223> OTHER INFORMATION: synthetic

<400> SEQUENCE: 315
ggatacacct tcaccgccta ctat                                          24

<210> SEQ ID NO 316
<211> LENGTH: 8
<212> TYPE: PRT
<213> ORGANISM: Artificial Sequence
<220> FEATURE:
<223> OTHER INFORMATION: synthetic

<400> SEQUENCE: 316

Gly Tyr Thr Phe Thr Ala Tyr Tyr
1               5

<210> SEQ ID NO 317
<211> LENGTH: 24
<212> TYPE: DNA
<213> ORGANISM: Artificial Sequence
<220> FEATURE:
<223> OTHER INFORMATION: synthetic

<400> SEQUENCE: 317
atcagcccta acagtggttt caca                                          24

<210> SEQ ID NO 318
<211> LENGTH: 8
<212> TYPE: PRT
<213> ORGANISM: Artificial Sequence
<220> FEATURE:
<223> OTHER INFORMATION: synthetic

<400> SEQUENCE: 318

Ile Ser Pro Asn Ser Gly Phe Thr
```

```
<210> SEQ ID NO 319
<211> LENGTH: 39
<212> TYPE: DNA
<213> ORGANISM: Artificial Sequence
<220> FEATURE:
<223> OTHER INFORMATION: synthetic

<400> SEQUENCE: 319
gcgcgagagg gttctactca ccacaattct ttcgacccc                              39

<210> SEQ ID NO 320
<211> LENGTH: 13
<212> TYPE: PRT
<213> ORGANISM: Artificial Sequence
<220> FEATURE:
<223> OTHER INFORMATION: synthetic

<400> SEQUENCE: 320

Ala Arg Glu Gly Ser Thr His His Asn Ser Phe Asp Pro
 1               5                  10

<210> SEQ ID NO 321
<211> LENGTH: 342
<212> TYPE: DNA
<213> ORGANISM: Artificial Sequence
<220> FEATURE:
<223> OTHER INFORMATION: synthetic

<400> SEQUENCE: 321
gaggtgcagc tggtggagtc tgaggaggc ttggtccaac cggggggggtc cctgaggctc        60 tcctgtgcag cctctgggtt caccgtcggt actaacttca tgaattgggt ccgccaggct       120
ccagggaagg ggctggagtg ggtctcagcg atttatagcg gtggtaccgc taactacgca       180
gactccgtga agggccgatt caccatttcc agagacactt ccaggaacac gctgtatctt       240
caaatgaaca gcctgagaac tgaggacacg gccgtttatt attgtgcgag agggggggt        300 atggacgtct ggggccaagg gaccacggtc accgtctcct ca                          342

<210> SEQ ID NO 322
<211> LENGTH: 114
<212> TYPE: PRT
<213> ORGANISM: Artificial Sequence
<220> FEATURE:
<223> OTHER INFORMATION: synthetic

<400> SEQUENCE: 322

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Gly Thr Asn
            20                  25                  30

Phe Met Asn Trp Val Arg Gln Ala Pro Gly Lys Gly Leu Glu Trp Val
        35                  40                  45

Ser Ala Ile Tyr Ser Gly Gly Thr Ala Asn Tyr Ala Asp Ser Val Lys
    50                  55                  60

Gly Arg Phe Thr Ile Ser Arg Asp Thr Ser Arg Asn Thr Leu Tyr Leu
65                  70                  75                  80

Gln Met Asn Ser Leu Arg Thr Glu Asp Thr Ala Val Tyr Tyr Cys Ala
                85                  90                  95

Arg Gly Gly Gly Met Asp Val Trp Gly Gln Gly Thr Thr Val Thr Val
            100                 105                 110
```

Ser Ser

<210> SEQ ID NO 323
<211> LENGTH: 24
<212> TYPE: DNA
<213> ORGANISM: Artificial Sequence
<220> FEATURE:
<223> OTHER INFORMATION: synthetic

<400> SEQUENCE: 323
gggttcaccg tcggtactaa cttc					24

<210> SEQ ID NO 324
<211> LENGTH: 8
<212> TYPE: PRT
<213> ORGANISM: Artificial Sequence
<220> FEATURE:
<223> OTHER INFORMATION: synthetic

<400> SEQUENCE: 324

Gly Phe Thr Val Gly Thr Asn Phe
1               5

<210> SEQ ID NO 325
<211> LENGTH: 21
<212> TYPE: DNA
<213> ORGANISM: Artificial Sequence
<220> FEATURE:
<223> OTHER INFORMATION: synthetic

<400> SEQUENCE: 325
atttatagcg gtggtaccgc t					21

<210> SEQ ID NO 326
<211> LENGTH: 7
<212> TYPE: PRT
<213> ORGANISM: Artificial Sequence
<220> FEATURE:
<223> OTHER INFORMATION: synthetic

<400> SEQUENCE: 326

Ile Tyr Ser Gly Gly Thr Ala
1               5

<210> SEQ ID NO 327
<211> LENGTH: 24
<212> TYPE: DNA
<213> ORGANISM: Artificial Sequence
<220> FEATURE:
<223> OTHER INFORMATION: synthetic

<400> SEQUENCE: 327
gcgagagggg ggggtatgga cgtc					24

<210> SEQ ID NO 328
<211> LENGTH: 8
<212> TYPE: PRT
<213> ORGANISM: Artificial Sequence
<220> FEATURE:
<223> OTHER INFORMATION: synthetic

<400> SEQUENCE: 328

Ala Arg Gly Gly Gly Met Asp Val
1               5

<210> SEQ ID NO 329
<211> LENGTH: 354
<212> TYPE: DNA
<213> ORGANISM: Artificial Sequence
<220> FEATURE:
<223> OTHER INFORMATION: synthetic

<400> SEQUENCE: 329

```
caggtccagc tggtgcagtc tggggctgag gtgaagaagc ctgggtcctc ggtgaaggtc      60
tcctgcaagg cttctggagg caccttcaac acctatgttc tcagctgggt gcgacaggcc     120
cctggacaag gcttgagtg gatgggagag atcatccta tcttaggtgc agcaaactac       180
gcacagaact tccagggcag agtcactttt accacgacg aatccacgaa tacagcctac      240
atggacctga gcagcctaag atctgaggac acggccgtgt attactgtgc gagagatcgg    300
acctccgggg ggttcgaccc ctggggccag ggaaccctgg tcactgtctc ctca           354
```

<210> SEQ ID NO 330
<211> LENGTH: 118
<212> TYPE: PRT
<213> ORGANISM: Artificial Sequence
<220> FEATURE:
<223> OTHER INFORMATION: synthetic

<400> SEQUENCE: 330

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Thr Tyr
            20                  25                  30

Val Leu Ser Trp Val Arg Gln Ala Pro Gly Gln Gly Leu Glu Trp Met
        35                  40                  45

Gly Glu Ile Ile Pro Ile Leu Gly Ala Ala Asn Tyr Ala Gln Asn Phe
    50                  55                  60

Gln Gly Arg Val Thr Phe Thr Thr Asp Glu Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Asp Arg Thr Ser Gly Gly Phe Asp Pro Trp Gly Gln Gly Thr
            100                 105                 110

Leu Val Thr Val Ser Ser
        115
```

<210> SEQ ID NO 331
<211> LENGTH: 24
<212> TYPE: DNA
<213> ORGANISM: Artificial Sequence
<220> FEATURE:
<223> OTHER INFORMATION: synthetic

<400> SEQUENCE: 331

```
ggaggcacct tcaacaccta tgtt                                              24
```

<210> SEQ ID NO 332
<211> LENGTH: 8
<212> TYPE: PRT
<213> ORGANISM: Artificial Sequence
<220> FEATURE:
<223> OTHER INFORMATION: synthetic

<400> SEQUENCE: 332

```
Gly Gly Thr Phe Asn Thr Tyr Val
1               5
```

<210> SEQ ID NO 333
<211> LENGTH: 24
<212> TYPE: DNA
<213> ORGANISM: Artificial Sequence
<220> FEATURE:
<223> OTHER INFORMATION: synthetic

<400> SEQUENCE: 333 atcatccota tcttaggtgc agca                                          24

<210> SEQ ID NO 334
<211> LENGTH: 8
<212> TYPE: PRT
<213> ORGANISM: Artificial Sequence
<220> FEATURE:
<223> OTHER INFORMATION: synthetic

<400> SEQUENCE: 334

Ile Ile Pro Ile Leu Gly Ala Ala
1               5

<210> SEQ ID NO 335
<211> LENGTH: 33
<212> TYPE: DNA
<213> ORGANISM: Artificial Sequence
<220> FEATURE:
<223> OTHER INFORMATION: synthetic

<400> SEQUENCE: 335
gcgagagatc ggacctccgg ggggttcgac ccc                                33

<210> SEQ ID NO 336
<211> LENGTH: 11
<212> TYPE: PRT
<213> ORGANISM: Artificial Sequence
<220> FEATURE:
<223> OTHER INFORMATION: synthetic

<400> SEQUENCE: 336

Ala Arg Asp Arg Thr Ser Gly Gly Phe Asp Pro
1               5                   10

<210> SEQ ID NO 337
<211> LENGTH: 357
<212> TYPE: DNA
<213> ORGANISM: Artificial Sequence
<220> FEATURE:
<223> OTHER INFORMATION: synthetic

<400> SEQUENCE: 337
caggttcagc tggtgcagtc tggagctgag gtggagaagc ctggggcctc agtgaaggtc    60
tcctgcaagg cttctggtta catctttacc cactatggta tcagctgggt gcgacaggcc   120

```
cctggacaag gacttgagtg ggtgggctgg atcagccctt acaatggtta cacagactat    180
gcacagaaac tccagggcag agtcaccttg accacagaca catccacgac cacagcctac    240
atggagctga ggaacctgag atctgacgac acggccatgt attactgttc gagagggagg    300
ggcccttact ggtccttcga tctctggggc cgtggcaccc tggtcaccgt ctcctca       357
```

<210> SEQ ID NO 338
<211> LENGTH: 119
<212> TYPE: PRT
<213> ORGANISM: Artificial Sequence
<220> FEATURE:
<223> OTHER INFORMATION: synthetic

<400> SEQUENCE: 338

```
Gln Val Gln Leu Val Gln Ser Gly Ala Glu Val Glu Lys Pro Gly Ala
1               5                   10                  15

Ser Val Lys Val Ser Cys Lys Ala Ser Gly Tyr Ile Phe Thr His Tyr
            20                  25                  30

Gly Ile Ser Trp Val Arg Gln Ala Pro Gly Gln Gly Leu Glu Trp Val
        35                  40                  45

Gly Trp Ile Ser Pro Tyr Asn Gly Tyr Thr Asp Tyr Ala Gln Lys Leu
    50                  55                  60

Gln Gly Arg Val Thr Leu Thr Thr Asp Thr Ser Thr Thr Thr Ala Tyr
65                  70                  75                  80

Met Glu Leu Arg Asn Leu Arg Ser Asp Asp Thr Ala Met Tyr Tyr Cys
                85                  90                  95

Ser Arg Gly Arg Gly Pro Tyr Trp Ser Phe Asp Leu Trp Gly Arg Gly
            100                 105                 110

Thr Leu Val Thr Val Ser Ser
        115
```

<210> SEQ ID NO 339
<211> LENGTH: 24
<212> TYPE: DNA
<213> ORGANISM: Artificial Sequence
<220> FEATURE:
<223> OTHER INFORMATION: synthetic

<400> SEQUENCE: 339

```
ggttacatct ttacccacta tggt                                            24
```

<210> SEQ ID NO 340
<211> LENGTH: 8
<212> TYPE: PRT
<213> ORGANISM: Artificial Sequence
<220> FEATURE:

```
<223> OTHER INFORMATION: synthetic

<400> SEQUENCE: 340

Gly Tyr Ile Phe Thr His Tyr Gly
1               5

<210> SEQ ID NO 341
<211> LENGTH: 24
<212> TYPE: DNA
<213> ORGANISM: Artificial Sequence
<220> FEATURE:
<223> OTHER INFORMATION: synthetic

<400> SEQUENCE: 341
atcagccctt acaatggtta caca                                              24

<210> SEQ ID NO 342
<211> LENGTH: 8
<212> TYPE: PRT
<213> ORGANISM: Artificial Sequence
<220> FEATURE:
<223> OTHER INFORMATION: synthetic

<400> SEQUENCE: 342

Ile Ser Pro Tyr Asn Gly Tyr Thr
1               5

<210> SEQ ID NO 343
<211> LENGTH: 36
<212> TYPE: DNA
<213> ORGANISM: Artificial Sequence
<220> FEATURE:
<223> OTHER INFORMATION: synthetic

<400> SEQUENCE: 343
tcgagaggga ggggccctta ctggtccttc gatctc                                 36

<210> SEQ ID NO 344
<211> LENGTH: 12
<212> TYPE: PRT
<213> ORGANISM: Artificial Sequence
<220> FEATURE:
<223> OTHER INFORMATION: synthetic

<400> SEQUENCE: 344

Ser Arg Gly Arg Gly Pro Tyr Trp Ser Phe Asp Leu
1               5                   10
```